（12） United States Patent
van Staden et al.

(10) Patent No.: US 12,173,344 B2
(45) Date of Patent: Dec. 24, 2024

(54) FLUORESCENT FUSION BASED HETEROLOGOUS PEPTIDE PRODUCTION

(71) Applicant: Stellenbosch University, Stellenbosch (ZA)

(72) Inventors: Anton Du Preez van Staden, Stellenbosch (ZA); Carine Smith, Stellenbosch (ZA); Dominic Nicholas, Stellenbosch (ZA); Leon Milner Theodore Dicks, Stellenbosch (ZA); Ross Rayne Vermeulen, Stellenbosch (ZA)

(73) Assignee: Stellenbosch University, Stellenbosch (ZA)

( * ) Notice: Subject to any disclaimer, the term of this patent is extended or adjusted under 35 U.S.C. 154(b) by 0 days.

(21) Appl. No.: 18/037,065

(22) PCT Filed: Nov. 16, 2021

(86) PCT No.: PCT/IB2021/060587
§ 371 (c)(1),
(2) Date: May 15, 2023

(87) PCT Pub. No.: WO2022/101885
PCT Pub. Date: May 19, 2022

(65) Prior Publication Data
US 2023/0392177 A1 Dec. 7, 2023

(30) Foreign Application Priority Data

Nov. 16, 2020 (ZA) .................................. 2020/07119

(51) Int. Cl.
*C12P 21/02* (2006.01)
*C07K 14/00* (2006.01)
*C12N 15/70* (2006.01)

(52) U.S. Cl.
CPC .............. *C12P 21/02* (2013.01); *C07K 14/00* (2013.01); *C12N 15/70* (2013.01); *C07K 2319/02* (2013.01); *C07K 2319/20* (2013.01); *C07K 2319/50* (2013.01); *C07K 2319/60* (2013.01)

(58) Field of Classification Search
None
See application file for complete search history.

(56) References Cited

FOREIGN PATENT DOCUMENTS

WO      2009149083 A2      12/2009

OTHER PUBLICATIONS

Chung et al. "An RNA thermometer in the chloroplast genome of Chlamydomonas facilitates temperature-controlled gene expression." Nucleic Acids Res. Oct. 19, 2023:gkad816 (Year: 2023).*
Hussein H et al. PLoS One. Apr. 1, 2019;14(4):e0214521 (Year: 2019).*
Neupert J et al. Nucleic Acids Res. Nov. 2008;36(19):e124 (Year: 2008).*
Su WW. Microb Cell Fact. Apr. 25, 2005;4(1):12 (Year: 2005).*
Zhang J et al. Sci Rep. Jun. 16, 2016;6:27973 (Year: 2016).*
Schmelcher M et al. Future Microbiol. Oct. 2012;7(10):1147-71 (Year: 2012).*
Van Reenen CA et al. J Appl Microbiol. Jun. 1998;84(6):1131-7 (Year: 1998).*
Dabora, R.L., et al., "Intracellular lytic enzyme systems and their use for disruption of Escherichia coli," Advances in Biochemical Engineering/Biotechnology, vol. 43, pp. 11-30 (1990).
International Search Report for International Application No. PCT/IB2021/060587, mailed Feb. 2, 2023 (6 pages).
Joshi, H., et al., "Novel method to rapidly and efficiently lyse Escherichia coli for the isolation of recombinant protein," Analytical Biochemistry, vol. 528, pp. 1-6 (2017).
Kamioka, T., et al., "Extraction of recombinant protein from Escherichia coli by using a novel cell autolysis activity of VanX," Analytical Biochemistry, vol. 439, No. 2, pp. 212-217 (2013).
Klinkert, B., et al., "Thermogenetic tools to monitor temperature-dependent gene expression in bacteria," Journal of Biotechnology, vol. 160, pp. 55-63 (2012).
Narberhaus, F., et al., "RNA thermometers," FEMS Microbiology Reviews, vol. 30, No. 1, pp. 3-16 (2006).
Sadler, F.W., et al., "RNA Thermometers for the PURExpress System," ACS Synthetic Bioloty, vol. 7, pp. 292-296 (2018).
Sevastsyanovich, Y., et al., "Exploitation of GFP fusion proteins and stress avoidance as a generic strategy for the production of high-quality recombinant proteins," FEMS Microbiology Letters, vol. 299, No. 1, pp. 86-94 (2009).
Snapp, E., "Design and Use of Fluorescent Fusion Proteins in Cell Biology," Current Protocols in Cell Biology, Unit 21.4, pp. 1-17 (2005).
Ehgartner, D., et al., "A novel method to recover inclusion body protein from recombinant E. coli fed-batch processes based on phage PhiX174-derived lysis protein E," Applied Microbiology and Biotechnology, vol. 101, pp. 5603-5614 (2017).
Loh, E., et al., "RNA Thermometers in Bacterial Pathogens," Microbiology Spectrum, vol. 6, No. 2, pp. 1-16 (2018).

* cited by examiner

Primary Examiner — Nancy J Leith
Assistant Examiner — Douglas Charles Ryan
(74) Attorney, Agent, or Firm — McNeill PLLC

(57) ABSTRACT

The present invention relates to a method of producing a heterologous polypeptide of interest in a host cell, wherein the method comprises expressing a fusion protein comprising the heterologous polypeptide of interest and a fluorescent fusion partner in a host cell modified to include a nucleic acid encoding a lytic protein operably linked to a promoter, wherein translation of the lytic protein is under control of an RNA thermometer. Also provided are E. coli cells which express the fusion protein and include a nucleic acid encoding a lytic protein operably linked to a promoter, wherein translation of the lytic protein regulated by an RNA thermometer.

33 Claims, 33 Drawing Sheets
Specification includes a Sequence Listing.

Fig. 3

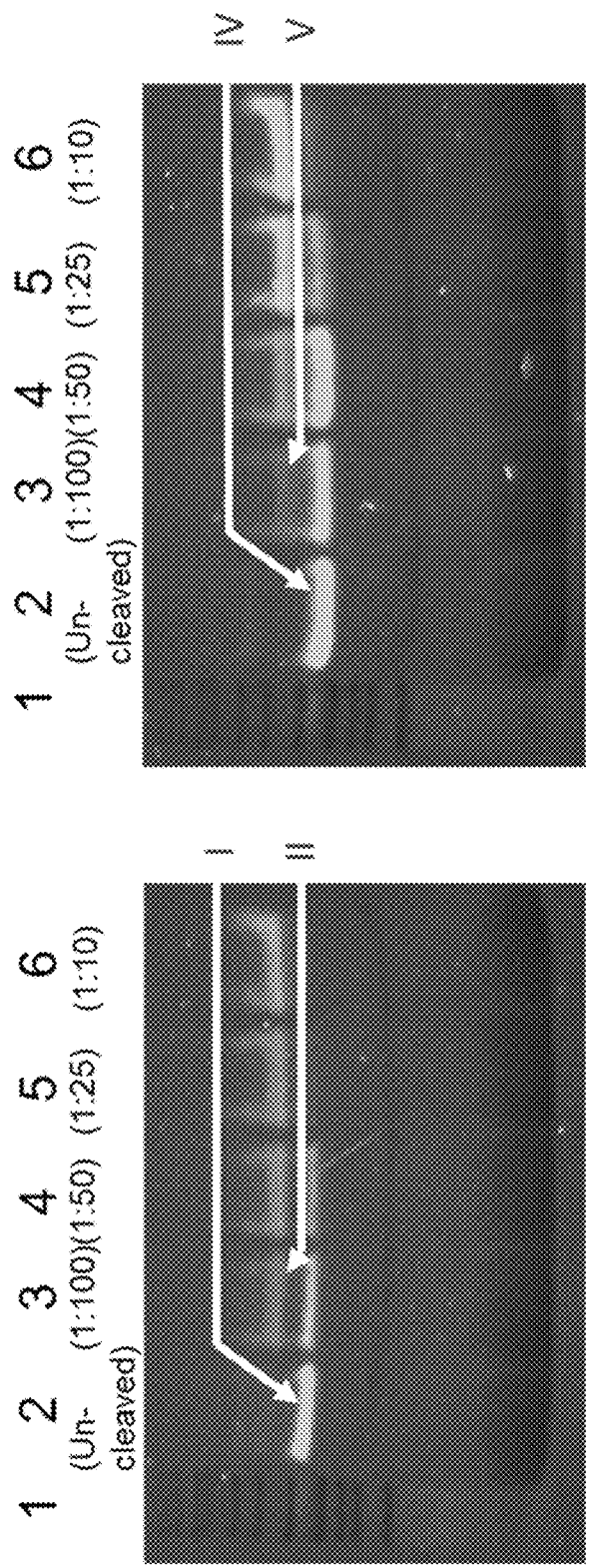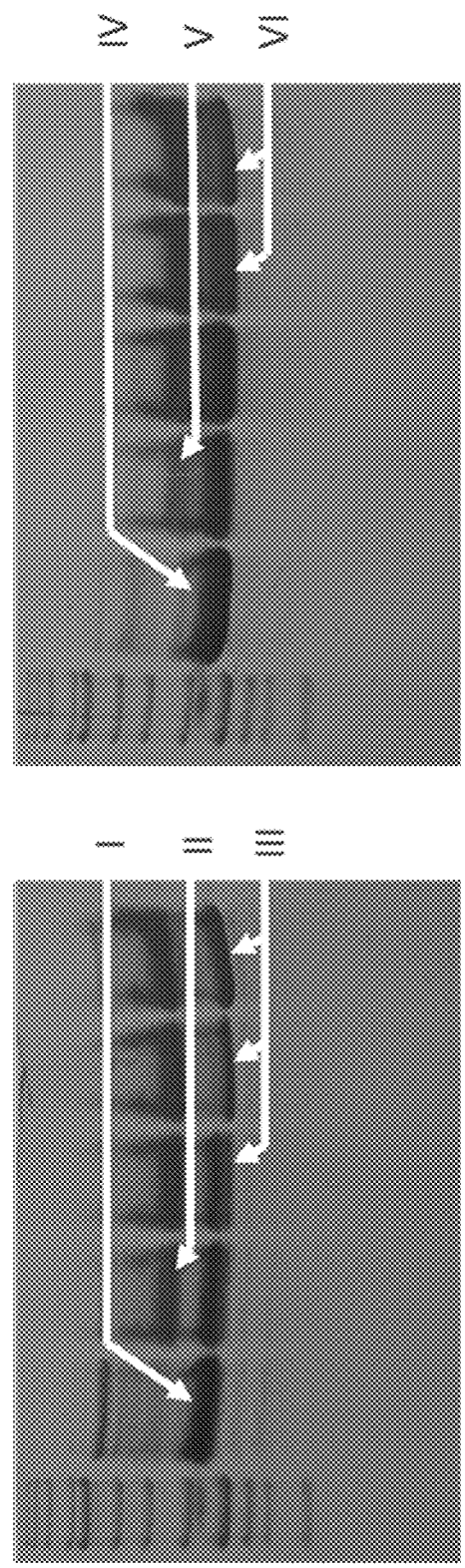
Fig. 15A Fig. 15B Fig. 15C Fig. 15D

SEQUENCE LISTING

```
<160> NUMBER OF SEQ ID NOS: 111

<210> SEQ ID NO 1
<211> LENGTH: 4
<212> TYPE: PRT
<213> ORGANISM: Artificial Sequence
<220> FEATURE:
<223> OTHER INFORMATION: WelQut Cleavage site amino acid sequence

<400> SEQUENCE: 1

Trp Glu Leu Gln
1

<210> SEQ ID NO 2
<211> LENGTH: 12
<212> TYPE: DNA
<213> ORGANISM: Artificial sequence
<220> FEATURE:
<223> OTHER INFORMATION: WelQut Cleavage site nucleotide sequence

<400> SEQUENCE: 2
tgggaactgc ag                                                           12

<210> SEQ ID NO 3
<211> LENGTH: 4
<212> TYPE: PRT
<213> ORGANISM: Artificial sequence
<220> FEATURE:
<223> OTHER INFORMATION: Thrombin/trypsin cleavage site amino acid
      sequence

<400> SEQUENCE: 3

Leu Val Pro Arg
1

<210> SEQ ID NO 4
<211> LENGTH: 12
<212> TYPE: DNA
<213> ORGANISM: Artificial sequence
<220> FEATURE:
<223> OTHER INFORMATION: Thrombin/trypsin cleavage site nucleotide
      sequence

<400> SEQUENCE: 4
ctagtaccac gc                                                           12

<210> SEQ ID NO 5
<211> LENGTH: 4
<212> TYPE: PRT
<213> ORGANISM: Artificial sequence
```

```
<220> FEATURE:
<223> OTHER INFORMATION: nisP/trypsin cleavage site amino acid sequence

<400> SEQUENCE: 5

Ala Ser Pro Arg
1

<210> SEQ ID NO 6
<211> LENGTH: 12
<212> TYPE: DNA
<213> ORGANISM: Artificial sequence
<220> FEATURE:
<223> OTHER INFORMATION: nisP/trypsin cleavage site nucleotide sequence

<400> SEQUENCE: 6
gcgagcccgc gc                                                           12

<210> SEQ ID NO 7
<211> LENGTH: 7
<212> TYPE: PRT
<213> ORGANISM: Artificial sequence
<220> FEATURE:
<223> OTHER INFORMATION: TEV cleavage site amino acid sequence

<400> SEQUENCE: 7

Glu Asn Leu Tyr Phe Gln Gly
1               5

<210> SEQ ID NO 8
<211> LENGTH: 21
<212> TYPE: DNA
<213> ORGANISM: Artificial sequence
<220> FEATURE:
<223> OTHER INFORMATION: TEV cleavage site nucleotide sequence

<400> SEQUENCE: 8
gaaaacttgt attttcaagg c                                                 21

<210> SEQ ID NO 9
<211> LENGTH: 4
<212> TYPE: PRT
<213> ORGANISM: Artificial sequence
<220> FEATURE:
<223> OTHER INFORMATION: Factor Xa cleavage site amino acid sequence

<400> SEQUENCE: 9

Ile Glu Gly Arg
1

<210> SEQ ID NO 10
<211> LENGTH: 12
<212> TYPE: DNA
<213> ORGANISM: Artificial sequence
<220> FEATURE:
<223> OTHER INFORMATION: Factor Xa cleavage site nucleotide sequence

<400> SEQUENCE: 10
attgaaggtc gt                                                           12

<210> SEQ ID NO 11
<211> LENGTH: 240
<212> TYPE: PRT
<213> ORGANISM: Artificial sequence
<220> FEATURE:
<223> OTHER INFORMATION: green fluorescent protein amino acid sequence
```

<400> SEQUENCE: 11

Met Ser Lys Gly Glu Glu Leu Phe Thr Gly Val Val Pro Ile Leu Val
1               5                   10                  15

Glu Leu Asp Gly Asp Val Asn Gly Tyr Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Ala Asn Phe Lys Thr Arg His Asn Ile Glu Asp Gly Gly Val
                165                 170                 175

Gln Leu Ala Asp His Tyr Gln Gln Asn Thr Pro Ile Gly Asp Asp Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys Thr Gly
225                 230                 235                 240

<210> SEQ ID NO 12
<211> LENGTH: 720
<212> TYPE: DNA
<213> ORGANISM: Artificial sequence
<220> FEATURE:
<223> OTHER INFORMATION: green fluorescent protein nucleotide sequence

<400> SEQUENCE: 12
atgagtaaag gagaagaact tttcactgga gttgtcccaa ttcttgttga attagatggt      60
gatgttaatg ggtacaaatt ttctgtcagt ggagagggtg aaggtgatgc aacatacgga     120
aaacttaccc ttaaatttat ttgcactact ggaaaactac ctgttccatg gccaacactt     180
gtcactactc tcacttatgg tgttcaatgc ttttcaagat atccagatca tatgaagcgg     240
cacgacttct tcaagagcgc catgcctgag ggatacgtgc aggagaggac catcttcttc     300
aaggacgacg gaactacaa gacacgtgct gaagtcaagt tgagggaga cccctcgtc       360 aacaggatcg agcttaaggg aatcgatttc aaggaggacg gaaacatcct cggccacaag     420
ttggaataca actacaactc ccacaacgta tacatcatgg ccgacaagca aaagaacggc     480
atcaaagcca acttcaagac ccgccacaac atcgaagacg gcggcgtgca actcgctgat     540
cattatcaac aaaatactcc aattggcgat gaccctgtcc ttttaccaga caaccattac     600

```
ctgtccacac aatctgccct ttcgaaagat cccaacgaaa agagagacca catggtcctt      660
cttgagtttg taacggctgc tgggattaca catggcatgg atgaactata caaaaccggt      720
```

<210> SEQ ID NO 13
<211> LENGTH: 227
<212> TYPE: PRT
<213> ORGANISM: Artificial sequence
<220> FEATURE:
<223> OTHER INFORMATION: mCherry amino acid sequence

<400> SEQUENCE: 13

```
Val Ala Ile Ile Lys Glu Phe Met Arg Phe Lys Val His Met Glu Gly
1               5                   10                  15

Ser Val Asn Gly His Glu Phe Glu Ile Glu Gly Glu Gly Glu Gly Arg
            20                  25                  30

Pro Tyr Glu Gly Thr Gln Thr Ala Lys Leu Lys Val Thr Lys Gly Gly
        35                  40                  45

Pro Leu Pro Phe Ala Trp Asp Ile Leu Ser Pro Gln Phe Met Tyr Gly
    50                  55                  60

Ser Lys Ala Tyr Val Lys His Pro Ala Asp Ile Pro Asp Tyr Leu Lys
65                  70                  75                  80

Leu Ser Phe Pro Glu Gly Phe Lys Trp Glu Arg Val Met Asn Phe Glu
                85                  90                  95

Asp Gly Gly Val Val Thr Val Thr Gln Asp Ser Ser Leu Gln Asp Gly
            100                 105                 110

Glu Phe Ile Tyr Lys Val Lys Leu Arg Gly Thr Asn Phe Pro Ser Asp
        115                 120                 125

Gly Pro Val Met Gln Lys Lys Thr Met Gly Trp Glu Ala Ser Ser Glu
    130                 135                 140

Arg Met Tyr Pro Glu Asp Gly Ala Leu Lys Gly Glu Ile Lys Gln Arg
145                 150                 155                 160

Leu Lys Leu Lys Asp Gly Gly His Tyr Asp Ala Glu Val Lys Thr Thr
                165                 170                 175

Tyr Lys Ala Lys Lys Pro Val Gln Leu Pro Gly Ala Tyr Asn Val Asn
            180                 185                 190

Ile Lys Leu Asp Ile Thr Ser His Asn Glu Asp Tyr Thr Ile Val Glu
        195                 200                 205

Gln Tyr Glu Arg Ala Glu Gly Arg His Ser Thr Gly Gly Met Asp Glu
    210                 215                 220

Leu Tyr Lys
225
```

<210> SEQ ID NO 14
<211> LENGTH: 681
<212> TYPE: DNA
<213> ORGANISM: Artificial sequence
<220> FEATURE:
<223> OTHER INFORMATION: mCherry nucleotide sequence

<400> SEQUENCE: 14

```
gtggcaatca tcaaagaatt tatgcggttt aaagtacata tggaaggtag tgtgaatggt       60
catgaatttg aaattgaagg tgaaggagaa ggtagaccat atgaaggaac gcaaaccgcg      120
aaattgaaag ttactaaagg tggaccatta ccttttgcat gggatatctt atctccacaa      180
tttatgtatg gatcaaaagc atatgtaaaa catccagcag atatccctga ttatttaaaa      240
ttaagttttc ctgaaggttt taaatgggaa cgggttatga attttgaaga tggtggagtt      300
```

```
gtaactgtaa cacaagatag ttctttacaa gatggagaat ttatctataa agtcaaattg    360
cgtggaacga attttccatc tgatggtcct gtgatgcaaa agaaaactat gggttgggaa    420
gctagtagtg aacgtatgta tccagaagat ggagcattaa aaggtgaaat caaacaaaga    480
ttaaaattga aagatggtgg acattatgat gcggaagtta aaactacata taaagccaaa    540
aaaccagtcc aattacctgg tgcttataat gtgaatatca aattggatat cacgagtcat    600
aatgaagatt ataccattgt cgaacaatat gaaagagcgg aaggaagaca ttctacaggt    660
ggtatggatg aattatataa a                                              681
```

<210> SEQ ID NO 15
<211> LENGTH: 161
<212> TYPE: PRT
<213> ORGANISM: Artificial sequence
<220> FEATURE:
<223> OTHER INFORMATION: GpR lytic protein amino acid sequence

<400> SEQUENCE: 15

```
Met Ala Asp Leu Val Glu Ile Asn Asn Gln Arg Lys Ala Phe Leu Asp
1               5                   10                  15

Met Leu Ala Trp Ser Glu Gly Thr Asp Asn Gly Arg Gln Lys Thr Arg
            20                  25                  30

Asn His Gly Tyr Asp Val Ile Val Gly Gly Glu Leu Phe Thr Asp Tyr
        35                  40                  45

Ser Asp His Pro Arg Lys Leu Val Thr Leu Asn Pro Lys Leu Lys Ser
    50                  55                  60

Thr Gly Ala Gly Arg Tyr Gln Leu Leu Ser Arg Trp Trp Asp Ala Tyr
65                  70                  75                  80

Arg Lys Gln Leu Gly Leu Lys Asp Phe Ser Pro Lys Ser Gln Asp Ala
                85                  90                  95

Val Ala Leu Gln Gln Ile Lys Glu Arg Gly Ala Leu Pro Met Ile Asp
            100                 105                 110

Arg Gly Asp Ile Arg Gln Ala Ile Asp Arg Cys Ser Asn Ile Trp Ala
        115                 120                 125

Ser Leu Pro Gly Ala Gly Tyr Gly Gln Phe Glu His Lys Ala Asp Ser
    130                 135                 140

Leu Ile Ala Lys Phe Lys Glu Ala Gly Gly Thr Val Arg Glu Ile Asp
145                 150                 155                 160

Val
```

<210> SEQ ID NO 16
<211> LENGTH: 483
<212> TYPE: DNA
<213> ORGANISM: Artificial sequence
<220> FEATURE:
<223> OTHER INFORMATION: GpR lytic protein nucleotide sequence

<400> SEQUENCE: 16

```
atggcagatc tggtagaaat caataatcaa cgtaaggcgt tcctcgatat gctggcgtgg    60
tcggagggaa ctgataacgg acgtcagaaa accagaaatc atggttatga cgtcattgta    120
ggcggagagc tatttactga ttactccgat caccctcgca aacttgtcac gctaaaccca    180
aaactcaaat caacaggcgc cggacgctac cagcttcttt cccgttggtg ggatgcctac    240
cgcaagcagc ttggcctgaa agacttctct ccgaaaagtc aggacgctgt ggcattgcag    300
cagattaagg agcgtggcgc tttacctatg attgatcgtg gtgatatccg tcaggcaatc    360
```

```
gaccgttgca gcaatatctg ggcttcactg ccgggcgctg gttatggtca gttcgagcat    420
aaggctgaca gcctgattgc aaaattcaaa gaagcgggcg aacggtcag agagattgat     480 gta                                                                  483
```

```
<210> SEQ ID NO 17
<211> LENGTH: 167
<212> TYPE: PRT
<213> ORGANISM: Artificial sequence
<220> FEATURE:
<223> OTHER INFORMATION: GpE lytic protein amino acid sequence

<400> SEQUENCE: 17
```

Met Ala Asp Leu Asn Ile Phe Glu Met Leu Arg Ile Asp Glu Arg Leu
1               5                   10                  15

Arg Leu Lys Ile Tyr Lys Asp Thr Glu Gly Tyr Tyr Thr Ile Gly Ile
            20                  25                  30

Gly His Leu Leu Thr Lys Ser Pro Ser Leu Asn Ala Ala Lys Ser Glu
        35                  40                  45

Leu Asp Lys Ala Ile Gly Arg Asn Cys Asn Gly Val Ile Thr Lys Asp
    50                  55                  60

Glu Ala Glu Lys Leu Phe Asn Gln Asp Val Ala Ala Val Arg Gly
65                  70                  75                  80

Ile Leu Arg Asn Ala Lys Leu Lys Pro Val Tyr Asp Ser Leu Asp Ala
                85                  90                  95

Val Arg Arg Cys Ala Leu Ile Asn Met Val Phe Gln Met Gly Glu Thr
            100                 105                 110

Gly Val Ala Gly Phe Thr Asn Ser Leu Arg Met Leu Gln Gln Lys Arg
        115                 120                 125

Trp Asp Glu Ala Ala Val Asn Leu Ala Lys Ser Ile Trp Tyr Asn Gln
    130                 135                 140

Thr Pro Asn Arg Ala Lys Arg Val Ile Thr Thr Phe Arg Thr Gly Thr
145                 150                 155                 160

Trp Asp Ala Tyr Lys Asn Leu
                165

```
<210> SEQ ID NO 18
<211> LENGTH: 501
<212> TYPE: DNA
<213> ORGANISM: Artificial sequence
<220> FEATURE:
<223> OTHER INFORMATION: GpE lytic protein nucleotide sequence

<400> SEQUENCE: 18
```

```
atggcagatc tgaatatttt tgaaatgctg cgtatagatg aaggtcttag acttaaaatc    60
tataaagaca cagaaggcta ttacactatt ggcatcggtc atttgcttac aaaaagtcca   120
tcacttagtg ttgctaaatc tgaattagat aaagctattg gacgtaattg caatggtgta   180
attacaaaag atgaggctga aaaactcttt aatcaggatt tgatgctgc tgttcgcgga   240 attctgagaa atgctaaatt aaaaccggtt tatgattctc ttgatgcggt cgtcgttgt   300 gcattgatta atatggtctt ccaaatggga gaaccggtg tggcaggatt tactaactct   360
ttacgtatgc ttcaacaaaa acgctgggat gaagcagcag ttaacttagc taaaagtaga   420
tggtataatc aaacacctaa tcgcgcaaaa cgagtcatta caacgtttag aactggcact   480
tgggacgcat ataaaaatct g                                              501
```

```
<210> SEQ ID NO 19
```

```
<211> LENGTH: 25
<212> TYPE: RNA
<213> ORGANISM: Artificial sequence
<220> FEATURE:
<223> OTHER INFORMATION: RNA thermometer 1

<400> SEQUENCE: 19
uaguucuccu ucagaaggag auaua                                           25

<210> SEQ ID NO 20
<211> LENGTH: 130
<212> TYPE: RNA
<213> ORGANISM: Artificial sequence
<220> FEATURE:
<223> OTHER INFORMATION: RNA thermometer 2

<400> SEQUENCE: 20
uguaaaaaac aucauuuagc gugacuuucu uucaacagcu aacaauuguu guuacugccu     60
aauguuuuua ggguauuuua aaaagggcg auaaaaaacg auuggggau gagacaugaa     120 cgcucaagca                                                           130

<210> SEQ ID NO 21
<211> LENGTH: 89
<212> TYPE: RNA
<213> ORGANISM: Artificial sequence
<220> FEATURE:
<223> OTHER INFORMATION: RNA thermometer 3

<400> SEQUENCE: 21
ggccacuuua gucugugguu acuguauuag guauuguuau aacaaucugg augguuuuua   60
ugaauaagac auuacugguc ucuucuuua                                      89

<210> SEQ ID NO 22
<211> LENGTH: 112
<212> TYPE: RNA
<213> ORGANISM: Artificial sequence
<220> FEATURE:
<223> OTHER INFORMATION: RNA thermometer 4

<400> SEQUENCE: 22
uguguuuuuu guaaguucua uuaaauacau caguuuacag caaugaauuc accauugugc   60
aucgucaaua aaaggagugu uuaugaaaaa ucaauggcaa caucaauauu uu           112

<210> SEQ ID NO 23
<211> LENGTH: 46
<212> TYPE: RNA
<213> ORGANISM: Artificial sequence
<220> FEATURE:
<223> OTHER INFORMATION: RNA thermometer 5

<400> SEQUENCE: 23
acagcaauuu ugcguuaccu guuaaucgag auugaaacac augaaa                   46

<210> SEQ ID NO 24
<211> LENGTH: 240
<212> TYPE: RNA
<213> ORGANISM: Artificial sequence
<220> FEATURE:
<223> OTHER INFORMATION: RNA thermometer 6

<400> SEQUENCE: 24
ggcgccacgg uuugacguac agaccauuaa agcaguguag uaaggcaagu cccuucaaga   60
guuaucguug auaccccucg uagugcacau uccuuuaacg cuucaaaauc uguaaagcac   120
```

```
gccauaucgc cgaaaggcac acuuaauuau uaaagguaau acacuaugug cgguaaaaug    180
acugguaucg uaaaauggu caacgcugac aaaggcuucg gcuucaucac uccugacgau     240
```

<210> SEQ ID NO 25
<211> LENGTH: 46
<212> TYPE: RNA
<213> ORGANISM: Artificial sequence
<220> FEATURE:
<223> OTHER INFORMATION: RNA thermometer 7

<400> SEQUENCE: 25

```
acagcaauuu ugcguuaucu guuaaucgag acugaaauac augaaa                    46
```

<210> SEQ ID NO 26
<211> LENGTH: 50
<212> TYPE: RNA
<213> ORGANISM: Artificial sequence
<220> FEATURE:
<223> OTHER INFORMATION: RNA thermometer 8

<400> SEQUENCE: 26

```
auucaagggu aaucaauucc uuccacacau caggaguuaa cauuaugucu                50
```

<210> SEQ ID NO 27
<211> LENGTH: 110
<212> TYPE: RNA
<213> ORGANISM: Artificial sequence
<220> FEATURE:
<223> OTHER INFORMATION: RNA thermometer 9

<400> SEQUENCE: 27

```
ggccuaauua uagcacuuaa ucgaaauaaa uuuaugagua cguagaguau aauuaguauu     60
cuucuuucca acuuccuuau acuuauauac uuauagauuc uaaaaucaug               110
```

<210> SEQ ID NO 28
<211> LENGTH: 301
<212> TYPE: PRT
<213> ORGANISM: Artificial sequence
<220> FEATURE:
<223> OTHER INFORMATION: GFPNisin (ASPR) amino acid sequence

<400> SEQUENCE: 28

Met Ser Lys Gly Glu Glu Leu Phe Thr Gly Val Val Pro Ile Leu Val
1               5                   10                  15

Glu Leu Asp Gly Asp Val Asn Gly Tyr Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Ala Asn Phe Lys Thr Arg His Asn Ile Glu Asp Gly Gly Val
            165                 170                 175

Gln Leu Ala Asp His Tyr Gln Gln Asn Thr Pro Ile Gly Asp Asp Pro
        180                 185                 190

Val Leu Leu Pro Asp Asn His Tyr Leu Ser Thr Gln Ser Ala Leu Ser
    195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys Thr Gly
225                 230                 235                 240

Trp Glu Leu Gln Met Ser Thr Lys Asp Phe Asn Leu Asp Leu Val Ser
                245                 250                 255

Val Ser Lys Lys Asp Ser Gly Ala Ser Pro Arg Ile Thr Ser Ile Ser
            260                 265                 270

Leu Cys Thr Pro Gly Cys Lys Thr Gly Ala Leu Met Gly Cys Asn Met
        275                 280                 285

Lys Thr Ala Thr Cys His Cys Ser Ile His Val Ser Lys
        290                 295                 300

<210> SEQ ID NO 29
<211> LENGTH: 903
<212> TYPE: DNA
<213> ORGANISM: Artificial sequence
<220> FEATURE:
<223> OTHER INFORMATION: GFPNisin (ASPR) nucleotide sequence

<400> SEQUENCE: 29
atgagtaaag gagaagaact tttcactgga gttgtcccaa ttcttgttga attagatggt      60
gatgttaatg ggtacaaatt ttctgtcagt ggagagggtg aaggtgatgc aacatacgga     120
aaacttaccc ttaaatttat ttgcactact ggaaaactac ctgttccatg gccaacactt     180
gtcactactc tcacttatgg tgttcaatgc ttttcaagat atccagatca tatgaagcgg     240
cacgacttct tcaagagcgc catgcctgag ggatacgtgc aggagaggac catcttcttc     300
aaggacgacg ggaactacaa gacacgtgct gaagtcaagt ttgagggaga caccctcgtc     360
aacaggatcg agcttaaggg aatcgatttc aaggaggacg gaaacatcct cggcacacaa     420
ttggaataca actacaactc ccacaacgta tacatcatgg ccgacaagca aaagaacggc     480
atcaaagcca acttcaagac ccgccacaac atcgaagacg gcggcgtgca actcgctgat     540
cattatcaac aaaatactcc aattggcgat gaccctgtcc ttttaccaga caaccattac     600
ctgtccacac aatctgccct ttcgaaagat cccaacgaaa agagagacca catggtcctt     660
cttgagtttg taacggctgc tgggattaca catggcatgg atgaactata caaaaccggt     720
tgggaactgc agatgagtac aaaagatttt aacttggatt tggtatctgt ttcgaagaaa     780
gattcaggtg catcaccacg cattacaagt atttcgctat gtacacccgg ttgtaaaaca     840
ggagctctga tgggttgtaa catgaaaaca gcaacttgtc attgtagtat tcacgtaagc     900
aaa                                                                    903

<210> SEQ ID NO 30
<211> LENGTH: 315
<212> TYPE: PRT
<213> ORGANISM: Artificial sequence
<220> FEATURE:

<223> OTHER INFORMATION: GFPNisin (AVPR) amino acid sequence

<400> SEQUENCE: 30

Met Gly Ser Ser His His His His His His Ser Gln Asp Pro Met Ser
1               5                   10                  15

Lys Gly Glu Glu Leu Phe Thr Gly Val Val Pro Ile Leu Val Glu Leu
            20                  25                  30

Asp Gly Asp Val Asn Gly Tyr Lys Phe Ser Val Ser Gly Glu Gly Glu
        35                  40                  45

Gly Asp Ala Thr Tyr Gly Lys Leu Thr Leu Lys Phe Ile Cys Thr Thr
    50                  55                  60

Gly Lys Leu Pro Val Pro Trp Pro Thr Leu Val Thr Thr Leu Thr Tyr
65                  70                  75                  80

Gly Val Gln Cys Phe Ser Arg Tyr Pro Asp His Met Lys Arg His Asp
                85                  90                  95

Phe Phe Lys Ser Ala Met Pro Glu Gly Tyr Val Gln Glu Arg Thr Ile
            100                 105                 110

Phe Phe Lys Asp Asp Gly Asn Tyr Lys Thr Arg Ala Glu Val Lys Phe
        115                 120                 125

Glu Gly Asp Thr Leu Val Asn Arg Ile Glu Leu Lys Gly Ile Asp Phe
    130                 135                 140

Lys Glu Asp Gly Asn Ile Leu Gly His Lys Leu Glu Tyr Asn Tyr Asn
145                 150                 155                 160

Ser His Asn Val Tyr Ile Met Ala Asp Lys Gln Lys Asn Gly Ile Lys
                165                 170                 175

Ala Asn Phe Lys Thr Arg His Asn Ile Glu Asp Gly Gly Val Gln Leu
            180                 185                 190

Ala Asp His Tyr Gln Gln Asn Thr Pro Ile Gly Asp Asp Pro Val Leu
        195                 200                 205

Leu Pro Asp Asn His Tyr Leu Ser Thr Gln Ser Ala Leu Ser Lys Asp
    210                 215                 220

Pro Asn Glu Lys Arg Asp His Met Val Leu Leu Glu Phe Val Thr Ala
225                 230                 235                 240

Ala Gly Ile Thr His Gly Met Asp Glu Leu Tyr Lys Thr Gly Trp Glu
                245                 250                 255

Leu Gln Met Ser Thr Lys Asp Phe Asn Leu Asp Leu Val Ser Val Ser
            260                 265                 270

Lys Lys Asp Ser Gly Ala Val Pro Arg Ile Thr Ser Ile Ser Leu Cys
        275                 280                 285

Thr Pro Gly Cys Lys Thr Gly Ala Leu Met Gly Cys Asn Met Lys Thr
    290                 295                 300

Ala Thr Cys His Cys Ser Ile His Val Ser Lys
305                 310                 315

<210> SEQ ID NO 31
<211> LENGTH: 945
<212> TYPE: DNA
<213> ORGANISM: Artificial sequence
<220> FEATURE:
<223> OTHER INFORMATION: GFPNisin (AVPR) nucleotide sequence

<400> SEQUENCE: 31
atgggcagca gccatcacca tcatcaccac agccaggatc cgatgagtaa aggagaagaa      60
cttttcactg gagttgtccc aattcttgtt gaattagatg gtgatgttaa tgggtacaaa     120
ttttctgtca gtggagaggg tgaaggtgat gcaacatacg gaaaacttac ccttaaattt     180

```
atttgcacta ctggaaaact acctgttcca tggccaacac ttgtcactac tctcacttat    240
ggtgttcaat gctttttcaag atatccagat catatgaagc ggcacgactt cttcaagagc   300
gccatgcctg agggatacgt gcaggagagg accatcttct tcaaggacga cgggaactac   360
aagacacgtg ctgaagtcaa gtttgaggga gacaccctcg tcaacaggat cgagcttaag   420
ggaatcgatt tcaaggagga cggaaacatc ctcggccaca agttggaata caactacaac   480
tcccacaacg tatacatcat ggccgacaag caaaagaacg gcatcaaagc caacttcaag   540
acccgccaca acatcgaaga cggcggcgtg caactcgctg atcattatca acaaaatact   600
ccaattggcg atgaccctgt cctttttacca gacaaccatt acctgtccac acaatctgcc   660
ctttcgaaag atcccaacga aaagagagac cacatggtcc ttcttgagtt tgtaacggct   720
gctgggatta cacatggcat ggatgaacta tacaaaaccg gttgggaact gcagatgagt   780
acaaaagatt ttaacttgga tttggtatct gtttcgaaga aagattcagg tgcagtacca   840
cgcattacaa gtatttcgct atgtacaccc ggttgtaaaa caggagctct gatgggttgt   900
aacatgaaaa cagcaacttg tcattgtagt attcacgtaa gcaaa                   945
```

<210> SEQ ID NO 32
<211> LENGTH: 301
<212> TYPE: PRT
<213> ORGANISM: Artificial sequence
<220> FEATURE:
<223> OTHER INFORMATION: GFPMunX amino acid sequence

<400> SEQUENCE: 32

```
Met Gly Ser Ser His His His His His His Ser Gln Asp Pro Met Ser
1               5                   10                  15

Lys Gly Glu Glu Leu Phe Thr Gly Val Val Pro Ile Leu Val Glu Leu
            20                  25                  30

Asp Gly Asp Val Asn Gly Tyr Lys Phe Ser Val Ser Gly Glu Gly Glu
        35                  40                  45

Gly Asp Ala Thr Tyr Gly Lys Leu Thr Leu Lys Phe Ile Cys Thr Thr
    50                  55                  60

Gly Lys Leu Pro Val Pro Trp Pro Thr Leu Val Thr Thr Leu Thr Tyr
65                  70                  75                  80

Gly Val Gln Cys Phe Ser Arg Tyr Pro Asp His Met Lys Arg His Asp
                85                  90                  95

Phe Phe Lys Ser Ala Met Pro Glu Gly Tyr Val Gln Glu Arg Thr Ile
            100                 105                 110

Phe Phe Lys Asp Asp Gly Asn Tyr Lys Thr Arg Ala Glu Val Lys Phe
        115                 120                 125

Glu Gly Asp Thr Leu Val Asn Arg Ile Glu Leu Lys Gly Ile Asp Phe
    130                 135                 140

Lys Glu Asp Gly Asn Ile Leu Gly His Lys Leu Glu Tyr Asn Tyr Asn
145                 150                 155                 160

Ser His Asn Val Tyr Ile Met Ala Asp Lys Gln Lys Asn Gly Ile Lys
                165                 170                 175

Ala Asn Phe Lys Thr Arg His Asn Ile Glu Asp Gly Gly Val Gln Leu
            180                 185                 190

Ala Asp His Tyr Gln Gln Asn Thr Pro Ile Gly Asp Asp Pro Val Leu
        195                 200                 205

Leu Pro Asp Asn His Tyr Leu Ser Thr Gln Ser Ala Leu Ser Lys Asp
    210                 215                 220
```

```
Pro Asn Glu Lys Arg Asp His Met Val Leu Leu Glu Phe Val Thr Ala
225                 230                 235                 240

Ala Gly Ile Thr His Gly Met Asp Glu Leu Tyr Lys Thr Gly Trp Glu
            245                 250                 255

Leu Gln Lys Tyr Tyr Gly Asn Gly Val Ser Cys Asn Lys Lys Gly Cys
        260                 265                 270

Ser Val Asp Trp Gly Lys Ala Ile Gly Ile Ile Gly Asn Asn Ser Ala
    275                 280                 285

Ala Asn Leu Ala Thr Gly Gly Ala Ala Gly Trp Lys Ser
    290                 295                 300

<210> SEQ ID NO 33
<211> LENGTH: 903
<212> TYPE: DNA
<213> ORGANISM: Artificial sequence
<220> FEATURE:
<223> OTHER INFORMATION: GFPMunX nucleotide sequence

<400> SEQUENCE: 33
atgggcagca gccatcacca tcatcaccac agccaggatc cgatgagtaa aggagaagaa        60
cttttcactg gagttgtccc aattcttgtt gaattagatg gtgatgttaa tgggtacaaa       120
ttttctgtca gtggagaggg tgaaggtgat gcaacatacg gaaaacttac ccttaaattt       180
atttgcacta ctggaaaact acctgttcca tggccaacac ttgtcactac tctcacttat       240
ggtgttcaat gcttttcaag atatccagat catatgaagc ggcacgactt cttcaagagc       300
gccatgcctg agggatacgt gcaggagagg accatcttct tcaaggacga cgggaactac       360
aagacacgtg ctgaagtcaa gtttgaggga gacacccctcg tcaacaggat cgagcttaag       420
ggaatcgatt tcaaggagga cggaaacatc ctcggccaca gttggaata caactacaac       480 tcccacaacg tatacatcat ggccgacaag caaaagaacg gcatcaaagc caacttcaag       540
acccgccaca catcgaagac ggcggcgtg caactcgctg atcattatca acaaaatact       600
ccaattggcg atgaccctgt ccttttacca gacaaccatt acctgtccac acaatctgcc       660
ctttcgaaag atcccaacga aaagagagac cacatggtcc ttcttgagtt tgtaacggct       720
gctgggatta cacatggcat ggatgaacta tacaaaaccg gttgggaact gcagaaatac       780
tacggtaatg gagtctcatg taataaaaaa gggtgcagtg ttgattgggg aaaagctatt       840
ggcattattg gaaataattc tgctgcgaat ttagctactg gtggagcagc tggttggaaa       900
agt                                                                     903

<210> SEQ ID NO 34
<211> LENGTH: 295
<212> TYPE: PRT
<213> ORGANISM: Artificial sequence
<220> FEATURE:
<223> OTHER INFORMATION: GFPPlantX amino acid sequence

<400> SEQUENCE: 34

Met Gly Ser Ser His His His His His His Ser Gln Asp Pro Met Ser
1               5                   10                  15

Lys Gly Glu Glu Leu Phe Thr Gly Val Val Pro Ile Leu Val Glu Leu
            20                  25                  30

Asp Gly Asp Val Asn Gly Tyr Lys Phe Ser Val Ser Gly Glu Gly Glu
        35                  40                  45

Gly Asp Ala Thr Tyr Gly Lys Leu Thr Leu Lys Phe Ile Cys Thr Thr
    50                  55                  60
```

```
Gly Lys Leu Pro Val Pro Trp Pro Thr Leu Val Thr Thr Leu Thr Tyr
 65                  70                  75                  80

Gly Val Gln Cys Phe Ser Arg Tyr Pro Asp His Met Lys Arg His Asp
                 85                  90                  95

Phe Phe Lys Ser Ala Met Pro Glu Gly Tyr Val Gln Glu Arg Thr Ile
            100                 105                 110

Phe Phe Lys Asp Asp Gly Asn Tyr Lys Thr Arg Ala Glu Val Lys Phe
        115                 120                 125

Glu Gly Asp Thr Leu Val Asn Arg Ile Glu Leu Lys Gly Ile Asp Phe
130                 135                 140

Lys Glu Asp Gly Asn Ile Leu Gly His Lys Leu Glu Tyr Asn Tyr Asn
145                 150                 155                 160

Ser His Asn Val Tyr Ile Met Ala Asp Lys Gln Lys Asn Gly Ile Lys
                165                 170                 175

Ala Asn Phe Lys Thr Arg His Asn Ile Glu Asp Gly Gly Val Gln Leu
            180                 185                 190

Ala Asp His Tyr Gln Gln Asn Thr Pro Ile Gly Asp Asp Pro Val Leu
        195                 200                 205

Leu Pro Asp Asn His Tyr Leu Ser Thr Gln Ser Ala Leu Ser Lys Asp
210                 215                 220

Pro Asn Glu Lys Arg Asp His Met Val Leu Leu Glu Phe Val Thr Ala
225                 230                 235                 240

Ala Gly Ile Thr His Gly Met Asp Glu Leu Tyr Lys Thr Gly Trp Glu
                245                 250                 255

Leu Gln Lys Tyr Tyr Gly Asn Gly Val Thr Cys Gly Lys His Ser Cys
            260                 265                 270

Ser Val Asn Trp Gly Gln Ala Phe Ser Cys Ser Val Ser His Leu Ala
        275                 280                 285

Asn Phe Gly His Gly Lys Cys
290                 295

<210> SEQ ID NO 35
<211> LENGTH: 885
<212> TYPE: DNA
<213> ORGANISM: Artificial sequence
<220> FEATURE:
<223> OTHER INFORMATION: GFPPlantX nucleotide sequence

<400> SEQUENCE: 35
atgggcagca gccatcacca tcatcaccac agccaggatc cgatgagtaa aggagaagaa     60
cttttcactg gagttgtccc aattcttgtt gaattagatg gtgatgttaa tgggtacaaa    120
ttttctgtca gtggagaggg tgaaggtgat gcaacatacg gaaaacttac ccttaaattt    180
atttgcacta ctggaaaact acctgttcca tggccaacac ttgtcactac tctcacttat    240
ggtgttcaat gcttttcaag atatccagat catatgaagc ggcacgactt cttcaagagc    300
gccatgcctg agggatacgt gcaggagagg accatcttct tcaaggacga cgggaactac    360
aagacacgtg ctgaagtcaa gtttgaggga gacacccctcg tcaacaggat cgagcttaag    420
ggaatcgatt tcaaggagga cggaaacatc ctcggccaca gttggaata caactacaac    480 tcccacaacg tatacatcat ggccgacaag caaaagaacg gcatcaaagc caacttcaag    540
acccgccaca acatcgaaga cggcggcgtg caactcgctg atcattatca acaaaatact    600
ccaattggcg atgaccctgt ccttttacca gacaaccatt acctgtccac acaatctgcc    660
ctttcgaaag atcccaacga aaagagagac cacatggtcc ttcttgagtt tgtaacggct    720
```

| | |
|---|---|
| gctgggatta cacatggcat ggatgaacta tacaaaaccg gttgggaact gcagaaatac | 780 |
| tatggtaatg gggttacttg tggtaaacat tcctgctctg ttaactgggg ccaagcattt | 840 |
| tcttgtagtg tgtcacattt agctaacttc ggtcatggaa agtgc | 885 |

<210> SEQ ID NO 36
<211> LENGTH: 3829
<212> TYPE: DNA
<213> ORGANISM: Artificial sequence
<220> FEATURE:
<223> OTHER INFORMATION: pTAP (RNA thermometer backbone vector)
      nucleotide sequence

<400> SEQUENCE: 36

| | |
|---|---|
| ggggaattgt gagcggataa caattcccct gtagaaataa ttttgtttaa ctttaataag | 60 |
| gagatatacc atgggcagca gccatcacca tcatcaccac agccaggatc cgaattcgag | 120 |
| ctcggcgcgc ctgcaggtcg acaagcttgc ggccgcataa tgcttaagtc gaacagaaag | 180 |
| taatcgtatt gtacacggcc gcataatcga aattaatacg actcactata ggggaattgt | 240 |
| gagcggataa caattcccca tcttagtata ttagttctcc ttcagaagga gatatacata | 300 |
| tggcagatct caattggata tcggccggcc acgcgatcgc tgacgtcggt accctcgagt | 360 |
| ctggtaaaga aaccgctgct gcgaaatttg aacgccagca catggactcg tctactagcg | 420 |
| cagcttaatt aacctaggct gctgccaccg ctgagcaata actagcataa ccccttgggg | 480 |
| cctctaaacg ggtcttgagg ggttttttgc tgaaacctca ggcatttgag aagcacacgg | 540 |
| tcacactgct tccggtagtc aataaaccgg taaaccagca atagacataa gcggctattt | 600 |
| aacgaccctg ccctgaaccg acgacaagct gacgaccggg tctccgcaag tggcactttt | 660 |
| cggggaaatg tgcgcggaac ccctatttgt ttatttttct aaatacattc aaatatgtat | 720 |
| ccgctcatga attaattctt agaaaaactc atcgagcatc aaatgaaact gcaatttatt | 780 |
| catatcagga ttatcaatac catatttttg aaaaagccgt ttctgtaatg aaggagaaaa | 840 |
| ctcaccgagg cagttccata ggatggcaag atcctggtat cggtctgcga ttccgactcg | 900 |
| tccaacatca atacaaccta ttaatttccc ctcgtcaaaa ataaggttat caagtgagaa | 960 |
| atcaccatga gtgacgactg aatccggtga gaatggcaaa agtttatgca tttctttcca | 1020 |
| gacttgttca acaggccagc cattacgctc gtcatcaaaa tcactcgcat caaccaaacc | 1080 |
| gttattcatt cgtgattgcg cctgagcgag acgaaatacg cggtcgctgt taaaaggaca | 1140 |
| attacaaaca ggaatcgaat gcaaccggcg caggaacact gccagcgcat caacaatatt | 1200 |
| ttcacctgaa tcaggatatt cttctaatac ctggaatgct gttttcccgg ggatcgcagt | 1260 |
| ggtgagtaac catgcatcat caggagtacg gataaaatgc ttgatggtcg aagaggcat | 1320 |
| aaattccgtc agccagttta gtctgaccat ctcatctgta acatcattgg caacgctacc | 1380 |
| tttgccatgt ttcagaaaca actctggcgc atcgggcttc ccatacaatc gatagattgt | 1440 |
| cgcacctgat tgcccgacat tatcgcgagc ccatttatac ccatataaat cagcatccat | 1500 |
| gttggaattt aatcgcggcc tagagcaaga cgtttcccgt tgaatatggc tcatactctt | 1560 |
| cctttttcaa tattattgaa gcatttatca gggttattgt ctcatgagcg gatacatatt | 1620 |
| tgaatgtatt tagaaaaata acaaataggg catgcagcgc tcttccgctt cctcgctcac | 1680 |
| tgactcgcta cgctcggtcg ttcgactgcg gcgagcggtg tcagctcact caaaagcggt | 1740 |
| aatacggtta tccacagaat caggggataa agccggaaag aacatgtgag caaaaagcaa | 1800 |
| agcaccggaa gaagccaacg ccgcaggcgt ttttccatag gctccgcccc cctgacgagc | 1860 |

-continued

```
atcacaaaaa tcgacgctca agccagaggt ggcgaaaccc gacaggacta taaagatacc    1920
aggcgtttcc ccctggaagc tccctcgtgc gctctcctgt tccgaccctg ccgcttaccg    1980
gataccctgtc cgcctttctc ccttcgggaa gcgtggcgct ttctcatagc tcacgctgtt   2040
ggtatctcag ttcggtgtag gtcgttcgct ccaagctggg ctgtgtgcac gaaccccccg    2100
ttcagcccga ccgctgcgcc ttatccggta actatcgtct tgagtccaac ccggtaagac    2160
acgacttatc gccactggca gcagccattg gtaactgatt tagaggactt tgtcttgaag    2220
ttatgcacct gttaaggcta aactgaaaga acagattttg gtgagtgcgg tcctccaacc    2280
cacttacctt ggttcaaaga gttggtagct cagcgaacct tgagaaaacc accgttggta    2340
gcggtggttt ttctttattt atgagatgat gaatcaatcg gtctatcaag tcaacgaaca    2400
gctattccgt tactctagat ttcagtgcaa tttatctctt caaatgtagc acctgaagtc    2460
agccccatac gatataagtt gtaattctca tgttagtcat gccccgcgcc caccggaagg    2520
agctgactgg gttgaaggct ctcaagggca tcggtcgaga tcccggtgcc taatgagtga    2580
gctaacttac attaattgcg ttgcgctcac tgcccgcttt ccagtcggga aacctgtcgt    2640
gccagctgca ttaatgaatc ggccaacgcg cggggagagg cggtttgcgt attgggcgcc    2700
agggtggttt tcttttcac cagtgagacg ggcaacagct gattgccctt caccgcctgg    2760
ccctgagaga gttgcagcaa gcggtccacg ctggtttgcc ccagcaggcg aaaatcctgt    2820
tgatggtgg ttaacggcgg gatataacat gagctgtctt cggtatcgtc gtatcccact    2880
accgagatgt ccgcaccaac gcgcagcccg gactcggtaa tggcgcgcat gcgcccagc    2940
gccatctgat cgttggcaac cagcatcgca gtgggaacga tgccctcatt cagcatttgc    3000
atggtttgtt gaaaaccgga catggcactc cagtcgcctt cccgttccgc tatcggctga    3060
atttgattgc gagtgagata tttatgccag ccagccagac gcagacgcgc cgagacagaa    3120
cttaatgggc ccgctaacag cgcgatttgc tggtgaccca atgcgaccag atgctccacg    3180
cccagtcgcg taccgtcttc atgggagaaa ataatactgt tgatgggtgt ctggtcagag    3240
acatcaagaa ataacgccgg aacattagtg caggcagctt ccacagcaat ggcatcctgg    3300
tcatccagcg gatagttaat gatcagccca ctgacgcgtt gcgcgagaag attgtgcacc    3360
gccgctttac aggcttcgac gccgcttcgt tctaccatcg acaccaccac gctggcaccc    3420
agttgatcgg cgcgagattt aatcgccgcg acaatttgcg acggcgcgtg cagggccaga    3480
ctggaggtgg caacgccaat cagcaacgac tgtttgcccg ccagttgttg tgccacgcgg    3540
ttgggaatgt aattcagctc cgccatcgcc gcttccactt tttcccgcgt tttcgcagaa    3600
acgtggctgg cctggttcac cacgcgggaa acggtctgat aagagacacc ggcatactct    3660
gcgacatcgt ataacgttac tggtttcaca ttcaccaccc tgaattgact ctcttccggg    3720
cgctatcatg ccataccgcg aaaggttttg cgccattcga tggtgtccgg gatctcgacg    3780
ctctccctta tgcgactcct gcattaggaa attaatacga ctcactata               3829
```

<210> SEQ ID NO 37
<211> LENGTH: 761
<212> TYPE: PRT
<213> ORGANISM: Artificial sequence
<220> FEATURE:
<223> OTHER INFORMATION: GFPLLO amino acid sequence

<400> SEQUENCE: 37

```
Met Gly Ser Ser His His His His His His Ser Gln Asp Pro Met Ser
 1               5                  10                  15
```

-continued

```
Lys Gly Glu Glu Leu Phe Thr Gly Val Val Pro Ile Leu Val Glu Leu
                20                  25                  30

Asp Gly Asp Val Asn Gly Tyr Lys Phe Ser Val Ser Gly Glu Gly Glu
            35                  40                  45

Gly Asp Ala Thr Tyr Gly Lys Leu Thr Leu Lys Phe Ile Cys Thr Thr
50                  55                  60

Gly Lys Leu Pro Val Pro Trp Pro Thr Leu Val Thr Thr Leu Thr Tyr
65                  70                  75                  80

Gly Val Gln Cys Phe Ser Arg Tyr Pro Asp His Met Lys Arg His Asp
                85                  90                  95

Phe Phe Lys Ser Ala Met Pro Glu Gly Tyr Val Gln Glu Arg Thr Ile
            100                 105                 110

Phe Phe Lys Asp Asp Gly Asn Tyr Lys Thr Arg Ala Glu Val Lys Phe
        115                 120                 125

Glu Gly Asp Thr Leu Val Asn Arg Ile Glu Leu Lys Gly Ile Asp Phe
    130                 135                 140

Lys Glu Asp Gly Asn Ile Leu Gly His Lys Leu Glu Tyr Asn Tyr Asn
145                 150                 155                 160

Ser His Asn Val Tyr Ile Met Ala Asp Lys Gln Lys Asn Gly Ile Lys
                165                 170                 175

Ala Asn Phe Lys Thr Arg His Asn Ile Glu Asp Gly Gly Val Gln Leu
            180                 185                 190

Ala Asp His Tyr Gln Gln Asn Thr Pro Ile Gly Asp Asp Pro Val Leu
        195                 200                 205

Leu Pro Asp Asn His Tyr Leu Ser Thr Gln Ser Ala Leu Ser Lys Asp
    210                 215                 220

Pro Asn Glu Lys Arg Asp His Met Val Leu Leu Glu Phe Val Thr Ala
225                 230                 235                 240

Ala Gly Ile Thr His Gly Met Asp Glu Leu Tyr Lys Thr Gly Trp Glu
                245                 250                 255

Leu Gln Ala Ser Ala Phe Asn Lys Glu Asn Ser Ile Ser Ser Met Ala
            260                 265                 270

Pro Pro Ala Ser Pro Ala Ser Pro Lys Thr Pro Ile Glu Lys Lys
        275                 280                 285

His Ala Asp Glu Ile Asp Lys Tyr Ile Gln Gly Leu Asp Tyr Asn Lys
    290                 295                 300

Asn Asn Val Leu Val Tyr His Gly Asp Ala Val Thr Asn Val Pro Pro
305                 310                 315                 320

Arg Lys Gly Tyr Lys Asp Gly Asn Glu Tyr Ile Val Val Glu Lys Lys
                325                 330                 335

Lys Lys Ser Ile Asn Gln Asn Asn Ala Asp Ile Gln Val Val Asn Ala
            340                 345                 350

Ile Ser Ser Leu Thr Tyr Pro Gly Ala Leu Val Lys Ala Asn Ser Glu
        355                 360                 365

Leu Val Glu Asn Gln Pro Asp Val Leu Pro Val Lys Arg Asp Ser Leu
    370                 375                 380

Thr Leu Ser Ile Asp Leu Pro Gly Met Thr Asn Gln Asp Asn Lys Ile
385                 390                 395                 400

Val Val Lys Asn Ala Thr Lys Ser Asn Val Asn Asn Ala Val Asn Thr
                405                 410                 415

Leu Val Glu Arg Trp Asn Glu Lys Tyr Ala Gln Ala Tyr Pro Asn Val
            420                 425                 430
```

Ser Ala Lys Ile Asp Tyr Asp Asp Glu Met Ala Tyr Ser Glu Ser Gln
    435                 440                 445

Leu Ile Ala Lys Phe Gly Thr Ala Phe Lys Ala Val Asn Asn Ser Leu
450                 455                 460

Asn Val Asn Phe Gly Ala Ile Ser Glu Gly Lys Met Gln Glu Glu Val
465                 470                 475                 480

Ile Ser Phe Lys Gln Ile Tyr Tyr Asn Val Asn Val Asn Glu Pro Thr
                485                 490                 495

Arg Pro Ser Arg Phe Phe Gly Lys Ala Val Thr Lys Glu Gln Leu Gln
            500                 505                 510

Ala Leu Gly Val Asn Ala Glu Asn Pro Pro Ala Tyr Ile Ser Ser Val
        515                 520                 525

Ala Tyr Gly Arg Gln Val Tyr Leu Lys Leu Ser Thr Asn Ser His Ser
    530                 535                 540

Thr Lys Val Lys Ala Ala Phe Asp Ala Ala Val Ser Gly Lys Ser Val
545                 550                 555                 560

Ser Gly Asp Val Glu Leu Thr Asn Ile Lys Asn Ser Ser Phe Lys
                565                 570                 575

Ala Val Ile Tyr Gly Gly Ser Ala Lys Asp Glu Val Gln Ile Ile Asp
            580                 585                 590

Gly Asn Leu Gly Asp Leu Arg Asp Ile Leu Lys Lys Gly Ala Thr Phe
        595                 600                 605

Asn Arg Glu Thr Pro Gly Val Pro Ile Ala Tyr Thr Thr Asn Phe Leu
    610                 615                 620

Lys Asp Asn Glu Leu Ala Val Ile Lys Asn Asn Ser Glu Tyr Ile Glu
625                 630                 635                 640

Thr Thr Ser Lys Ala Tyr Thr Asp Gly Lys Ile Asn Ile Asp His Ser
                645                 650                 655

Gly Gly Tyr Val Ala Gln Phe Asn Ile Ser Trp Asp Glu Val Asn Tyr
            660                 665                 670

Asp Pro Glu Gly Asn Glu Ile Val Gln His Lys Asn Trp Ser Glu Asn
        675                 680                 685

Asn Lys Ser Lys Leu Ala His Phe Thr Ser Ser Ile Tyr Leu Pro Gly
    690                 695                 700

Asn Ala Arg Asn Ile Asn Val Tyr Ala Lys Glu Cys Thr Gly Leu Ala
705                 710                 715                 720

Trp Glu Trp Trp Arg Thr Val Ile Asp Asp Arg Asn Leu Pro Leu Val
                725                 730                 735

Lys Asn Arg Asn Ile Ser Ile Trp Gly Thr Thr Leu Tyr Pro Lys Tyr
            740                 745                 750

Ser Asn Lys Val Asp Asn Pro Ile Glu
    755                 760

<210> SEQ ID NO 38
<211> LENGTH: 2283
<212> TYPE: DNA
<213> ORGANISM: Artificial sequence
<220> FEATURE:
<223> OTHER INFORMATION: GFPLLO nucleotide sequence

<400> SEQUENCE: 38
atgggcagca gccatcacca tcatcaccac agccaggatc cgatgagtaa aggagaagaa    60
cttttcactg gagttgtccc aattcttgtt gaattagatg gtgatgttaa tgggtacaaa   120
ttttctgtca gtggagaggg tgaaggtgat gcaacatacg gaaaacttac ccttaaattt   180

```
atttgcacta ctggaaaact acctgttcca tggccaacac ttgtcactac tctcacttat    240
ggtgttcaat gcttttcaag atatccagat catatgaagc ggcacgactt cttcaagagc    300
gccatgcctg agggatacgt gcaggagagg accatcttct tcaaggacga cgggaactac    360
aagacacgtg ctgaagtcaa gtttgaggga cacccctcg tcaacaggat cgagcttaag    420
ggaatcgatt tcaaggagga cggaaacatc ctcggccaca agttggaata caactacaac    480
tcccacaacg tatacatcat ggccgacaag caaaagaacg gcatcaaagc caacttcaag    540
acccgccaca catcgaaga cggcggcgtg caactcgctg atcattatca acaaaatact    600
ccaattggcg atgaccctgt ccttttacca gacaaccatt acctgtccac acaatctgcc    660
ctttcgaaag atcccaacga aaagagagac cacatggtcc ttcttgagtt tgtaacggct    720
gctgggatta cacatggcat ggatgaacta tacaaaaccg gttgggaact gcaggcatct    780
gcattcaata agaaaattc aatttcatcc atggcaccac cagcatctcc gcctgcaagt    840
cctaagacgc caatcgaaaa gaaacacgcg gatgaaatcg ataagtatat acaaggattg    900
gattacaata aaaacaatgt attagtatac cacggagatg cagtgacaaa tgtgccgcca    960
agaaaaggtt acaagatgg aaatgaatat attgttgtgg agaaaaagaa gaaatccatc    1020
aatcaaaata atgcagacat tcaagttgtg aatgcaattt cgagcctaac ctatccaggt    1080
gctctcgtaa aagcgaattc ggaattagta gaaaatcaac cagatgttct ccctgtaaaa    1140
cgtgattcat taacactcag cattgatttg ccaggtatga ctaatcaaga caataaaatc    1200
gttgtaaaaa atgccactaa atcaaacgtt aacaacgcag taatacatt agtggaaaga    1260 tggaatgaaa aatatgctca agcttatcca aatgtaagtg caaaaattga ttatgatgac    1320
gaaatggctt acagtgaatc acaattaatt gcgaaatttg gtacagcatt taaagctgta    1380
aataatagct tgaatgtaaa cttcggcgca atcagtgaag ggaaaatgca agaagaagtc    1440
attagtttta aacaaattta ctataacgtg aatgttaatg aacctacaag accttccaga    1500
tttttcggca aagctgttac taaagagcag ttgcaagcgc ttggagtgaa tgcagaaaat    1560
cctcctgcat atatctcaag tgtggcgtat ggccgtcaag tttatttgaa attatcaact    1620
aattcccata gtactaaagt aaaagctgct tttgatgctg ccgtaagcgg aaaatctgtc    1680
tcaggtgatg tagaactaac aaatatcatc aaaaattctt ccttcaaagc cgtaatttac    1740
ggaggttccg caaagatga agttcaaatc atcgacggca acctcggaga cttacgcgat    1800
attttgaaaa aaggcgctac ttttaatcga gaaacaccag gagttcccat tgcttataca    1860
acaaacttcc taaaagacaa tgaattagct gttattaaaa acaactcaga atatattgaa    1920
acaacttcaa aagcttatac agatggaaaa attaacatcg atcactctgg aggatacgtt    1980
gctcaattca catttcttg ggatgaagta aattatgatc ctgaaggtaa cgaaattgtt    2040
caacataaaa actggagcga aaacaataaa agcaagctag ctcatttcac atcgtccatc    2100
tatttgccag gtaacgcgag aaatattaat gtttacgcta agaatgcac tggtttagct    2160 tgggaatggt ggagaacggt aattgatgac cggaacttac cacttgtgaa aaatagaaat    2220
atctccatct ggggcaccac gctttatccg aaatatagta ataaagtaga taatccaatc    2280
gaa                                                                 2283
```

<210> SEQ ID NO 39
<211> LENGTH: 1065
<212> TYPE: PRT
<213> ORGANISM: Artificial sequence
<220> FEATURE:

<223> OTHER INFORMATION: GFPActA amino acid sequence

<400> SEQUENCE: 39

```
Met Gly Ser Ser His His His His His His Ser Gln Asp Pro Met Ser
1               5                   10                  15

Lys Gly Glu Glu Leu Phe Thr Gly Val Val Pro Ile Leu Val Glu Leu
            20                  25                  30

Asp Gly Asp Val Asn Gly Tyr Lys Phe Ser Val Ser Gly Glu Gly Glu
        35                  40                  45

Gly Asp Ala Thr Tyr Gly Lys Leu Thr Leu Lys Phe Ile Cys Thr Thr
    50                  55                  60

Gly Lys Leu Pro Val Pro Trp Pro Thr Leu Val Thr Thr Leu Thr Tyr
65                  70                  75                  80

Gly Val Gln Cys Phe Ser Arg Tyr Pro Asp His Met Lys Arg His Asp
                85                  90                  95

Phe Phe Lys Ser Ala Met Pro Glu Gly Tyr Val Gln Glu Arg Thr Ile
            100                 105                 110

Phe Phe Lys Asp Asp Gly Asn Tyr Lys Thr Arg Ala Glu Val Lys Phe
        115                 120                 125

Glu Gly Asp Thr Leu Val Asn Arg Ile Glu Leu Lys Gly Ile Asp Phe
    130                 135                 140

Lys Glu Asp Gly Asn Ile Leu Gly His Lys Leu Glu Tyr Asn Tyr Asn
145                 150                 155                 160

Ser His Asn Val Tyr Ile Met Ala Asp Lys Gln Lys Asn Gly Ile Lys
                165                 170                 175

Ala Asn Phe Lys Thr Arg His Asn Ile Glu Asp Gly Gly Val Gln Leu
            180                 185                 190

Ala Asp His Tyr Gln Gln Asn Thr Pro Ile Gly Asp Gly Pro Val Leu
        195                 200                 205

Leu Pro Asp Asn His Tyr Leu Ser Thr Gln Ser Ala Leu Ser Lys Asp
    210                 215                 220

Pro Asn Glu Lys Arg Asp His Met Val Leu Leu Glu Phe Val Thr Ala
225                 230                 235                 240

Ala Gly Ile Thr His Gly Met Asp Glu Leu Tyr Lys Thr Gly Trp Glu
                245                 250                 255

Leu Gln Asp Ser Glu Asp Ser Ser Leu Asn Thr Asp Glu Trp Glu Glu
            260                 265                 270

Glu Lys Thr Glu Glu Gln Pro Ser Glu Val Asn Thr Gly Pro Arg Tyr
        275                 280                 285

Glu Thr Ala Arg Glu Val Ser Ser Arg Asp Ile Lys Glu Leu Glu Lys
    290                 295                 300

Ser Asn Lys Val Arg Asn Thr Asn Lys Ala Asp Leu Ile Ala Met Leu
305                 310                 315                 320

Lys Glu Lys Ala Glu Lys Gly Pro Asn Ile Asn Asn Asn Asn Ser Glu
                325                 330                 335

Gln Thr Glu Asn Ala Ala Ile Asn Glu Glu Ala Ser Gly Ala Asp Arg
            340                 345                 350

Pro Ala Ile Gln Val Glu Arg Arg His Pro Gly Leu Pro Ser Asp Ser
        355                 360                 365

Ala Ala Glu Ile Lys Lys Arg Arg Lys Ala Ile Ala Ser Ser Asp Ser
    370                 375                 380

Glu Leu Glu Ser Leu Thr Tyr Pro Asp Lys Pro Thr Lys Val Asn Lys
385                 390                 395                 400
```

-continued

```
Lys Lys Val Ala Lys Glu Ser Val Ala Asp Ala Ser Glu Ser Asp Leu
                405                 410                 415

Asp Ser Ser Met Gln Ser Ala Asp Glu Ser Ser Pro Gln Pro Leu Lys
            420                 425                 430

Ala Asn Gln Gln Pro Phe Phe Pro Lys Val Phe Lys Lys Ile Lys Asp
        435                 440                 445

Ala Gly Lys Trp Val Arg Asp Lys Ile Asp Glu Asn Pro Glu Val Lys
    450                 455                 460

Lys Ala Ile Val Asp Lys Ser Ala Gly Leu Ile Asp Gln Leu Leu Thr
465                 470                 475                 480

Lys Lys Lys Ser Glu Glu Val Asn Ala Ser Asp Phe Pro Pro Pro
                485                 490                 495

Thr Asp Glu Glu Leu Arg Leu Ala Leu Pro Glu Thr Pro Met Leu Leu
                500                 505                 510

Gly Phe Asn Ala Pro Ala Thr Ser Glu Pro Ser Ser Phe Glu Phe Pro
            515                 520                 525

Pro Pro Pro Thr Asp Glu Glu Leu Arg Leu Ala Leu Pro Glu Thr Pro
        530                 535                 540

Met Leu Leu Gly Phe Asn Ala Pro Ala Thr Ser Glu Pro Ser Ser Phe
545                 550                 555                 560

Glu Phe Pro Pro Pro Thr Glu Asp Glu Leu Glu Ile Ile Arg Glu
                565                 570                 575

Thr Ala Ser Ser Leu Asp Ser Ser Phe Thr Arg Gly Asp Leu Ala Ser
            580                 585                 590

Leu Arg Asn Ala Ile Asn Arg His Ser Gln Asn Phe Ser Asp Phe Pro
        595                 600                 605

Pro Ile Pro Thr Glu Glu Glu Leu Asn Gly Arg Gly Arg Pro Thr
    610                 615                 620

Ser Glu Glu Phe Ser Ser Leu Asn Ser Gly Asp Phe Thr Asp Glu
625                 630                 635                 640

Asn Ser Glu Thr Thr Glu Glu Ile Asp Arg Leu Ala Asp Leu Arg
                645                 650                 655

Asp Arg Gly Thr Gly Lys His Ser Arg Asn Ala Gly Phe Leu Pro Leu
            660                 665                 670

Asn Pro Phe Ala Ser Ser Pro Val Pro Ser Leu Ser Pro Lys Val Ser
        675                 680                 685

Lys Ile Ser Ala Pro Ala Leu Ile Ser Asp Ile Thr Lys Lys Thr Pro
    690                 695                 700

Phe Lys Asn Pro Ser Gln Pro Leu Asn Val Phe Asn Lys Lys Thr Thr
705                 710                 715                 720

Thr Lys Thr Val Thr Lys Lys Pro Thr Pro Val Lys Thr Ala Pro Lys
                725                 730                 735

Leu Ala Glu Leu Pro Ala Thr Lys Pro Gln Glu Thr Val Leu Arg Glu
            740                 745                 750

Asn Lys Thr Pro Phe Ile Glu Lys Gln Ala Glu Thr Asn Lys Gln Ser
        755                 760                 765

Ile Asn Met Pro Ser Leu Pro Val Ile Gln Lys Glu Ala Thr Glu Ser
    770                 775                 780

Asp Lys Glu Glu Met Lys Pro Gln Thr Glu Glu Lys Met Val Glu Glu
785                 790                 795                 800

Ser Glu Ser Ala Asn Asn Ala Asn Gly Lys Asn Arg Ser Ala Gly Ile
                805                 810                 815
```

Glu Glu Gly Lys Leu Ile Ala Lys Ser Ala Glu Asp Glu Lys Ala Lys
            820                 825                 830
Glu Glu Pro Gly Asn His Thr Thr Ala Val Pro Arg Ala Ala Ala Ser
            835                 840                 845
Pro Ile Leu Gly Tyr Trp Lys Ile Lys Gly Leu Val Gln Pro Thr Arg
            850                 855                 860
Leu Leu Leu Glu Tyr Leu Glu Glu Lys Tyr Glu Glu His Leu Tyr Glu
865                 870                 875                 880
Arg Asp Glu Gly Asp Lys Trp Arg Asn Lys Lys Phe Glu Leu Gly Leu
            885                 890                 895
Glu Phe Pro Asn Leu Pro Tyr Tyr Ile Asp Gly Asp Val Lys Leu Thr
            900                 905                 910
Gln Ser Met Ala Ile Ile Arg Tyr Ile Ala Asp Lys His Asn Met Leu
            915                 920                 925
Gly Gly Cys Pro Lys Glu Arg Ala Glu Ile Ser Met Leu Glu Gly Ala
            930                 935                 940
Val Leu Asp Ile Arg Tyr Gly Val Ser Arg Ile Ala Tyr Ser Lys Asp
945                 950                 955                 960
Phe Glu Thr Leu Lys Val Asp Phe Leu Ser Lys Leu Pro Glu Met Leu
            965                 970                 975
Lys Met Phe Glu Asp Arg Leu Cys His Lys Thr Tyr Leu Asn Gly Asp
            980                 985                 990
His Val Thr His Pro Asp Phe Met Leu Tyr Asp Ala Leu Asp Val Val
            995                 1000                1005
Leu Tyr Met Asp Pro Met Cys Leu Asp Ala Phe Pro Lys Leu Val
            1010                1015                1020
Cys Phe Lys Lys Arg Ile Glu Ala Ile Pro Gln Ile Asp Lys Tyr
            1025                1030                1035
Leu Lys Ser Ser Lys Tyr Ile Ala Trp Pro Leu Gln Gly Trp Gln
            1040                1045                1050
Ala Thr Phe Gly Gly Gly Asp His Pro Pro Lys Ser
            1055                1060                1065

<210> SEQ ID NO 40
<211> LENGTH: 3195
<212> TYPE: DNA
<213> ORGANISM: Artificial sequence
<220> FEATURE:
<223> OTHER INFORMATION: GFPActA nucleotide sequence

<400> SEQUENCE: 40
atgggcagca gccatcacca tcatcaccac agccaggatc cgatgagtaa aggagaagaa      60
cttttcactg gagttgtccc aattcttgtt gaattagatg gtgatgttaa tgggtacaaa     120
ttttctgtca gtggagaggg tgaaggtgat gcaacatacg gaaaacttac ccttaaattt     180
atttgcacta ctggaaaact acctgttcca tggccaacac ttgtcactac tctcacttat     240
ggtgttcaat gcttttcaag atatccagat catatgaagc ggcacgactt cttcaagagc     300
gccatgcctg agggatacgt gcaggagagg accatcttct tcaaggacga cgggaactac     360
aagacacgtg ctgaagtcaa gtttgaggga cacccctcg tcaacaggat cgagcttaag     420
ggaatcgatt tcaaggagga cggaaacatc ctcggccaca gttggaata caactacaac     480 tcccacaacg tatacatcat ggccgacaag caaagaacg gcatcaaagc caacttcaag     540
acccgccaca acatcgaaga cggcggcgtg caactcgctg atcattatca acaaaatact     600

```
ccaattggcg atgaccctgt cctttacca gacaaccatt acctgtccac acaatctgcc    660
ctttcgaaag atcccaacga aaagagagac acatggtcc ttcttgagtt tgtaacggct    720
gctgggatta cacatggcat ggatgaacta tacaaaaccg gttgggaact gcaggatagc    780
gaagattcta gtctaaacac agatgaatgg gaagaagaaa aaacagaaga gcaaccaagc    840
gaggtaaata cgggaccaag atacgaaact gcacgtgaag taagttcacg tgatattaaa    900
gaactagaaa aatcgaataa agtgagaaat acgaacaaag cagacctaat agcaatgttg    960
aaagaaaaag cagaaaaagg tccaaatatc aataataaca acagtgaaca aactgagaat    1020
gcggctataa atgaagaggc ttcaggagcc gaccgaccag ctatacaagt ggagcgtcgt    1080
catccaggat tgccatcgga tagcgcagcg gaaattaaaa aaagaaggaa agccatagca    1140
tcatcggata gtgagcttga aagccttact tatccggata aaccaacaaa agtaaataag    1200
aaaaaagtgg cgaaagagtc agttgcggat gcttctgaaa gtgacttaga ttctagcatg    1260
cagtcagcag atgagtcttc accacaacct ttaaaagcaa accaacaacc attttcccct    1320
aaagtattta aaaaaataaa agatgcgggg aaatgggtac gtgataaaat cgacgaaaat    1380
cctgaagtaa agaaagcgat tgttgataaa agtgcagggt taattgacca attattaacc    1440
aaaaagaaaa gtgaagaggt aaatgcttcg gacttcccgc caccacctac ggatgaagag    1500
ttaagacttg cttgtccaga gacaccaatg cttcttggtt ttaatgctcc tgctacatca    1560
gaaccgagct cattcgaatt tccaccacca cctacggatg aagagttaag acttgctttg    1620
ccagagacgc caatgcttct tggttttaat gctcctgcta catcggaacc gagctcgttc    1680
gaatttccac cgcctccaac agaagatgaa ctagaaatca tccgggaaac agcatcctcg    1740
ctagattcta gttttacaag aggggattta gctagtttga gaaatgctat taatcgccat    1800
agtcaaaatt tctctgattt cccaccaatc ccaacagaag aagagttgaa cgggagaggc    1860
ggtagaccaa catctgaaga atttagttcg ctgaatagtg gtgatttac agatgacgaa    1920 aacagcgaga caacagaaga agaaattgat cgcctagctg atttaagaga tagaggaaca    1980
ggaaaacact caagaaatgc gggttttta ccattaaatc cgtttgctag cagcccggtt    2040
ccttcgttaa gtccaaaggt atcgaaaata agcgcaccgg ctctgataag tgacataact    2100
aaaaaaacgc catttaagaa tccatcacag ccattaaatg tgtttaataa aaaaactaca    2160
acgaaaacag tgactaaaaa accaaccct gtaaagaccg caccaaagct agcagaactt    2220
cctgccacaa aaccacaaga aaccgtactt agggaaaata aaacacccctt tatagaaaaa    2280 caagcagaaa caaacaagca gtcaattaat atgccgagcc taccagtaat ccaaaaagaa    2340
gctacagaga gcgataaaga ggaaatgaaa ccacaaaccg aggaaaaaat ggtagaggaa    2400
agcgaatcag ctaataacgc aaacggaaaa aatcgttctg ctggcattga agaaggaaaa    2460
ctaattgcta aaagtgcaga agacgaaaaa gcgaaggaag aaccagggaa ccatacgacg    2520
gcagtaccac gcgcggccgc gtcccctata ctaggttatt ggaaaattaa gggccttgtg    2580
caacccactc gacttctttt ggaatatctt gaagaaaaat atgaagagca tttgtatgag    2640
cgcgatgaag gtgataaatg gcgaaacaaa aagtttgaat tgggtttgga gtttcccaat    2700
cttccttatt atattgatgg tgatgttaaa ttaacacagt ctatggccat catacgttat    2760
atagctgaca agcacaacat gttgggtggt tgtccaaaag agcgtgcaga gatttcaatg    2820
cttgaaggag cggttttgga tattagatac ggtgtttcga gaattgcata tagtaaagac    2880
tttgaaactc tcaaagttga ttttcttagc aagctacctg aaatgctgaa atgttcgaa    2940 gatcgtttat gtcataaaac atatttaaat ggtgatcatg taacccatcc tgacttcatg    3000
```

```
ttgtatgacg ctcttgatgt tgttttatac atggacccaa tgtgcctgga tgcgttccca    3060
aaattagttt gttttaaaaa acgtattgaa gctatcccac aaattgataa gtacttgaaa    3120
tccagcaagt atatagcatg gcctttgcag ggctggcaag ccacgtttgg tggtggcgac    3180
catcctccaa aatcg                                                     3195

<210> SEQ ID NO 41
<211> LENGTH: 50
<212> TYPE: DNA
<213> ORGANISM: Artificial sequence
<220> FEATURE:
<223> OTHER INFORMATION: GFP_BamHI_F primer sequence

<400> SEQUENCE: 41
ggatccgatg agtaaaggag aagaactttt cactggagtt gtcccaattc                 50

<210> SEQ ID NO 42
<211> LENGTH: 50
<212> TYPE: DNA
<213> ORGANISM: Artificial sequence
<220> FEATURE:
<223> OTHER INFORMATION: GFPWELQ_PstI_R primer sequence

<400> SEQUENCE: 42
ctgcagttcc caaccggttt tgtatagttc atccatgcca tgtgtaatcc                 50

<210> SEQ ID NO 43
<211> LENGTH: 38
<212> TYPE: DNA
<213> ORGANISM: Artificial sequence
<220> FEATURE:
<223> OTHER INFORMATION: NisA_BamHI_F primer sequence

<400> SEQUENCE: 43
ctagatggat ccgatgagta caaaagattt taacttgg                             38

<210> SEQ ID NO 44
<211> LENGTH: 37
<212> TYPE: DNA
<213> ORGANISM: Artificial sequence
<220> FEATURE:
<223> OTHER INFORMATION: NisA_HindIII_R primer

<400> SEQUENCE: 44
ctagaagctt ttatttgctt acgtgaatac tacaatg                              37

<210> SEQ ID NO 45
<211> LENGTH: 43
<212> TYPE: DNA
<213> ORGANISM: Artificial sequence
<220> FEATURE:
<223> OTHER INFORMATION: NisB_BglII_F primer

<400> SEQUENCE: 45
cagccgagat ctgatgataa aaagttcatt taaagctcaa ccg                       43

<210> SEQ ID NO 46
<211> LENGTH: 42
<212> TYPE: DNA
<213> ORGANISM: Artificial sequence
<220> FEATURE:
<223> OTHER INFORMATION: NisB_XhoI_R primer
```

<400> SEQUENCE: 46
ctagctcgag tcatttcatg tattcttccg aaacaaacaa cc            42

<210> SEQ ID NO 47
<211> LENGTH: 45
<212> TYPE: DNA
<213> ORGANISM: Artificial sequence
<220> FEATURE:
<223> OTHER INFORMATION: NisC_BglII_F primer

<400> SEQUENCE: 47
ctagggaaga tctgatgaat aaaaaaaata taaaaagaaa tgttg         45

<210> SEQ ID NO 48
<211> LENGTH: 43
<212> TYPE: DNA
<213> ORGANISM: Artificial sequence
<220> FEATURE:
<223> OTHER INFORMATION: NisC_XhoI_R primer

<400> SEQUENCE: 48
ctagctcgag tcatttcctc ttccctcctt tcaaaaaatc gtc           43

<210> SEQ ID NO 49
<211> LENGTH: 24
<212> TYPE: DNA
<213> ORGANISM: Artificial sequence
<220> FEATURE:
<223> OTHER INFORMATION: GFPNisLeader_PstI_F primer

<400> SEQUENCE: 49
ggaactgcag atgagtacaa aaga                                24

<210> SEQ ID NO 50
<211> LENGTH: 37
<212> TYPE: DNA
<213> ORGANISM: Artificial sequence
<220> FEATURE:
<223> OTHER INFORMATION: NisinLThPep5_F primer

<400> SEQUENCE: 50
caggtgcagt accacgcacc gcgggtccgg cgatccg                  37

<210> SEQ ID NO 51
<211> LENGTH: 30
<212> TYPE: DNA
<213> ORGANISM: Artificial sequence
<220> FEATURE:
<223> OTHER INFORMATION: Pep5HindIII_R primer

<400> SEQUENCE: 51
caccaagctt ttatttgcag ccgttttttac                         30

<210> SEQ ID NO 52
<211> LENGTH: 37
<212> TYPE: DNA
<213> ORGANISM: Artificial sequence
<220> FEATURE:
<223> OTHER INFORMATION: NisinLTh15X_F primer

<400> SEQUENCE: 52
caggtgcagt accacgcagc gcgagcatcg tgaagac                  37

<210> SEQ ID NO 53

<211> LENGTH: 31
<212> TYPE: DNA
<213> ORGANISM: Artificial sequence
<220> FEATURE:
<223> OTHER INFORMATION: 15XHindIII_R primer

<400> SEQUENCE: 53
gcgccaagct tttatttctt gccggtaaag t                            31

<210> SEQ ID NO 54
<211> LENGTH: 21
<212> TYPE: DNA
<213> ORGANISM: Artificial sequence
<220> FEATURE:
<223> OTHER INFORMATION: NisLeaderThr_R primer

<400> SEQUENCE: 54
gcgtggtact gcacctgaat c                                       21

<210> SEQ ID NO 55
<211> LENGTH: 25
<212> TYPE: DNA
<213> ORGANISM: Artificial sequence
<220> FEATURE:
<223> OTHER INFORMATION: NisLeaderOri_F primer

<400> SEQUENCE: 55
gaaagattca ggtgcatcac cacgc                                   25

<210> SEQ ID NO 56
<211> LENGTH: 25
<212> TYPE: DNA
<213> ORGANISM: Artificial sequence
<220> FEATURE:
<223> OTHER INFORMATION: NisLeaderOri_R primer

<400> SEQUENCE: 56
gcgtggtgat gcacctgaat ctttc                                   25

<210> SEQ ID NO 57
<211> LENGTH: 30
<212> TYPE: DNA
<213> ORGANISM: Artificial sequence
<220> FEATURE:
<223> OTHER INFORMATION: NisLeaderNisThr_F primer

<400> SEQUENCE: 57
ttcaggtgca gtaccacgca ttacaagtat                              30

<210> SEQ ID NO 58
<211> LENGTH: 30
<212> TYPE: DNA
<213> ORGANISM: Artificial sequence
<220> FEATURE:
<223> OTHER INFORMATION: NisLeaderNisThr_R primer

<400> SEQUENCE: 58
atacttgtaa tgcgtggtac tgcacctgaa                              30

<210> SEQ ID NO 59
<211> LENGTH: 33
<212> TYPE: DNA
<213> ORGANISM: Artificial sequence
<220> FEATURE:
<223> OTHER INFORMATION: GFP-PlaX_Pst_Fwd primer

```
<400> SEQUENCE: 59
taagggatcc gtgggaactg cagaaatact atg                                      33

<210> SEQ ID NO 60
<211> LENGTH: 41
<212> TYPE: DNA
<213> ORGANISM: Artificial sequence
<220> FEATURE:
<223> OTHER INFORMATION: GFP-PlaX_Hind_Rev primer

<400> SEQUENCE: 60
tattaagctt agcactttcc atgaccgaag ttagctaaat g                             41

<210> SEQ ID NO 61
<211> LENGTH: 47
<212> TYPE: DNA
<213> ORGANISM: Artificial sequence
<220> FEATURE:
<223> OTHER INFORMATION: GFP-MunX_Pst_Fwd primer

<400> SEQUENCE: 61
atcgctgcag aaatactacg gtaatggagt ctcatgtaat aaaaaag                       47

<210> SEQ ID NO 62
<211> LENGTH: 29
<212> TYPE: DNA
<213> ORGANISM: Artificial sequence
<220> FEATURE:
<223> OTHER INFORMATION: GFP-MunX_Hind_Rev primer

<400> SEQUENCE: 62
acgcaagctt aacttttcca accagctgc                                           29

<210> SEQ ID NO 63
<211> LENGTH: 20
<212> TYPE: DNA
<213> ORGANISM: Artificial sequence
<220> FEATURE:
<223> OTHER INFORMATION: pRSFMCS1_R primer

<400> SEQUENCE: 63
gattatgcgg ccgtgtacaa                                                     20

<210> SEQ ID NO 64
<211> LENGTH: 35
<212> TYPE: DNA
<213> ORGANISM: Artificial sequence
<220> FEATURE:
<223> OTHER INFORMATION: GST_NotI_F primer

<400> SEQUENCE: 64
gcgcggccgc gtcccctata ctaggttatt ggaaa                                    35

<210> SEQ ID NO 65
<211> LENGTH: 35
<212> TYPE: DNA
<213> ORGANISM: Artificial sequence
<220> FEATURE:
<223> OTHER INFORMATION: GST_XhoI_R primer

<400> SEQUENCE: 65
cagactcgag ttacgatttt ggaggatggt cgcca                                    35

<210> SEQ ID NO 66
```

```
<211> LENGTH: 30
<212> TYPE: DNA
<213> ORGANISM: Artificial sequence
<220> FEATURE:
<223> OTHER INFORMATION: WLLO_PstI_F primer

<400> SEQUENCE: 66
gggaactgca ggcatctgca ttcaataaag                              30

<210> SEQ ID NO 67
<211> LENGTH: 30
<212> TYPE: DNA
<213> ORGANISM: Artificial sequence
<220> FEATURE:
<223> OTHER INFORMATION: LLO_NotI_R primer

<400> SEQUENCE: 67
attatgcggc cgcttattcg attggattat                              30

<210> SEQ ID NO 68
<211> LENGTH: 37
<212> TYPE: DNA
<213> ORGANISM: Artificial sequence
<220> FEATURE:
<223> OTHER INFORMATION: WActA_PstI_F primer

<400> SEQUENCE: 68
gggaactgca ggatagcgaa gattctagtc taaacac                      37

<210> SEQ ID NO 69
<211> LENGTH: 30
<212> TYPE: DNA
<213> ORGANISM: Artificial sequence
<220> FEATURE:
<223> OTHER INFORMATION: ActA_NotI_R primer

<400> SEQUENCE: 69
atgcggccgc ttacgtcgta tggttccctg                              30

<210> SEQ ID NO 70
<211> LENGTH: 30
<212> TYPE: DNA
<213> ORGANISM: Artificial sequence
<220> FEATURE:
<223> OTHER INFORMATION: GPR-F primer

<400> SEQUENCE: 70
atggcagatc tggtagaaat caataatcaa                              30

<210> SEQ ID NO 71
<211> LENGTH: 33
<212> TYPE: DNA
<213> ORGANISM: Artificial sequence
<220> FEATURE:
<223> OTHER INFORMATION: GPR-R primer

<400> SEQUENCE: 71
ataggtacct catacatcaa tctctctgac cgt                          33

<210> SEQ ID NO 72
<211> LENGTH: 30
<212> TYPE: DNA
<213> ORGANISM: Artificial sequence
<220> FEATURE:
<223> OTHER INFORMATION: GPE-F primer
```

```
<400> SEQUENCE: 72
atggcagatc tgaatatttt tgaaatgctg                                         30

<210> SEQ ID NO 73
<211> LENGTH: 30
<212> TYPE: DNA
<213> ORGANISM: Artificial sequence
<220> FEATURE:
<223> OTHER INFORMATION: GPE-R primer

<400> SEQUENCE: 73
cagactcgag ttacagattt ttatatgcat                                         30

<210> SEQ ID NO 74
<211> LENGTH: 214
<212> TYPE: DNA
<213> ORGANISM: Artificial sequence
<220> FEATURE:
<223> OTHER INFORMATION: Stationary phase promoter 1

<400> SEQUENCE: 74
ggcgccctgg cacaggaacg ttatccggac gttcagttcc accagacccg cgagcattaa        60
ttcttgcctc cagggcgcgg tagtcgcgcc ctgtcaattt cccttcctta ttagccgctt       120
acggaatgtt cttaaaacat tcacttttgc ttatgttttc gctcatatcc cgagcggttt       180
caaaattgtg atctatattt aacaaattaa ttaa                                   214

<210> SEQ ID NO 75
<211> LENGTH: 231
<212> TYPE: DNA
<213> ORGANISM: Artificial sequence
<220> FEATURE:
<223> OTHER INFORMATION: Stationary phase promoter 2

<400> SEQUENCE: 75
ggcgcctttg tggtgatcta cactgatact ctgttgcatt attcgcctga aaccacaata        60
ttcaggcgtt ttttcgctat cttttgacaaa aaatatcaac tttctcgatt tgctctcagc     120
ccttatatca cgggaaattc cggcgatttg ctcgcatcaa tattcatgcc acatttgcca       180
tcaggggccg cctcagattc tcagtatgtt ataatagaaa aaattaatta a                231

<210> SEQ ID NO 76
<211> LENGTH: 197
<212> TYPE: DNA
<213> ORGANISM: Artificial sequence
<220> FEATURE:
<223> OTHER INFORMATION: Stationary phase promoter 3

<400> SEQUENCE: 76
ggcgccaaaa aatattcagt tacaggaaag gtcagggcag ggattctaca gagttctgga        60
taaaatttgt atcgcaatct cattcgctgc cggaggcgaa ggaaatgtaa attttgttaa      120
ttcggcgtga agaattgatc ctggacagca ttttgctcaa aaaatagcca tactatttaa       180
ttgcaacaat taattaa                                                      197

<210> SEQ ID NO 77
<211> LENGTH: 328
<212> TYPE: DNA
<213> ORGANISM: Artificial sequence
<220> FEATURE:
<223> OTHER INFORMATION: Promoter / RNA thermometer combination 1
```

```
<400> SEQUENCE: 77
ggcgccaaaa aatattcagt tacaggaaag gtcagggcag ggattctaca gagttctgga    60
taaaatttgt atcgcaatct cattcgctgc cggaggcgaa ggaaatgtaa attttgttaa   120
ttcggcgtga agaattgatc ctggacagca ttttgctcaa aaaatagcca tactatttaa   180
ttgcaacaat taattaaggc ctaattatag cacttaatcg aaataaattt atgagtacgt   240
agagtataat tagtattctt ctttccaact tccttatact tatatactta tagattctaa   300
aatcatgaaa cggattcttt gcggatcc                                      328

<210> SEQ ID NO 78
<211> LENGTH: 261
<212> TYPE: DNA
<213> ORGANISM: Artificial sequence
<220> FEATURE:
<223> OTHER INFORMATION: Promoter / RNA thermometer combination 2

<400> SEQUENCE: 78
ggcgccaaaa aatattcagt tacaggaaag gtcagggcag ggattctaca gagttctgga    60
taaaatttgt atcgcaatct cattcgctgc cggaggcgaa ggaaatgtaa attttgttaa   120
ttcggcgtga agaattgatc ctggacagca ttttgctcaa aaaatagcca tactatttaa   180
ttgcaacaat taattaaaca gcaattttgc gttatctgtt aatcgagact gaaatacatg   240
aaaaaaacca cattaggatc c                                             261

<210> SEQ ID NO 79
<211> LENGTH: 437
<212> TYPE: DNA
<213> ORGANISM: Artificial sequence
<220> FEATURE:
<223> OTHER INFORMATION: Promoter / RNA thermometer combination 3

<400> SEQUENCE: 79
ggcgccaaaa aatattcagt tacaggaaag gtcagggcag ggattctaca gagttctgga    60
taaaatttgt atcgcaatct cattcgctgc cggaggcgaa ggaaatgtaa attttgttaa   120
ttcggcgtga agaattgatc ctggacagca ttttgctcaa aaaatagcca tactatttaa   180
ttgcaacaat taattaaacg gtttgacgta cagaccatta aagcagtgta gtaaggcaag   240
tcccttcaag agttatcgtt gataccoctc gtagtgcaca ttcctttaac gcttcaaaat   300
ctgtaaagca cgccatatcg ccgaaaggca cacttaatta ttaaaggtaa tacactatgt   360
ccggtaaaat gactggtatc gtaaaatggt tcaacgctga caaaggcttc ggcttcatca   420
ctcctgacga tggatcc                                                  437

<210> SEQ ID NO 80
<211> LENGTH: 261
<212> TYPE: DNA
<213> ORGANISM: Artificial sequence
<220> FEATURE:
<223> OTHER INFORMATION: Promoter / RNA thermometer combination 4

<400> SEQUENCE: 80
ggcgccaaaa aatattcagt tacaggaaag gtcagggcag ggattctaca gagttctgga    60
taaaatttgt atcgcaatct cattcgctgc cggaggcgaa ggaaatgtaa attttgttaa   120
ttcggcgtga agaattgatc ctggacagca ttttgctcaa aaaatagcca tactatttaa   180
ttgcaacaat taattaaaca gcaattttgc gttacctgtt aatcgagatt gaaacacatg   240
aaaaaaacca cattaggatc c                                             261
```

<210> SEQ ID NO 81
<211> LENGTH: 265
<212> TYPE: DNA
<213> ORGANISM: Artificial sequence
<220> FEATURE:
<223> OTHER INFORMATION: Promoter / RNA thermometer combination 5

<400> SEQUENCE: 81

```
ggcgccaaaa aatattcagt tacaggaaag gtcagggcag ggattctaca gagttctgga      60
taaaatttgt atcgcaatct cattcgctgc cggaggcgaa ggaaatgtaa attttgttaa     120
ttcggcgtga agaattgatc ctggacagca ttttgctcaa aaaatagcca tactatttaa     180
ttgcaacaat taattaaatt caagggtaat caattccttc cacacatcag gagttaacat     240
tatgtctctc attctttacg gatcc                                           265
```

<210> SEQ ID NO 82
<211> LENGTH: 292
<212> TYPE: DNA
<213> ORGANISM: Artificial sequence
<220> FEATURE:
<223> OTHER INFORMATION: Promoter / RNA thermometer combination 6

<400> SEQUENCE: 82

```
ggcgccaaaa aatattcagt tacaggaaag gtcagggcag ggattctaca gagttctgga      60
taaaatttgt atcgcaatct cattcgctgc cggaggcgaa ggaaatgtaa attttgttaa     120
ttcggcgtga agaattgatc ctggacagca ttttgctcaa aaaatagcca tactatttaa     180
ttgcaacaat taattaaggc cactttagtc tgtggttact gtattaggta ttgttataac     240
aatctggatg gttttttatga ataagacatt actggtctct tctttaggat cc            292
```

<210> SEQ ID NO 83
<211> LENGTH: 315
<212> TYPE: DNA
<213> ORGANISM: Artificial sequence
<220> FEATURE:
<223> OTHER INFORMATION: Promoter / RNA thermometer combination 7

<400> SEQUENCE: 83

```
ggcgccaaaa aatattcagt tacaggaaag gtcagggcag ggattctaca gagttctgga      60
taaaatttgt atcgcaatct cattcgctgc cggaggcgaa ggaaatgtaa attttgttaa     120
ttcggcgtga agaattgatc ctggacagca ttttgctcaa aaaatagcca tactatttaa     180
ttgcaacaat taattaatgt gttttttgta agttctatta aatacatcag tttacagcaa     240
tgaattcacc attgtgcatc gtcaataaaa ggagtgttta tgaaaaatca atggcaacat     300
caatattttg gatcc                                                      315
```

<210> SEQ ID NO 84
<211> LENGTH: 345
<212> TYPE: DNA
<213> ORGANISM: Artificial sequence
<220> FEATURE:
<223> OTHER INFORMATION: Promoter / RNA thermometer combination 8

<400> SEQUENCE: 84

```
ggcgccctgg cacaggaacg ttatccggac gttcagttcc accagacccg cgagcattaa      60
ttcttgcctc cagggcgcgg tagtcgcgcc ctgtcaattt cccttcctta ttagccgctt     120
acggaatgtt cttaaaacat tcacttttgc ttatgttttc gctcatatcc cgagcggttt     180
```

```
caaaattgtg atctatattt aacaaattaa ttaaggccta attatagcac ttaatcgaaa    240
taaatttatg agtacgtaga gtataattag tattcttctt tccaacttcc ttatacttat    300
atacttatag attctaaaat catgaaacgg attctttgcg gatcc                   345
```

<210> SEQ ID NO 85
<211> LENGTH: 295
<212> TYPE: DNA
<213> ORGANISM: Artificial sequence
<220> FEATURE:
<223> OTHER INFORMATION: Promoter / RNA thermometer combination 9

<400> SEQUENCE: 85

```
ggcgcctttg tggtgatcta cactgatact ctgttgcatt attcgcctga aaccacaata    60
ttcaggcgtt ttttcgctat ctttgacaaa aaatatcaac tttctcgatt tgctctcagc   120
ccttatatca cgggaaattc cggcgatttg ctcgcatcaa tattcatgcc acatttgcca   180
tcaggggccg cctcagattc tcagtatgtt ataatagaaa aaattaatta aacagcaatt   240
ttgcgttatc tgttaatcga gactgaaata catgaaaaaa accacattag gatcc        295
```

<210> SEQ ID NO 86
<211> LENGTH: 471
<212> TYPE: DNA
<213> ORGANISM: Artificial sequence
<220> FEATURE:
<223> OTHER INFORMATION: Promoter / RNA thermometer combination 10

<400> SEQUENCE: 86

```
ggcgcctttg tggtgatcta cactgatact ctgttgcatt attcgcctga aaccacaata    60
ttcaggcgtt ttttcgctat ctttgacaaa aaatatcaac tttctcgatt tgctctcagc   120
ccttatatca cgggaaattc cggcgatttg ctcgcatcaa tattcatgcc acatttgcca   180
tcaggggccg cctcagattc tcagtatgtt ataatagaaa aaattaatta aacggtttga   240
cgtacagacc attaaagcag tgtagtaagg caagtccctt caagagttat cgttgatacc   300
cctcgtagtg cacattcctt taacgcttca aaatctgtaa agcacgccat atcgccgaaa   360
ggcacactta attattaaag gtaatacact atgtccggta aaatgactgg tatcgtaaaa   420
tggttcaacg ctgacaaagg cttcggcttc atcactcctg acgatggatc c            471
```

<210> SEQ ID NO 87
<211> LENGTH: 295
<212> TYPE: DNA
<213> ORGANISM: Artificial sequence
<220> FEATURE:
<223> OTHER INFORMATION: Promoter / RNA thermometer combination 11

<400> SEQUENCE: 87

```
ggcgcctttg tggtgatcta cactgatact ctgttgcatt attcgcctga aaccacaata    60
ttcaggcgtt ttttcgctat ctttgacaaa aaatatcaac tttctcgatt tgctctcagc   120
ccttatatca cgggaaattc cggcgatttg ctcgcatcaa tattcatgcc acatttgcca   180
tcaggggccg cctcagattc tcagtatgtt ataatagaaa aaattaatta aacagcaatt   240
ttgcgttacc tgttaatcga gattgaaaca catgaaaaaa accacattag gatcc        295
```

<210> SEQ ID NO 88
<211> LENGTH: 299
<212> TYPE: DNA
<213> ORGANISM: Artificial sequence
<220> FEATURE:
<223> OTHER INFORMATION: Promoter / RNA thermometer combination 12

```
<400> SEQUENCE: 88
ggcgcctttg tggtgatcta cactgatact ctgttgcatt attcgcctga aaccacaata      60
ttcaggcgtt ttttcgctat ctttgacaaa aaatatcaac tttctcgatt tgctctcagc    120
ccttatatca cgggaaattc cggcgatttg ctcgcatcaa tattcatgcc acatttgcca    180
tcaggggccg cctcagattc tcagtatgtt ataatagaaa aaattaatta aattcaaggg    240
taatcaattc cttccacaca tcaggagtta acattatgtc tctcattctt tacggatcc     299

<210> SEQ ID NO 89
<211> LENGTH: 326
<212> TYPE: DNA
<213> ORGANISM: Artificial sequence
<220> FEATURE:
<223> OTHER INFORMATION: Promoter / RNA thermometer combination 13

<400> SEQUENCE: 89
ggcgcctttg tggtgatcta cactgatact ctgttgcatt attcgcctga aaccacaata      60
ttcaggcgtt ttttcgctat ctttgacaaa aaatatcaac tttctcgatt tgctctcagc    120
ccttatatca cgggaaattc cggcgatttg ctcgcatcaa tattcatgcc acatttgcca    180
tcaggggccg cctcagattc tcagtatgtt ataatagaaa aaattaatta aggccacttt    240
agtctgtggt tactgtatta ggtattgtta taacaatctg gatggttttt atgaataaga    300
cattactggt ctcttcttta ggatcc                                         326

<210> SEQ ID NO 90
<211> LENGTH: 349
<212> TYPE: DNA
<213> ORGANISM: Artificial sequence
<220> FEATURE:
<223> OTHER INFORMATION: Promoter / RNA thermometer combination 14

<400> SEQUENCE: 90
ggcgcctttg tggtgatcta cactgatact ctgttgcatt attcgcctga aaccacaata      60
ttcaggcgtt ttttcgctat ctttgacaaa aaatatcaac tttctcgatt tgctctcagc    120
ccttatatca cgggaaattc cggcgatttg ctcgcatcaa tattcatgcc acatttgcca    180
tcaggggccg cctcagattc tcagtatgtt ataatagaaa aaattaatta atgtgttttt    240
tgtaagttct attaaataca tcagtttaca gcaatgaatt caccattgtg catcgtcaat    300
aaaaggagtg tttatgaaaa atcaatggca acatcaatat tttggatcc                349

<210> SEQ ID NO 91
<211> LENGTH: 373
<212> TYPE: DNA
<213> ORGANISM: Artificial sequence
<220> FEATURE:
<223> OTHER INFORMATION: Promoter / RNA thermometer combination 15

<400> SEQUENCE: 91
ggcgcctttg tggtgatcta cactgatact ctgttgcatt attcgcctga aaccacaata      60
ttcaggcgtt ttttcgctat ctttgacaaa aaatatcaac tttctcgatt tgctctcagc    120
ccttatatca cgggaaattc cggcgatttg ctcgcatcaa tattcatgcc acatttgcca    180
tcaggggccg cctcagattc tcagtatgtt ataatagaaa aaattaatta atgtaaaaaa    240
catcatttag cgtgactttc tttcaacagc taacaattgt tgttactgcc taatgttttt    300
```

-continued

```
agggtatttt aaaaaagggc gataaaaaac gattggggga tgagacatga acgctcaagc      360
agaagaagga tcc                                                         373

<210> SEQ ID NO 92
<211> LENGTH: 362
<212> TYPE: DNA
<213> ORGANISM: Artificial sequence
<220> FEATURE:
<223> OTHER INFORMATION: Promoter / RNA thermometer combination 16

<400> SEQUENCE: 92
ggcgcctttg tggtgatcta cactgatact ctgttgcatt attcgcctga aaccacaata      60
ttcaggcgtt ttttcgctat ctttgacaaa aaatatcaac tttctcgatt tgctctcagc    120
ccttatatca cgggaaattc cggcgatttg ctcgcatcaa tattcatgcc acatttgcca    180 tcagggccg cctcagattc tcagtatgtt ataatagaaa aaattaatta aggcctaatt     240
atagcactta atcgaaataa atttatgagt acgtagagta taattagtat tcttctttcc    300
aacttcctta tacttatata cttatagatt ctaaaatcat gaaacggatt ctttgcggat    360
cc                                                                    362

<210> SEQ ID NO 93
<211> LENGTH: 278
<212> TYPE: DNA
<213> ORGANISM: Artificial sequence
<220> FEATURE:
<223> OTHER INFORMATION: Promoter / RNA thermometer combination 17

<400> SEQUENCE: 93
ggcgccctgg cacaggaacg ttatccggac gttcagttcc accagacccg cgagcattaa     60
ttcttgcctc cagggcgcgg tagtcgcgcc ctgtcaattt cccttcctta ttagccgctt    120
acggaatgtt cttaaaacat tcacttttgc ttatgttttc gctcatatcc cgagcggttt    180
caaaattgtg atctatattt aacaaattaa ttaaacagca attttgcgtt atctgttaat    240
cgagactgaa atacatgaaa aaaccacat taggatcc                             278

<210> SEQ ID NO 94
<211> LENGTH: 454
<212> TYPE: DNA
<213> ORGANISM: Artificial sequence
<220> FEATURE:
<223> OTHER INFORMATION: Promoter / RNA thermometer combination 18

<400> SEQUENCE: 94
ggcgccctgg cacaggaacg ttatccggac gttcagttcc accagacccg cgagcattaa     60
ttcttgcctc cagggcgcgg tagtcgcgcc ctgtcaattt cccttcctta ttagccgctt    120
acggaatgtt cttaaaacat tcacttttgc ttatgttttc gctcatatcc cgagcggttt    180
caaaattgtg atctatattt aacaaattaa ttaaacggtt tgacgtacag accattaaag    240
cagtgtagta aggcaagtcc cttcaagagt tatcgttgat accctcgta gtgcacattc     300 ctttaacgct tcaaaatctg taaagcacgc catatcgccg aaaggcacac ttaattatta    360 aaggtaaatac actatgtccg gtaaaatgac tggtatcgta aaatggttca acgctgacaa    420
aggcttcggc ttcatcactc ctgacgatgg atcc                                454

<210> SEQ ID NO 95
<211> LENGTH: 278
<212> TYPE: DNA
```

<213> ORGANISM: Artificial sequence
<220> FEATURE:
<223> OTHER INFORMATION: Promoter / RNA thermometer combination 19

<400> SEQUENCE: 95

```
ggcgccctgg cacaggaacg ttatccggac gttcagttcc accagacccg cgagcattaa    60
ttcttgcctc cagggcgcgg tagtcgcgcc ctgtcaattt cccttcctta ttagccgctt   120
acggaatgtt cttaaaacat tcacttttgc ttatgttttc gctcatatcc cgagcggttt   180
caaaattgtg atctatattt aacaaattaa ttaaacagca attttgcgtt acctgttaat   240
cgagattgaa acacatgaaa aaaccacat taggatcc                            278
```

<210> SEQ ID NO 96
<211> LENGTH: 282
<212> TYPE: DNA
<213> ORGANISM: Artificial sequence
<220> FEATURE:
<223> OTHER INFORMATION: Promoter / RNA thermometer combination 20

<400> SEQUENCE: 96

```
ggcgccctgg cacaggaacg ttatccggac gttcagttcc accagacccg cgagcattaa    60
ttcttgcctc cagggcgcgg tagtcgcgcc ctgtcaattt cccttcctta ttagccgctt   120
acggaatgtt cttaaaacat tcacttttgc ttatgttttc gctcatatcc cgagcggttt   180
caaaattgtg atctatattt aacaaattaa ttaaattcaa gggtaatcaa ttccttccac   240
acatcaggag ttaacattat gtctctcatt ctttacggat cc                      282
```

<210> SEQ ID NO 97
<211> LENGTH: 309
<212> TYPE: DNA
<213> ORGANISM: Artificial sequence
<220> FEATURE:
<223> OTHER INFORMATION: Promoter / RNA thermometer combination 21

<400> SEQUENCE: 97

```
ggcgccctgg cacaggaacg ttatccggac gttcagttcc accagacccg cgagcattaa    60
ttcttgcctc cagggcgcgg tagtcgcgcc ctgtcaattt cccttcctta ttagccgctt   120
acggaatgtt cttaaaacat tcacttttgc ttatgttttc gctcatatcc cgagcggttt   180
caaaattgtg atctatattt aacaaattaa ttaaggccac tttagtctgt ggttactgta   240
ttaggtattg ttataacaat ctggatggtt tttatgaata agacattact ggtctcttct   300
ttaggatcc                                                           309
```

<210> SEQ ID NO 98
<211> LENGTH: 356
<212> TYPE: DNA
<213> ORGANISM: Artificial sequence
<220> FEATURE:
<223> OTHER INFORMATION: Promoter / RNA thermometer combination 22

<400> SEQUENCE: 98

```
ggcgccctgg cacaggaacg ttatccggac gttcagttcc accagacccg cgagcattaa    60
ttcttgcctc cagggcgcgg tagtcgcgcc ctgtcaattt cccttcctta ttagccgctt   120
acggaatgtt cttaaaacat tcacttttgc ttatgttttc gctcatatcc cgagcggttt   180
caaaattgtg atctatattt aacaaattaa ttaatgtaaa aaacatcatt tagcgtgact   240
ttctttcaac agctaacaat tgttgttact gcctaatgtt tttagggtat tttaaaaaag   300
ggcgataaaa aacgattggg ggatgagaca tgaacgctca agcagaagaa ggatcc       356
```

<210> SEQ ID NO 99
<211> LENGTH: 339
<212> TYPE: DNA
<213> ORGANISM: Artificial sequence
<220> FEATURE:
<223> OTHER INFORMATION: Promoter / RNA thermometer combination 23

<400> SEQUENCE: 99

```
ggcgccaaaa aatattcagt tacaggaaag gtcagggcag ggattctaca gagttctgga      60
taaaatttgt atcgcaatct cattcgctgc cggaggcgaa ggaaatgtaa attttgttaa     120
ttcggcgtga agaattgatc ctggacagca ttttgctcaa aaaatagcca tactatttaa     180
ttgcaacaat taattaatgt aaaaaacatc atttagcgtg actttctttc aacagctaac     240
aattgttgtt actgcctaat gttttttaggg tattttaaaa aagggcgata aaaaacgatt     300
gggggatgag acatgaacgc tcaagcagaa gaaggatcc                            339
```

<210> SEQ ID NO 100
<211> LENGTH: 332
<212> TYPE: DNA
<213> ORGANISM: Artificial sequence
<220> FEATURE:
<223> OTHER INFORMATION: Promoter / RNA thermometer combination 24

<400> SEQUENCE: 100

```
ggcgccctgg cacaggaacg ttatccggac gttcagttcc accagacccg cgagcattaa      60
ttcttgcctc cagggcgcgg tagtcgcgcc ctgtcaattt ccttccttta ttagccgctt     120
acggaatgtt cttaaaacat tcacttttgc ttatgttttc gctcatatcc cgagcggttt     180
caaaattgtg atctatattt aacaaattaa ttaatgtgtt ttttgtaagt tctattaaat     240
acatcagttt acagcaatga attcaccatt gtgcatcgtc aataaaagga gtgtttatga     300
aaaatcaatg gcaacatcaa tattttggat cc                                    332
```

<210> SEQ ID NO 101
<211> LENGTH: 3714
<212> TYPE: DNA
<213> ORGANISM: Artificial sequence
<220> FEATURE:
<223> OTHER INFORMATION: pXH plasmid 1

<400> SEQUENCE: 101

```
gttatccaca gaatcagggg ataacgcagg aaagaacatg tgagcaaaag gccagcaaaa      60
ggccaggaac cgtaaaaagg ccgcgttgct ggcgtttttc catagctcc gcccccctga     120
cgagcatcac aaaaatcgac gctcaagtca gaggtggcga aacccgacag gactataaag     180
ataccaggcg tttccccctg gaagctccct cgtgcgctct cctgttccga ccctgccgct     240
taccggatac ctgtccgcct ttctcccttc gggaagcgtg gcgctttctc atagctcacg     300
ctgtaggtat ctcagttcgg tgtaggtcgt tcgctccaag ctgggctgtg tgcacgaacc     360
ccccgttcag cccgaccgct gcgccttatc cggtaactat cgtcttgagt ccaacccggt     420
aagacacgac ttatcgccac tggcagcagc cactggtaac aggattagca gagcgaggta     480
tgtaggcggt gctacagagt tcttgaagtg gtggcctaac tacggctaca ctagaagaac     540
agtatttggt atctgcgctc tgctgaagcc agttaccttc ggaaaaagag ttggtagctc     600
ttgatccggc aaacaaacca ccgctggtag cggtggtttt tttgtttgca agcagcagat     660
tacgcgcaga aaaaaaggat ctcaagaaga tcctttgatc ttttctacgg ggtctgacgc     720
```

-continued

```
tcagtggaac gaaaactcac gttaagggat tttggtcatg agattatcaa accggtgagg    780
ctatcccgtt ggcggttaat cacccacagc gtgaccagct tgcgctttat tggccagatt    840
ccaggcgaga aacctgacgt gcgagttgca tcaggctatc cgccaaagct ctcggagagg    900
cagtctgggt gttcggagcc agcgtggttt tgcgcttaac gagagatacc ggaagtagtt    960
ggttacccTt caccgcctga ccttgcgaca gttgcagcaa acgatccacg ctcgtttgac   1020
ccagcaaacg aaaatcctgc ttaatggtgg tcaaaggcgg gatgtaacag ctggagtctt   1080
cggtgtcatc ataacccacg acgctgatgt ctgcaccaac acgcaggccg gattcggtaa   1140
tcgcacgcat cgcgcccagc gccatctgat cattcgccac aagcatagcg gtcggaacaa   1200
taccttcgtt cagcatctgc atggtctgct gaaaaccgct cattgctgac caatcgccct   1260
cgcgctcggc aatcggctga atttgattac gcgtcaggta tttatgccaa cccgccagac   1320
gcaggcgagc cgacacgctg ctcagcggac cggcgagcag ggcgatttgc tgatgaccca   1380
gcgcaaccag gtgctccacg cctaatctgg tgccgtcctc gtgggagaag atgatggagt   1440
taatcggagt ttgatcgcta acgtccagga acaatgccgg cacgttggtg cacgcagcct   1500
ccacggcgat tgcgtcctgg tcgtccagcg ggtaattaat aatcaggcct gaaacacgtt   1560
gcgccaacag gttgtgcaca gccgccttgc aggcctcgac accgctgcgt tcaaccatgc   1620
tgacgaccac gctagcaccc aactggtctg cacggctctt gatcgcggcc acgatctgag   1680
acggtgcatg taaggccaag ctgctggtag cgacgccgat cagcaggctc tgtttgccgg   1740
ccagttgttg cgctacacgg ttcgggatgt agttcagttc cgccatcgcc gcctcaactt   1800
tttcacgggt tttcgcgctc acgtggctcg cttgattcac aacgcgggaa actgtctgat   1860
aactaacgcc cgcatactca gcaacatcat atagtgttac gggtttcata ttcaccaccc   1920
tgaattgact ctcttccggg cgctatcatg ccataccgcg aaaggttttg caccattcga   1980
tggtgtccgg gatgagttcc gcaagtgtgc tattcaatgt ttcaccgtag gcgctcactc   2040
ccgatatctt gttattcctc gcagccgcgt taattaccac gacgctatcc ggcttgcttt   2100
agaagaactc gtccagcatc aggtgaaatt gcagtttgtt catgtccggg ttgtcgatac   2160
catacttctg aaataagcgc ttctgcaagg atgggctgaa ctcacccagg caattccata   2220
ggatcgccag atcctgataa cgatcggcga tgcctacacg gcccacgtca atgcagccga   2280
tcagcttacc ctcatcgaag atgaggttat ccagggaaaa atccccatgt gtgaccacgc   2340
tgtccggcga aaacgggagc agtttatgca tttctttcca cacttgttca accggccagc   2400
cattgcgctc gtcgtcgaag tccgatgcat caaccaggcc gttgttcata cggctttgcg   2460
cttgcgccaa gcggaaaacg cgatcggagt tgaacgggca gttgcacacc ggaatgctat   2520
gtaaacgacg caggaacaca gccagggcat caacaatgtt ctcaccgctg tccgggtatt   2580
cttccagaac ctgaaacgcg gtcttacccg ggatcgcggt ggtcaacagc cacgcatcgt   2640
ccggagtgcg gataaagtgt ttaatcgtcg gcagaggcat gaactcggtc aaccagttca   2700
aacgaaccat ctcatccgtg acatcattag cgacagaacc tttaccgtgc ttaagaaaca   2760
gttccggagc gtctggcttg ccgtacagac gataaatggt tgcgccagac tgacccacgt   2820
tatctcttgc ccatttgtag ccgtacaggt ccgcgtccat attgctgttc aaacgcggac   2880
ggctacatga tgtttccctt tgtatgtgac tcataacacc ccttgtatta ctgtttatgt   2940
aagcagacag ttttattgtt catgatgata tatttttatc ttgtgcaatg taacatcaga   3000
gattttgaga cacgggatcg cacaagttca ctagctgaat ccatccgtcc gcctcatcca   3060
gattgaggcg ccggctgggc tggctggcgc ggcttgtcct tgtaatacga ctcactatag   3120
```

-continued

| | |
|---|---|
| gggaattgtg agcggataac aattcccctt aattaagtat attagttaag tataagaagg | 3180 |
| agatatacat atgggaagtt cacatcacca tcaccaccac ggcagcggtg gatccgagaa | 3240 |
| cttgtatttt caaggctcca acgccctcga gtatctgcag agcggccgca tccaattgta | 3300 |
| atcctcaatg gctcggtacc aaattttcga aaaaagacgc tgaaaagcgt cttttttcgt | 3360 |
| tttggtccac tagtcgatgc gttcggcgga tttctccccg gtgctaatac gactcactat | 3420 |
| aggggaattg tgagcggata caattcccc tgtagaaata attttgttta actttaagaa | 3480 |
| ggagatatac catggagatc taatgtcgac atcgagctca tcaagcttat cgttgaattc | 3540 |
| gtcgcgcttc ccaggcatca aataaaacga aggctcagt cgaaagactg ggcctttcgt | 3600 |
| tttatctgtt gtttgtcggt gaacgctctc tactagagtc acactggctc accttcgggt | 3660 |
| gggcctttct gcgtttatag cggatgttag ctaacgtcgt gtttaaggcg cgcc | 3714 |

<210> SEQ ID NO 102
<211> LENGTH: 3547
<212> TYPE: DNA
<213> ORGANISM: Artificial sequence
<220> FEATURE:
<223> OTHER INFORMATION: pXH plasmid 2

<400> SEQUENCE: 102

| | |
|---|---|
| gttatccaca gaatcagggg ataacgcagg aaagaacatg tgagcaaaag gccagcaaaa | 60 |
| ggccaggaac cgtaaaaagg ccgcgttgct ggcgtttttc cataggctcc gcccccctga | 120 |
| cgagcatcac aaaaatcgac gctcaagtca gaggtggcga aacccgacag gactataaag | 180 |
| ataccaggcg tttccccctg gaagctccct cgtgcgctct cctgttccga ccctgccgct | 240 |
| taccggatac ctgtccgcct ttctcccttc gggaagcgtg cgctttctc atagctcacg | 300 |
| ctgtaggtat ctcagttcgg tgtaggtcgt tcgctccaag ctgggctgtg tgcacgaacc | 360 |
| ccccgttcag cccgaccgct gcgccttatc cggtaactat cgtcttgagt ccaacccggt | 420 |
| aagacacgac ttatcgccac tggcagcagc cactggtaac aggattagca gagcgaggta | 480 |
| tgtaggcggt gctacagagt tcttgaagtg gtggcctaac tacggctaca ctagaagaac | 540 |
| agtatttggt atctgcgctc tgctgaagcc agttaccttc ggaaaaagag ttggtagctc | 600 |
| ttgatccggc aaacaaacca ccgctggtag cggtggtttt tttgtttgca agcagcagat | 660 |
| tacgcgcaga aaaaaggat ctcaagaaga tcctttgatc ttttctacgg ggtctgacgc | 720 |
| tcagtggaac gaaaactcac gttaagggat tttggtcatg agattatcaa accggtgagg | 780 |
| ctatcccgtt ggcggttaat cacccacagc gtgaccagct tgcgctttat tggccagatt | 840 |
| ccaggcgaga aacctgacgt gcgagttgca tcaggctatc cgccaaagct ctcggagagg | 900 |
| cagtctgggt gttcggagcc agcgtggttt tgcgcttaac gagagatacc ggaagtagtt | 960 |
| ggttacccctt caccgcctga ccttgcgaca gttgcagcaa cgatccacg ctcgtttgac | 1020 |
| ccagcaaacg aaaatcctgc ttaatggtgg tcaaaggcgg gatgtaacag ctggagtctt | 1080 |
| cggtgtcatc ataacccacg acgctgatgt ctgcaccaac acgcaggccg gattcggtaa | 1140 |
| tcgcacgcat cgcgcccagc gccatctgat cattcgccac aagcatagcg gtcggaacaa | 1200 |
| taccttcgtt cagcatctgc atggtctgct gaaaaccgct cattgctgac caatcgccct | 1260 |
| cgcgctcggc aatcggctga atttgattac gcgtcaggta tttatgccaa cccgccagac | 1320 |
| gcaggcgagc cgacacgctg ctcagcggac cggcagcag ggcgatttgc tgatgaccca | 1380 |
| gcgcaaccag gtgctccacg cctaatctgg tgccgtcctc gtgggagaag atgatggagt | 1440 |

```
taatcggagt ttgatcgcta acgtccagga acaatgccgg cacgttggtg cacgcagcct    1500
ccacggcgat tgcgtcctgg tcgtccagcg ggtaattaat aatcaggcct gaaacacgtt    1560
gcgccaacag gttgtgcaca gccgccttgc aggcctcgac accgctgcgt tcaaccatgc    1620
tgacgaccac gctagcaccc aactggtctg cacggctctt gatcgcggcc acgatctgag    1680
acggtgcatg taaggccaag ctgctggtag cgacgccgat cagcaggctc tgtttgccgg    1740
ccagttgttg cgctacacgg ttcgggatgt agttcagttc cgccatcgcc gcctcaactt    1800
tttcacgggt tttcgcgctc acgtggctcg cttgattcac aacgcgggaa actgtctgat    1860
aactaacgcc cgcatactca gcaacatcat atagtgttac gggtttcata ttcaccaccc    1920
tgaattgact ctcttccggg cgctatcatg ccataccgcg aaaggttttg caccattcga    1980
tggtgtccgg gatgagttcc gcaagtgtgc tattcaatgt ttcaccgtag gcgctcactc    2040
ccgatatctt gttattcctc gcagccgcgt taattaccac gacgctatcc ggcttgcttt    2100
atgcaccgcc ctgccactcg tcgcagtatt gttgcaattc attcagcata cgaccaacat    2160
ggaagccgtc gcacacagcg tggtgaacct gaatcgccag cggcatcaac accttgtcgc    2220
cctgggtgta gtatttaccc attgtaaata ccggagcgaa aaaattatcc atattggcca    2280
cgttcaggtc gaagctggtg aacgaaaccc acgggttcgc agaaacaaaa acatgttttt    2340
cgatgaaacc ttttgggaaa tacgccaggt tctcaccata gcaggcaaca tcttggctgt    2400
agatgtgcaa aaactggcga aagtcatcat gatactcgga ccacaggcta gagaaggttt    2460
ccgtttgttc gtggaacacg gtgtaacacg ggtgcacgga atcccaaata actaactcgc    2520
cgtctttcat agccatgcgg aactccggat gcgcgttcat cagacgcgcc agaatatgga    2580
tgaatgccgg atagaacttg tgcttgttct ttttgacggt cttgagaaat gcggtaatat    2640
ccagctgcac agtctgattg tacgtacact gcgcgacgct ttggaacgcc tcaaaatgtt    2700
ctttacggtg ccattggctg atgtccactg tagtatatcc cgttatcttt ttttccattt    2760
tagcttcctt agctcctgaa aatctcgata actcaaaaaa tacgcccggt agtgatctta    2820
tttcattatg gtgaaagttg gaacctctta tcgcacaagt tcactagctg aatccatccg    2880
tccgcctcat ccagattgag gcgccggctg ggctggctgg cgcggcttgt ccttgtaata    2940
cgactcacta gggggaatt gtgagcggat aacaattccc cttaattaag tatattagtt    3000
aagtataaga aggagatata catatgggaa gttcacatca ccatcaccac cacgcagcg    3060 gtggatccga gaacttgtat tttcaaggct ccaacgccct cgagtatctg cagagcggcc    3120
gcatccaatt gtaatcctca atggctcggt accaaatttt cgaaaaaaga cgctgaaaag    3180
cgtctttttt cgttttggtc cactagtcga tgcgttcggc ggatttctcc ccggtgctaa    3240
tacgactcac tatagggggaa ttgtgagcgg ataacaattc ccctgtagaa ataattttgt    3300
ttaactttaa gaaggagata taccatggag atctaatgtc gacatcgagc tcatcaagct    3360
tatcgttgaa ttcgtcgcgc ttcccaggca tcaaataaaa cgaaaggctc agtcgaaaga    3420
ctgggccttt cgttttatct gttgtttgtc ggtgaacgct ctctactaga gtcacactgg    3480
ctcaccttcg ggtgggcctt tctgcgttta tagcggatgt tagctaacgt cgtgtttaag    3540
gcgcgcc                                                             3547
```

<210> SEQ ID NO 103
<211> LENGTH: 3753
<212> TYPE: DNA
<213> ORGANISM: Artificial sequence
<220> FEATURE:
<223> OTHER INFORMATION: pXH plasmid 3

<400> SEQUENCE: 103

```
gttatccaca gaatcagggg ataacgcagg aaagaacatg tgagcaaaag gccagcaaaa      60
ggccaggaac cgtaaaaagg ccgcgttgct ggcgtttttc cataggctcc gccccctga      120
cgagcatcac aaaaatcgac gctcaagtca gaggtggcga acccgacag gactataaag      180
ataccaggcg tttccccctg gaagctccct cgtgcgctct cctgttccga ccctgccgct     240
taccggatac ctgtccgcct ttctcccttc gggaagcgtg gcgctttctc atagctcacg     300
ctgtaggtat ctcagttcgg tgtaggtcgt tcgctccaag ctgggctgtg tgcacgaacc     360
ccccgttcag cccgaccgct gcgccttatc cggtaactat cgtcttgagt ccaacccggt     420
aagacacgac ttatcgccac tggcagcagc cactggtaac aggattagca gagcgaggta    480
tgtaggcggt gctacagagt tcttgaagtg gtggcctaac tacggctaca ctagaagaac     540
agtatttggt atctgcgctc tgctgaagcc agttaccttc ggaaaaagag ttggtagctc     600
ttgatccggc aaacaaacca ccgctggtag cggtggtttt tttgtttgca agcagcagat    660
tacgcgcaga aaaaaggat ctcaagaaga tcctttgatc ttttctacgg gtctgacgc      720
tcagtggaac gaaaactcac gttaagggat tttggtcatg agattatcaa accggtgagg    780
ctatcccgtt ggcggttaat cacccacagc gtgaccagct tgcgctttat tggccagatt    840
ccaggcgaga aacctgacgt gcgagttgca tcaggctatc cgccaaagct ctcggagagg    900
cagtctgggt gttcggagcc agcgtggttt tgcgcttaac gagagatacc ggaagtagtt    960
ggttacccctt caccgcctga ccttgcgaca gttgcagcaa acgatccacg ctcgtttgac   1020
ccagcaaacg aaaatcctgc ttaatggtgg tcaaaggcgg gatgtaacag ctggagtctt   1080
cggtgtcatc ataacccacg acgctgatgt ctgcaccaac acgcaggccg gattcggtaa   1140
tcgcacgcat cgcgcccagc gccatctgat cattcgccac aagcatagcg gtcggaacaa   1200
taccttcgtt cagcatctgc atggtctgct gaaaaccgct cattgctgac caatcgccct   1260
cgcgctcggc aatcggctga atttgattac gcgtcaggta tttatgccaa cccgccagac   1320
gcaggcgagc cgacacgctg ctcagcggac cggcgagcag ggcgatttgc tgatgaccca   1380
gcgcaaccag gtgctccacg cctaatctgg tgccgtcctc gtgggagaag atgatggagt   1440
taatcggagt ttgatcgcta acgtccagga acaatgccgg cacgttggtg cacgcagcct   1500
ccacggcgat tgcgtcctgg tcgtccagcg ggtaattaat aatcaggcct gaaacacgtt   1560
gcgccaacag gttgtgcaca gccgccttgc aggcctcgac accgctgcgt tcaaccatgc   1620
tgacgaccac gctagcaccc aactggtctg cacggctctt gatcgcggcc acgatctgag   1680
acggtgcatg taaggccaag ctgctggtag cgacgccgat cagcaggctc tgtttgccgg   1740
ccagttgttg cgctacacgg ttcgggatgt agttcagttc cgccatcgcc gcctcaactt   1800
tttcacgggt tttcgcgctc acgtggctcg cttgattcac aacgcgggaa actgtctgat   1860
aactaacgcc cgcatactca gcaacatcat atagtgttac gggtttcata ttcaccaccc   1920
tgaattgact ctcttccggg cgctatcatg ccataccgcg aaaggttttg caccattcga   1980
tggtgtccgg gatgagttcc gcaagtgtgc tattcaatgt ttcaccgtag gcgctcactc   2040
ccgatatctt gttattcctc gcagccgcgt taattaccac gacgctatcc ggcttgcttt   2100
agaagaactc gtccagcatc aggtgaaatt gcagtttgtt catgtccggg ttgtcgatac   2160
catacttctg aaataagcgc ttctgcaagg atgggctgaa ctcacccagg caattccata   2220
ggatcgccag atcctgataa cgatcggcga tgcctacacg gcccacgtca atgcagccga   2280
```

| | |
|---|---|
| tcagcttacc ctcatcgaag atgaggttat ccagggaaaa atccccatgt gtgaccacgc | 2340 |
| tgtccggcga aaacgggagc agtttatgca tttctttcca cacttgttca accggccagc | 2400 |
| cattgcgctc gtcgtcgaag tccgatgcat caaccaggcc gttgttcata cggctttgcg | 2460 |
| cttgcgccaa gcggaaaacg cgatcggagt tgaacgggca gttgcacacc ggaatgctat | 2520 |
| gtaaacgacg caggaacaca gccagggcat caacaatgtt ctcaccgctg tccgggtatt | 2580 |
| cttccagaac ctgaaacgcg gtcttacccg ggatcgcggt ggtcaacagc cacgcatcgt | 2640 |
| ccggagtgcg gataaagtgt ttaatcgtcg gcagaggcat gaactcggtc aaccagttca | 2700 |
| aacgaaccat ctcatccgtg acatcattag cgacagaacc tttaccgtgc ttaagaaaca | 2760 |
| gttccggagc gtctggcttg ccgtacagac gataaatggt tgcgccagac tgacccacgt | 2820 |
| tatctcttgc ccatttgtag ccgtacaggt ccgcgtccat attgctgttc aaacgcggac | 2880 |
| ggctacatga tgtttccctt tgtatgtgac tcataacacc ccttgtatta ctgtttatgt | 2940 |
| aagcagacag ttttattgtt catgatgata tattttatc ttgtgcaatg taacatcaga | 3000 |
| gattttgaga cacgggatcg cacaagttca ctagctgaat ccatccgtcc gcctcatcca | 3060 |
| gattgaggcg ccaaattttc gaaaaaagac gctgaaaagc gtcttttttc gttttggtcc | 3120 |
| cgatgcgttc ggcggatttc tccccggtgc taatacgact cactataggg gaattgtgag | 3180 |
| cggataacaa ttcccctgta gaaataattt tgtttaactt taagaaggag atatacatat | 3240 |
| gggaagttca catcaccatc accaccacg cagcggtgga tccgagaact tgtatttca | 3300 |
| aggctccaac gccctcgagt atctgcagag cggccgcatc caattgtaat cctcaatggc | 3360 |
| caggcatcaa ataaaacgaa aggctcagtc gaaagactgg gcctttcgtt ttatctgttg | 3420 |
| tttgtcggtg aacgctctct actagagtca cactggctca ccttcgggtg ggcctttctg | 3480 |
| cgtttataac tagtggctgg gctggctggc gcggcttgtc cttgtaatac gactcactat | 3540 |
| aggggaattg tgagcggata caattcccc tgtagaaata attttgttta actttaataa | 3600 |
| ggagatatac catggagatc taatgtcgac atcgagctca tcaagcttat cgttgaattc | 3660 |
| gtcgcgcttc ctagcataac cccttgggc ctctaaacgg gtcttgaggg gttttttggc | 3720 |
| ggatgttagc taacgtcgtg tttaaggcgc gcc | 3753 |

```
<210> SEQ ID NO 104
<211> LENGTH: 3584
<212> TYPE: DNA
<213> ORGANISM: Artificial sequence
<220> FEATURE:
<223> OTHER INFORMATION: pXH plasmid 4

<400> SEQUENCE: 104
```

| | |
|---|---|
| gttatccaca gaatcagggg ataacgcagg aaagaacatg tgagcaaaag gccagcaaaa | 60 |
| ggccaggaac cgtaaaaagg ccgcgttgct ggcgtttttc cataggctcc gcccccctga | 120 |
| cgagcatcac aaaaatcgac gctcaagtca gaggtggcga aacccgacag gactataaag | 180 |
| ataccaggcg tttccccctg gaagctccct cgtgcgctct cctgttccga cctgccgct | 240 |
| taccggatac ctgtccgcct ttctcccttc gggaagcgtg cgctttctc atagctcacg | 300 |
| ctgtaggtat ctcagttcgg tgtaggtcgt tcgctccaag ctgggctgtg tgcacgaacc | 360 |
| ccccgttcag cccgaccgct gcgccttatc cggtaactat cgtcttgagt ccaacccggt | 420 |
| aagacacgac ttatcgccac tggcagcagc cactggtaac aggattagca gagcgaggta | 480 |
| tgtaggcggt gctacagagt tcttgaagtg gtggcctaac tacggctaca ctagaagaac | 540 |
| agtatttggt atctgcgctc tgctgaagcc agttaccttc ggaaaaagag ttggtagctc | 600 |

```
ttgatccggc aaacaaacca ccgctggtag cggtggtttt tttgtttgca agcagcagat    660
tacgcgcaga aaaaaaggat ctcaagaaga tcctttgatc ttttctacgg ggtctgacgc    720
tcagtggaac gaaaactcac gttaagggat tttggtcatg agattatcaa accggtgagg    780
ctatcccgtt ggcggttaat cacccacagc gtgaccagct tgcgctttat tggccagatt    840
ccaggcgaga aacctgacgt gcgagttgca tcaggctatc cgccaaagct ctcggagagg    900
cagtctgggt gttcggagcc agcgtggttt tgcgcttaac gagagatacc ggaagtagtt    960 ggttacccctt caccgcctga ccttgcgaca gttgcagcaa acgatccacg ctcgtttgac   1020
ccagcaaacg aaaatcctgc ttaatggtgg tcaaaggcgg gatgtaacag ctggagtctt   1080
cggtgtcatc ataacccacg acgctgatgt ctgcaccaac acgcaggccg gattcggtaa   1140
tcgcacgcat cgcgcccagc gccatctgat cattcgccac aagcatagcg gtcggaacaa   1200
taccttcgtt cagcatctgc atggtctgct gaaaaccgct cattgctgac caatcgccct   1260
cgcgctcggc aatcggctga atttgattac gcgtcaggta tttatgccaa cccgccagac   1320
gcaggcgagc cgacacgctg ctcagcggac cggcgagcag ggcgatttgc tgatgaccca   1380
gcgcaaccag gtgctccacg cctaatctgg tgccgtcctc gtgggagaag atgatggagt   1440
taatcggagt ttgatcgcta acgtccagga acaatgccgg cacgttggtg cacgcagcct   1500
ccacggcgat tgcgtcctgg tcgtccagcg ggtaattaat aatcaggcct gaaacacgtt   1560
gcgccaacag gttgtgcaca gccgccttgc aggcctcgac accgctgcgt tcaaccatgc   1620
tgacgaccac gctagcaccc aactggtctg cacggctctt gatcgcggcc acgatctgag   1680
acggtgcatg taaggccaag ctgctggtag cgacgccgat cagcaggctc tgtttgccgg   1740
ccagttgttg cgctacacgg ttcgggatgt agttcagttc cgccatcgcc gcctcaactt   1800
tttcacgggt tttcgcgctc acgtggctcg cttgattcac aacgcgggaa actgtctgat   1860
aactaacgcc cgcatactca gcaacatcat atagtgttac gggtttcata ttcaccaccc   1920
tgaattgact ctcttccggg cgctatcatg ccataccgcg aaaggttttg caccattcga   1980
tggtgtccgg gatgagttcc gcaagtgtgc tattcaatgt ttcaccgtag gcgctcactc   2040
ccgatatctt gttattcctc gcagccgcgt taattaccac gacgctatcc ggcttgcttt   2100
atgcaccgcc ctgccactcg tcgcagtatt gttgcaattc attcagcata cgaccaacat   2160
ggaagccgtc gcacacagcg tggtgaacct gaatcgccag cggcatcaac accttgtcgc   2220
cctgggtgta gtatttaccc attgtaaata ccggagcgaa aaaattatcc atattggcca   2280
cgttcaggtc gaagctggtg aacgaaaccc acgggttcgc agaaacaaaa acatgttttt   2340
cgatgaaacc ttttgggaaa tacgccaggt tctcaccata gcaggcaaca tcttggctgt   2400
agatgtgcaa aaactggcga aagtcatcat gatactcgga ccacaggcta gagaaggttt   2460
ccgtttgttc gtggaacacg gtgtaacacg ggtgcacgga atcccaaata actaactcgc   2520
cgtctttcat agccatgcgg aactccggat gcgcgttcat cagacgcgcc agaatatgga   2580
tgaatgccgg atagaacttg tgcttgttct ttttgacggt cttgagaaat gcggtaatat   2640
ccagctgcac agtctgattg tacgtacact gcgcgacgct ttggaacgcc tcaaaatgtt   2700
ctttacggtg ccattggctg atgtccactg tagtatatcc cgttatcttt ttttccattt   2760
tagcttcctt agctcctgaa aatctcgata actcaaaaaa tacgcccggt agtgatctta   2820
tttcattatg gtgaaagttg gaacctctta tcgcacaagt tcactagctg aatccatccg   2880
tccgcctcat ccagattggc gccaaatttt cgaaaaaaga cgctgaaaag cgtctttttt   2940
```

-continued

```
cgttttggtc cgatgcgtt cggcggattt ctccccggtg ctaatacgac tcactatagg   3000
ggaattgtga gcggataaca attcccctgt agaaataatt ttgtttaact ttaagaagga   3060
gatatacata tgggaagttc acatcaccat caccaccacg gcagcggtgg atccgagaac   3120
ttgtattttc aaggctccaa cgccctcgag tatctgcaga gcggccgcat ccaattgtaa   3180
tcctcaatgg ccaggcatca aataaaacga aaggctcagt cgaaagactg ggcctttcgt   3240
tttatctgtt gtttgtcggt gaacgctctc tactagagtc acactggctc accttcgggt   3300
gggcctttct gcgtttataa ctagtggctg gctggctgg cgcggcttgt ccttgtaata   3360
cgactcacta tagggaatt gtgagcggat aacaattccc ctgtagaaat aattttgttt   3420
aactttaata aggagatata ccatggagat ctaatgtcga catcgagctc atcaagctta   3480
tcgttgaatt cgtcgcgctt cctagcataa ccccttgggg cctctaaacg ggtcttgagg   3540
ggttttttgg cggatgttag ctaacgtcgt gtttaaggcg cgcc               3584
```

<210> SEQ ID NO 105
<211> LENGTH: 29
<212> TYPE: RNA
<213> ORGANISM: Artificial sequence
<220> FEATURE:
<223> OTHER INFORMATION: RNA thermometer 10

<400> SEQUENCE: 105

```
ggaucccucc uucagaagga gauauaccc                              29
```

<210> SEQ ID NO 106
<211> LENGTH: 59
<212> TYPE: RNA
<213> ORGANISM: Artificial sequence
<220> FEATURE:
<223> OTHER INFORMATION: RNA thermometer 11

<400> SEQUENCE: 106

```
ggauccucuc cuucacuagu aaaaaaaaaa aaaaaaaaa aaaaaaagga gauauaccc   59
```

<210> SEQ ID NO 107
<211> LENGTH: 29
<212> TYPE: RNA
<213> ORGANISM: Artificial sequence
<220> FEATURE:
<223> OTHER INFORMATION: RNA thermometer 12

<400> SEQUENCE: 107

```
ggauccucuc cuuagaagga gauauaccc                              29
```

<210> SEQ ID NO 108
<211> LENGTH: 38
<212> TYPE: RNA
<213> ORGANISM: Artificial sequence
<220> FEATURE:
<223> OTHER INFORMATION: RNA thermometer 13

<400> SEQUENCE: 108

```
ggaucccucc uuacuagucu gcagaaggag auauaccc                     38
```

<210> SEQ ID NO 109
<211> LENGTH: 39
<212> TYPE: RNA
<213> ORGANISM: Artificial sequence
<220> FEATURE:
<223> OTHER INFORMATION: RNA thermometer 14

```
<400> SEQUENCE: 109
ggauccucuc cuuacuaguc ugcagaagga gauauaccc                    39

<210> SEQ ID NO 110
<211> LENGTH: 39
<212> TYPE: RNA
<213> ORGANISM: Artificial sequence
<220> FEATURE:
<223> OTHER INFORMATION: RNA thermometer 15

<400> SEQUENCE: 110
ggaucccucc uucacuaguc ugcagaagga gauauaccc                    39

<210> SEQ ID NO 111
<211> LENGTH: 61
<212> TYPE: RNA
<213> ORGANISM: Artificial sequence
<220> FEATURE:
<223> OTHER INFORMATION: RNA thermometer 16

<400> SEQUENCE: 111
uaaauacauc aguuuacagc aaugaauuca ccauugugca ucgucaauaa aaggaguguu    60
u                                                             61
```

FLUORESCENT FUSION BASED HETEROLOGOUS PEPTIDE PRODUCTION

CROSS-REFERENCE TO RELATED APPLICATIONS

This application is a US national stage application of International Patent Application No. PCT/IB2021/060587, filed Nov. 16, 2021, which claims priority to South African Application No. 2020/07119, filed Nov. 16, 2020, each of which is incorporated in its entirety by reference herein.

SEQUENCE LISTING

The present application is filed with a Sequence Listing in electronic format. The Sequence Listing is provided as a file entitled "PCT_Sequence_Listing" created on Nov. 16, 2021, which is 103,400 bytes in size. The information in the electronic format of the sequence listing is incorporated herein by reference in its entirety.

BACKGROUND OF THE INVENTION

This invention relates to a method of producing a heterologous polypeptide of interest in a host cell, wherein the method comprises expressing a fusion protein comprising the heterologous polypeptide of interest and a fluorescent fusion partner in a host cell modified to include a nucleic acid encoding a lytic protein, under control of an RNA thermometer. The invention further relates to E. coli cells which express the fusion protein and include a nucleic acid encoding a lytic protein under control of an RNA thermometer.

Peptides are ubiquitous in physiological systems where they fulfil functions which are fundamental to life. Within human physiology alone, peptides function as hormones, neurotransmitters, growth factors, ion channel ligands or antimicrobials which makes them an attractive therapeutic resource.

There is an increasing need for new pharmaceuticals and industrial enzymes which, as a result of next generation sequencing, is creating a market of researchers observing peptides or proteins they would like to test for pharmaceutical or industrial properties. Additionally, current production of valuable recombinant proteins will always find benefit in technologies that can improve both yield and productivity. Therefore, technologies like protein synthesis and heterologous protein expression are gaining application.

Peptides and small proteins of interest are often chemically synthesised which produces far better yields compared to heterologous expression. While heterologous expression is an established technology which makes use of a heterologous host, better suited for high yield production but still governed by the elusive physical laws which guide protein folding or post translational modifications. Heterologous expression should therefore work hand in hand with chemical synthesis by providing the physical structure from a genetic blueprint, which is obvious to many in this field. However, bioactive proteins are challenging to express due to their inherent physical properties which make them good pharmaceutical and enzyme candidates to begin with. Therefore, expression of these proteins requires specific expertise and technologies, which often results in a preference for chemical synthesis of multiple iterations or classical purification. Both approaches can result in an increase in the time and resources required for pharmaceutical characterisation. The present invention aims to provide a robust and rapid platform to push the boundaries of heterologous expression in both target variety and yield. Specifically, the inventors of the present application have developed a method for producing a wide range of recombinant proteins. The method relies on three key technologies linked together to make it versatile and cost-effective for increasing the production of various recombinant proteins it produces. The method of the present invention uses a fluorescent protein fusion partner which aims to enable stabilized peptide expression which broadens the capabilities of E. coli through quenching toxicity, increasing solubility and promoting post translational modification. Autofluorescence of the fusion partner enables rapid optimization which boosts yields by supplying unprecedented real time in vivo and robust in vitro feedback. In addition, post transcriptional thermoregulation of autolysis reduces production cost, time and effort, making the method faster and more cost-effective than conventional methods. Using the method of the present invention, the inventors have shown that they are able to 1) increase the range and yield of the recombinant proteins expressed where previously considered fruitless; 2) simplify the optimization of expression by in vivo detection of the fluorescent fusion protein; 3) reduce time spent on troubleshooting through the ability to quickly visualize the fluorescent protein at any point during production; and 4) reduce protein production costs and increase yield though the implementation of autolysis technologies that do not require expensive inducers.

SUMMARY OF THE INVENTION

The present invention relates to a method for producing a heterologous polypeptide of interest in a host cell, preferably an E. coli cell, comprising expressing a fusion protein including the heterologous polypeptide of interest and a fluorescent fusion partner in the host cell. In particular, the host cell is modified to include a nucleic acid encoding a lytic protein, which is under control of an RNA thermometer. The invention also relates to modified E. coli cells which express the fusion protein of the invention, and which include a nucleic acid encoding a lytic protein that is under control of an RNA thermometer.

According to a first aspect of the present invention there is provided for a method of producing one or more heterologous polypeptides of interest in a host cell, the method comprising or consisting of:
  (i) providing an expression vector encoding a fusion protein comprising the heterologous polypeptide of interest and a fluorescent fusion partner;
  (ii) transforming the host cell with the expression vector of step (i), wherein the host cell and/or the expression vector is modified to include a nucleic acid encoding a promoter (may be constitutive e.g. stationary phase promotor, or inducible e.g. T7) operably linked to a lytic protein, and an RNA thermometer, further wherein expression of the nucleic acid encoding the lytic protein is regulated by the promoter and translation of the lytic protein is regulated by the RNA thermometer;
  (iii) expressing the fusion protein in the host cell;
  (iv) modifying the temperature of the host cell to induce expression of the lytic protein, wherein expression of the lytic protein results in lysis of the host cell; and
  (v) recovering the fusion protein from the host cell.

Preferably, the nucleic acid encoding the RNA thermometer is transcriptionally fused to the promoter and transcriptionally or translationally fused to the nucleic acid encoding the lytic protein. More preferably, the nucleic acid encoding the RNA thermometer is upstream of the nucleic acid encoding the lytic protein. Further, the nucleic acid encoding the promoter, the lytic protein and the RNA thermometer may include a nucleotide sequence that is recognised by the RNA thermometer, such as a nucleotide sequence that the RNA natively recognises and controls.

In a first embodiment of the method, the fusion protein may include a purification tag and the method may further comprise a step of purifying the recovered fusion protein. It will be appreciated by those of skill in the art that any known purification tag may be used. Preferably, the purification tag may be a histidine (His) tag for use in immobilized metal affinity chromatography (IMAC) purification or a Glutathione S-transferase (GST) tag for use in a pull-down assay. Alternatively, the fusion protein may comprise more than one purification tag, such as a histidine (His) tag for use in IMAC purification and a Glutathione S-transferase (GST) tag for use in a pull-down assay.

According to a second embodiment of the method of the invention the fusion protein may include a protease cleavage site and the method may further comprise a step of cleaving the fluorescent fusion partner from the heterologous polypeptide of interest after recovery. It will be appreciated by those of skill in the art that any known protease cleavage site may be contemplated, for cleavage by a protease. In particular, the protease cleavage site may be selected from the group consisting of a WELQut site having the amino acid sequence WELQ (SEQ ID NO:1) encoded by a nucleic acid having the sequence TGGGAACTGCAG (SEQ ID NO:2), a thrombin or trypsin cleavage site having the amino acid sequence LVPR (SEQ ID NO:3) encoded by a nucleic acid having the sequence CTAGTACCACGC (SEQ ID NO:4), a nisP or trypsin cleavage site having the amino acid sequence ASPR (SEQ ID NO:5) encoded by a nucleic acid having the sequence GCGAGCCCGCGC (SEQ ID NO:6), a TEV cleavage site having the amino acid sequence ENLYFQG (SEQ ID NO:7) encoded by a nucleic acid having the sequence GAAAACTTGTATTTTCAAGGC (SEQ ID NO:8), a Factor Xa cleavage site having the amino acid sequence IEGR (SEQ ID NO:9) encoded by a nucleic acid having the sequence ATTGAAGGTCGT (SEQ ID NO:10), and any combination thereof.

In a third embodiment of the method of the invention, the fusion protein may include a secretion peptide. Signal peptides that may be used can include, but are not limited to, those that direct secretion via the Sec (general secretory), SRP (signal recognition particle) or TAT (twin arginine translocation) pathways. For Sec dependent secretion, sequences from LamB, MalE, OmpA, OmpF, OmpT or PhoA can be used. For SRP dependent secretion, sequences from DsbA, SfmC, TolB or TorT can be used. For TAT-dependent secretion, the signal peptide can be variable and contain the P-R-R-x-H-H motif (where P, R, x and H indicate a Polar residue, arginine, any residue and hydrophobic residue, respectively). Signal peptides can be homologous to *E. coli* or heterologous sequences from other species such as PelB (*Erwinia carotovora*) and SpA (*Staphylococcus*).

According to a fourth embodiment of the method of the present invention, the fluorescent fusion partner is preferably monomeric and may be selected from the group consisting of green fluorescent protein, yellow fluorescent protein, blue fluorescent protein, cyan fluorescent protein, and a red fluorescent protein. It will be appreciated by those of skill in the art that numerous fluorescent fusion proteins are known and that any fluorescent fusion protein known in the art may be used. For example, the fluorescent fusion partner may be a green fluorescent protein having the amino acid sequence of SEQ ID NO: 11 or being encoded by a nucleic acid having the nucleotide sequence of SEQ ID NO: 12. Alternatively, the fluorescent fusion partner may be a red fluorescent protein, such as mCherry having the amino acid sequence of SEQ ID NO: 13 or being encoded by a nucleic acid having the nucleotide sequence of SEQ ID NO: 14. It will be appreciated by those of skill in the art that the method of the invention may include a step of detecting the fluorescent fusion partner at any point.

In a further embodiment of the method of the invention, the heterologous polypeptide of interest may be any heterologous polypeptide of interest, in particular a heterologous polypeptide of interest selected from the group consisting of a lanthipeptide, including Nisin, epilancin 15X and Pep5; a bacteriocin, including plantaricin 423 and mundticin ST4SA; Listeriolysin O; ActA; and autophagic peptideX.

In another embodiment of the method of the present invention, the lytic protein may be any lytic protein known in the art, for example the lytic protein may be endolysin or bacterial murein hydrolase. In one non-limiting example, the lytic protein originates from phage DNA and has the amino acid sequence of SEQ ID NO: 15 or 17 or is encoded by a nucleic acid having the nucleotide sequence of SEQ ID NO: 16 or 18.

In yet a further embodiment of the method of the invention, the RNA thermometer may include, but is not limited to, an RNA thermometer having the nucleic acid sequence of any one of SEQ ID NOs: 19-27 or SEQ ID NOs: 105-111. The RNA thermometer can be naturally occurring, such as those found in lambda phage and bacteria, or can be synthesized as a novel sequence. Furthermore, the use of a constitutive promoter (e.g. stationary phase promoters) or inducible promoter (e.g. T7) may be used to control the transcription of the nucleic acid encoding the RNA thermometer and lytic gene. The use of stationary phase promoters can result in delayed transcription of the mRNA consisting of the RNA thermometer and lytic gene. This allows for increased stability of the mRNA and reduce the metabolic load on the cell through delayed expression of the lysis gene. Suitable stationary phase promoters may include a promoter having the nucleic acid sequence of any one of SEQ ID NOs: 74-76. Further, suitable combinations of promoters and RNA thermometers may include a combination having a sequence as shown in any one of SEQ ID NOs: 77-100.

According to a further embodiment of the method of the invention, the host cell may be an *E. coli* cell.

According to a second aspect of the present invention there is provided for an *E. coli* cell comprising: (i) at least one expression vector (including a vector having a sequence as shown in SEQ ID NO: 101 or SEQ ID NO:102) encoding a fusion protein comprising a heterologous polypeptide of interest and a fluorescent fusion partner; and (ii) a nucleic acid encoding a promoter operably linked to a lytic protein and an RNA thermometer, wherein the RNA thermometer is capable of regulating translation of the lytic protein. In one embodiment, the nucleic acid in (ii) may be provided on the expression vector of (i). In an alternative embodiment, the nucleic acid of (ii) may be provided on a different expression vector which is compatible, and co-transformed, with the expression vector of (i).

In a first embodiment of the cell of the invention, the fusion protein may include a purification tag for use in purifying the fusion protein. It will be appreciated by those of skill in the art that any known purification tag may be used. Preferably, the purification tag may be a histidine (His)

tag for use in IMAC purification or a Glutathione S-transferase (GST) tag for use in a pull-down assay. Alternatively, the fusion protein may comprise more than one purification tag, such as a histidine (His) tag for use in IMAC purification and a Glutathione S-transferase (GST) tag for use in a pull-down assay.

According to a second embodiment of the cell of the invention, the fusion protein may include a protease cleavage site for use in cleaving the fluorescent fusion partner from the heterologous polypeptide of interest. It will be appreciated by those of skill in the art that any known protease cleavage site may be used for cleavage by a protease. In particular, the protease cleavage site may be selected from the group consisting of a WELQut site having the amino acid sequence WELQ (SEQ ID NO:1) encoded by a nucleic acid having the sequence TGGGAACTGCAG (SEQ ID NO:2), a thrombin or trypsin cleavage site having the amino acid sequence LVPR (SEQ ID NO: 3) encoded by a nucleic acid having the sequence CTAGTACCACGC (SEQ ID NO: 4), a nisP or trypsin cleavage site having the amino acid sequence ASPR (SEQ ID NO: 5) encoded by a nucleic acid having the sequence GCGAGCCCGCGC (SEQ ID NO: 6), a TEV cleavage site having the amino acid sequence ENLYFQG (SEQ ID NO: 7) encoded by a nucleic acid having the sequence GAAAACTTGTATTTT-CAAGGC (SEQ ID NO:8), a Factor Xa cleavage site having the amino acid sequence IEGR (SEQ ID NO:9) encoded by a nucleic acid having the sequence ATTGAAGGTCGT (SEQ ID NO: 10), and any combination thereof.

In a third embodiment of the cell of the invention, the fusion protein may include a secretion peptide.

According to a fourth embodiment of the cell of the present invention, the fluorescent fusion partner may be selected from the group consisting of green fluorescent protein, yellow fluorescent protein, blue fluorescent protein, cyan fluorescent protein, and a red fluorescent protein. It will be appreciated by those of skill in the art that numerous fluorescent fusion proteins are known, and that any fluorescent fusion protein known in the art may be used. For example, the fluorescent fusion partner may be a green fluorescent protein having the amino acid sequence of SEQ ID NO: 11 or encoded by the nucleotide sequence of SEQ ID NO: 12. Alternatively, the fluorescent fusion partner may be a red fluorescent protein, such as mCherry having the amino acid sequence of SEQ ID NO: 13 or encoded by the nucleotide sequence of SEQ ID NO: 14.

In a further embodiment of the cell of the invention, the heterologous polypeptide of interest may be any heterologous polypeptide of interest, for example a heterologous polypeptide of interest selected from the group consisting of a lanthipeptide, including Nisin, epilancin 15X and Pep5; a bacteriocins, including plantaricin 423 and mundticin ST4SA; Listeriolysin O; ActA; and autophagic peptideX.

According to a further embodiment of the cell of the present invention, the lytic protein may be any lytic protein known in the art, for example the lytic protein may be endolysin or bacterial murein hydrolase. In one non-limiting example, the lytic protein originates from phage DNA and has the amino acid sequence of SEQ ID NO: 15 or 17 or is encoded by the nucleotide sequence of SEQ ID NO: 16 or 18.

In yet a further embodiment of the cell of the invention, the RNA thermometer may include, but is not limited to, an RNA thermometer having the nucleic acid sequences of any one of SEQ ID NOs: 19-27 or SEQ ID NOs: 105-111. The RNA thermometer can be naturally occurring, such as those found in lambda phage and bacteria, or can be synthesized as a novel sequence. The promoter controlling the expression of the RNA thermometer and lytic protein may be a constitutive promoter (e.g. a stationary phase promoter having a sequence as shown in any one of SEQ ID NOs: 74-76) or an inducible promoter (e.g. T7). Further, suitable combinations of promoters and RNA thermometers may include a combination having a sequence as shown in any one of SEQ ID NOs: 77-100.

According to a third aspect of the present invention there is provided for a kit comprising or consisting of: (i) at least one expression vector for expressing a fusion protein comprising a heterologous polypeptide of interest and a fluorescent fusion partner; and (ii) an E. coli cell, wherein the cell and/or the expression vector comprises a nucleic acid encoding a promoter (including a constitutive promoter e.g. stationary phase promotor, or an inducible promoter e.g. T7) operably linked to a lytic protein, and an RNA thermometer, wherein the RNA thermometer is capable of regulating translation of the lytic protein.

BRIEF DESCRIPTION OF THE FIGURES

Non-limiting embodiments of the invention will now be described by way of example only and with reference to the following figures:

FIG. 3: Sequence of GFP-pNisin (SEQ ID NO:29 and SEQ ID NO:31) including relevant restriction sites and protease cleavage sites. The corresponding amino acid sequences are shown (SEQ ID NO:28 and SEQ ID NO:30) Amino acid and nucleotide changes of cleavage sites for hNisP (AVPR) and thrombin (ASPR) are shown. GFP and prenisin amino acid sequences are indicated with prenisin leader sequence underlined.

FIGS. 15A-15D: SDS-PAGE analysis of WELQut cleaved GFP-PlaX (15A and 15B) and GFP-MunX (15C and 15D). (15A and 15C) represent unstained SDS-PAGE gels fluorometrically photographed. (15B and 15D) represent stained gels of (15A and 15C). Lane: 1-Ladder, 2-uncleaved sample, 3 to 6 WELQut cleavage samples, sample ratios indicated. Band I—Uncleaved GFP-PlantEx, II—putative WELQut and GFP complex, III—WELQut, IV—Uncleaved GFP-MunX, V—putative WELQut and GFP complex, VI—WELQut.

DETAILED DESCRIPTION OF THE INVENTION

Figure 1:
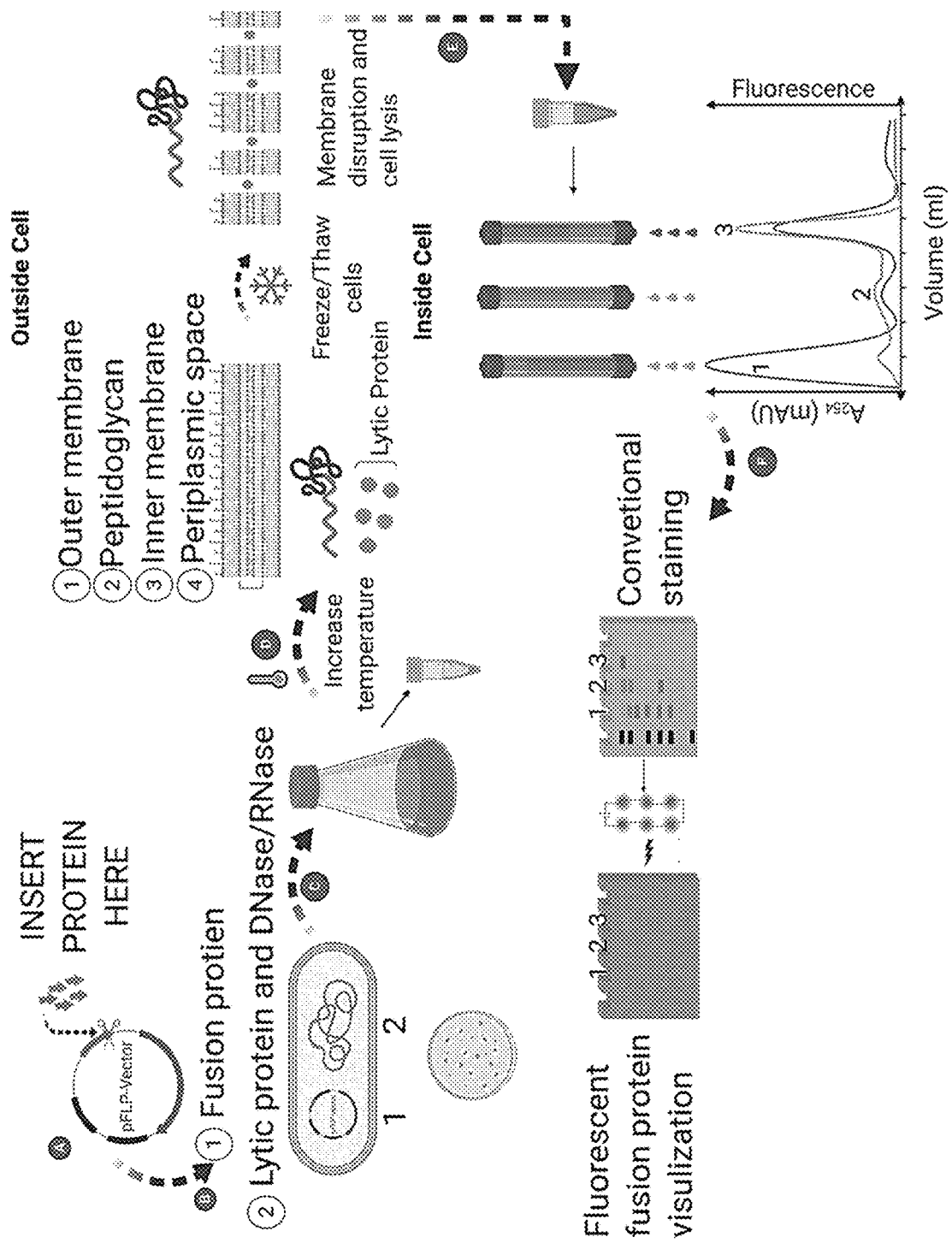
FIG. 1: Schematic of the method of heterologous protein production. A) Vector construction; B) Transformation; C) Expression; D) Cell lysis; E) Purification and F) Visualization. A nucleic acid molecule encoding a fluorescent fusion partner and a peptide of interest (PoI) are cloned into a vector. The vector is expressed in an E. coli cell. Specifically, expression of the fluorescent fusion partner is detected by monitoring the fluorescence thereof, which provides an indication of the expression of the protein of interest. Once the peptide of interest accumulates, as indicated by the detection of the fluorescent fusion partner, temperature dependent expression of a lytic protein is initiated by increasing the temperature. The presence of the lytic protein causes cell membrane disruption and cell lysis upon a freeze thaw cycle, which results in the release of the peptide of interest and the fluorescent fusion partner. The peptide of interest and the fluorescent fusion partner may optionally be purified. Yield of the peptide of interest may be monitored by detecting the fluorescent fusion partner at all stages, including visualisation of the purified product.

The present invention will now be described more fully hereinafter with reference to the accompanying drawings, in which some, but not all embodiments of the invention are shown.

The invention as described should not be limited to the specific embodiments disclosed and modifications and other embodiments are intended to be included within the scope of the invention. Although specific terms are employed herein, they are used in a generic and descriptive sense only and not for purposes of limitation.

As used throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having" and "including" and variations thereof used herein, are meant to encompass the items listed thereafter and equivalents thereof as well as additional items.

The present invention relates to a method of producing a heterologous polypeptide of interest in a host cell, comprising expressing a fusion protein comprising the heterologous polypeptide of interest and a fluorescent fusion partner in a host cell. The host cell is modified to include a nucleic acid encoding a lytic protein. In order to reduce the metabolic load imposed by the lytic protein this protein is under control of an RNA thermometer. The invention also relates to *E. coli* cells which express the fusion protein and include the nucleic acid encoding a lytic protein under control of an RNA thermometer.

The inventors have shown that the use of GFP as a fusion partner provides several advantages in optimization of expression. This includes (i) increased contact time of the precursor peptides with the modification enzymes in the cytosol, resulting in more effective post-translational modification (PTM); (ii) the potential to evaluate expression using fluorometric readings in vivo, which can substantially reduce optimization time; and (iii) monitoring proteolytic cleavage more accurately by combining the fluorescent properties of the GFP-fusion with SDS-PAGE analysis. The use of *E. coli* as expression host provides additional advantages, such as increased recombinant protein yields, rapid growth on inexpensive media, and availability of extensively characterized expression strains and cloning tools. In addition, although expressing peptides with a fusion partner redirects a portion of the metabolic flux away from peptide synthesis, in the case of production of toxic peptides, fusion increases overall yields by quenching the toxicity to *E. coli*. Further, the use of an RNA thermometer also reduces metabolic load of including an additional lytic gene required to lyse the cell, in that additional recombinant proteins are not required to control temperature dependent expression of the lytic proteins. A further advantage of the method of the present invention is that maintained fluorescence has been shown to provide clear visualization of the target proteins, throughout the expression, extraction, purification, and analysis processes which allows for rapid optimization and troubleshooting. Fluorescent intensity functions as a proxy to guide optimizations because it correlates to the amount of GFP fusion protein.

The method of the present invention is provided in brief below:

Fusion protein vector design: Fusion constructs encoding the fluorescent fusion protein are obtained by fusing the fluorescent fusion partner, for example mCherry or Green fluorescent protein (GFP), to a protein or peptide of interest (PoI) using standard cloning techniques. The peptide of interest can be fused to the N- or C-terminal of the fluorescent fusion partner. A specific protease cleavage site may be included between the fluorescent fusion partner and the peptide of interest. Any protease may be used (e.g. WELQut, Thrombin, TEV, NisP). The fluorescent fusion protein may further include a tag, to facilitate purification, located at the N- and/or C-terminal of the fusion protein. Tags may also be present within the fluorescent fusion protein. Tags that may be used include, but are not limited to, a histidine tag to facilitate purification using Immobilized metal affinity chromatography (IMAC) or a Glutathione S-transferase (GST) tag for use in a pull-down assay. Protease sites can also be included to remove tags. Additionally, the fluorescent fusion protein may include specific secretion sequences to promote secretion of the fusion protein for purification from the extracellular medium. The fusion construct is cloned into a vector. The vector may include a T7 promotor (e.g. pRSF/pACYC/pXH vectors) used in inducible expression using Isopropyl β-d-1-thiogalactopyranoside (IPTG); or may be autoinducible using specific media. The vector may further include additional proteins, such as modification enzymes or may be co-transformed with a compatible vector harbouring additional proteins for post translational modification of target peptides.

Cloning and Expression: The fusion protein vectors are transformed into a heterologous expression host, namely *Escherichia coli* BL21. Expression from the *Escherichia coli* BL21 is achieved through induction with IPTG at a specific bacterial optical density. In addition to IPTG, specific autoinduction media can be used which lowers the cost of producing recombinant proteins and potentially increase yield. Throughout the incubation period expression of the fusion protein can be monitored in vivo using a spectrophotometer or a custom-built detection system capable of measuring fluorescence of the fusion protein partner.

Cell lysis: The *Escherichia coli* BL21 heterologous host is modified to include lytic proteins in its genome or included on an expression vector. The lytic proteins, such as endolysin or bacterial murein hydrolase, are included to simplify and cheapen the lysis process in order to obtain intracellularly expressed fusion proteins. RNA thermometers are used to guide posttranscriptional temperature dependant expression of the lytic protein in *E. coli*. The secondary structures formed by the RNA thermometers interfere with the ribosome binding by blocking the ribosome binding site which in turn prevent translation of the mRNA into protein. Neither are expensive inducers required, as expression of autolysis proteins depend on temperature induced unwinding of RNA transcripts and subsequent translation. Depending on the RNA thermometer used, it can either be strictly on or off, or can act as a dimmer whereby they reduce the translation of a protein at lower temperatures. RNA thermometers can be designed to respond to a range of different temperatures and are customizable to be as responsive as needed. Furthermore, the use of a constitutive promoter (e.g. stationary phase promoters) or inducible promoter (e.g. T7) may be used to control the transcription of the nucleic acid encoding RNA thermometer and lytic gene. The use of stationary phase promoters can result in delayed transcription of the mRNA consisting of the RNA thermometer and lytic gene. This would allow for increased stability of the mRNA and reduce the metabolic load on the cell through delayed expression of the lysis gene. Once target protein expression has occurred, as monitored by detecting the fluorescent fusion partner, cells incubated at modified temperature to induce translation of the lytic protein. Alternatively, cells may be harvested by centrifugation and resuspended in a pro-lysis buffer and incubated at and elevated temperature to induce translation of the lytic protein. After this lytic expression period, cells may be harvested by centrifugation and frozen to further degrade cells walls (<−20° C.). Cells are then thawed and buffer containing detergents or cell permeabilizing chemicals such as 1% SDS or 0.1% Triton X100 are added if necessary. Further, other mechanical stress or detergent may also be used to enhance the cell lysis. The RNA thermometer-guided autolysis results in lysis of cells through contact of the lytic protein with the cells peptidoglycan layer upon cell damage induced by freezing the cells. Cellular debris may be separated from the fusion protein using centrifugation and the fusion protein may be purified thereafter.

Purification: Purification may be achieved using affinity chromatography. The purification method used depends on the tag used. For His-tag fusion proteins, immobilised metal affinity chromatography may be used. Most commonly nickel resin is used, which binds His-tagged proteins. In this purification, the proteins are bound to a nickel resin and eluted by either lowering the pH or using an increasing concentration of imidazole. In an alternative embodiment, a glutathione S-transferase (GST)-tag may be used in the fusion protein, in which case a glutathione resin may be used which has a high affinity for GST. The GST fused protein is removed from the resin using an increasing concentration of reduced glutathione. Alternatively, two different tags may be used in the fusion protein, which can be purified using one method first, followed by another in a dual purification process. Importantly, the fusion protein may be monitored throughout the purification process by making use of the fluorescent properties of the fluorescent fusion partner. In most cases the fusion protein can be directly visualized (e.g. by observing a green fluorescence in the case of GFP). The fusion protein may be manually purified using one of the processes outlined above or any purification known to those of skill in the art, aided by the ability to visualize the fusion protein. Alternatively, the fusion protein may be purified using an automated system. An example of such an automated system, may include, but is not limited to a system that is capable of both detecting proteins at a wavelength of 254 nm as well as detecting the fluorescent fusion partner protein. The system may further include a peristaltic pump capable of variable speed for controlling flow rate, and a detection system capable of measuring proteins (at a wavelength of 254 nm) and the fluorescent fusion partner upon its excitation. Depending on the fluorescent fusion partner used, excitation of the fluorescent fusion partner may be achieved using specific excitation wavelengths and emission filters.

The purified proteins may then be dialysed in order to remove salts and placed in an appropriate buffer. Purification methods such as cation exchange, anion exchange or hydrophobic interaction may also be used to further purify the recombinant protein.

Analysis and visualization: Due to the properties of the fluorescent fusion partner it can easily be detected using SDS PAGE methods described in more detail herein. In one embodiment of this method the fluorescent fusion partner part of the fusion protein may be directly visualized using an LED transilluminator with the appropriate LED wavelengths and filters.

As used herein the terms "protein," "peptide" or "polypeptide" are used interchangeably and refer to any chain of two or more amino acids, including naturally occurring or non-naturally occurring amino acids or amino acid analogues, irrespective of post-translational modification (e.g., glycosylation or phosphorylation). The amino acids are thus in a polymeric form of any length, linked together by peptide bonds.

The term "heterologous peptide of interest" or "peptide of interest" or "protein of interest" as used herein refers to any polypeptide that does not occur naturally in the host cell type. The heterologous polypeptide of interest is intended for expression in a bacterial cell, for example an E. coli cell, using the methods of the present invention. The method of the present invention contemplates the production of viral proteins, bacterial toxins, and mammalian proteins. Non-limiting examples of heterologous polypeptides of interest may include: pharmacological polypeptides (e.g., for medical uses, for cell- and tissue culture) or industrial polypeptides (e.g. enzymes, growth factors) that can be produced according to the methods present invention. The heterologous polypeptides of interest may be useful as vaccines or in vaccines, as well as in other reagents or diagnostics. In particular, the heterologous polypeptide of interest may be a polypeptide from a virus, including viral coat and spike proteins of SARS-COV, HIV proteins. Alternatively, the heterologous polypeptide of interest may be a bacterial toxin protein, including Listeriolysin O; a mammalian protein, such as insulin or autophagic inducing proteins an antibody, such as IgG; a cytokine, such as interleukin 10; a protease, including TEV protease from tobacco etch virus, NisP protease from Lactococcus lactis, serine protease from Staphylococcus aureus; an antimicrobial peptide, such as an anti-tuberculosis and anti-listerial peptides; industrial enzymes such as laccases; molecular enzymes, including ligases, polymerases, restriction enzymes; lytic enzymes used in protein purification, such as endolysins.

As used herein the term "fluorescent fusion partner" refers to a fluorescent peptide fused to the N-terminus of a heterologous polypeptide of interest, the C-terminus of a heterologous polypeptide of interest, or to each of the N-terminus and the C-terminus of a heterologous polypeptide of interest. In some embodiments, a "fluorescent fusion partner" of the invention may include, without limitation, a fusion polypeptide including an amino acid sequence substantially identical to the amino acid sequence of SEQ ID NO: 11 or SEQ ID NO: 13.

As used herein, the term "fusion protein" refers to a polypeptide comprising at least a fluorescent fusion partner and a heterologous polypeptide of interest. The fusion protein of the present invention may further comprise additional amino acid sequences, including a purification tag, a protease cleavage site, or secretion sequence. Another embodiment of the invention includes, without limitation, nucleic acid molecules encoding the aforementioned fusion protein.

The fusion proteins of the invention may comprise a protease cleavage site which permits separation of the fluorescent fusion partner or of the purification tag(s) from the heterologous polypeptide of interest. The protease cleavage site may be a recognition sequence for a site-specific protease. A number of site-specific peptidases are known in the art, including a number of commercial proteases. These include, but are not limited to, WELQut, thrombin, trypsin, nisP, Factor Xa, PreScission protease, enterokinase, V8 protease (Glu-C) and TEV.

In one embodiment of the present invention, the fusion protein may comprise a "purification tag". The purification tag may be a "poly-His tag" or "His-tag", which herein refers to a linear sequence of histidine residues allowing for the purification of a recombinant protein by metal chelate affinity chromatography. Alternatively, a poly-His tag may be used to detect a recombinant polypeptide using an anti-poly-His tag antibody. A poly-His tag may comprise 6, 7, 8, 9 or 10 consecutive Histidine residues. The purification tag may be a "GST-tag". Further, the fusion protein may include more than one tag, for example, but not limited to, a His-tag and a GST-tag for dual purification of the fusion protein.

As used herein the term "host cell which is transformed" refers to a host cell which has either been stably transformed in order to express a heterologous polypeptide, for example a lytic protein, or which has been infiltrated with at least one expression vector which transiently expresses a heterologous polypeptide in the host cell.

As used herein, the term "lytic protein" refers to a protein that causes disruption of the cell membrane and causes a cell to lyse. A number of lytic proteins are known in the art. These include endolysin and bacterial murein hydrolases expressed by, for example, bacteriophages or prophages. Examples include, but are not limited to, lysozyme, GpR having the amino acid sequence of SEQ ID NO: 15, encoded by the nucleotide sequence of SEQ ID NO: 16 and GpE having the amino acid sequence of SEQ ID NO:17, encoded by the nucleotide sequence of SEQ ID NO:18. The lysin proteins are based on the holing-endolysin system, this system is made up of a pore-forming protein and a cell-wall degrading enzyme. The cell wall degrading protein is expressed and is in its active form in the cytoplasm and can only start degrading the cell wall once the pore forming holing creates pores allowing the endolysins to enter the periplasmic space where they can start degrading the cell wall. This system is ideal for the application in the present invention as it allows for expression of the endolysin which would remain inert in the cytoplasm until it can encounter the cell wall.

Expression of the lytic protein may be temperature dependent, for example, the expression of the lytic protein may be regulated by an RNA thermometer. As used herein, the term "RNA thermometer" refers to a temperature-sensitive non-coding RNA molecule which regulates expression of the lytic protein in response to a change in temperature. Depending on the RNA thermometer it can be strictly on or off at selected temperatures, or may act as a dimmer whereby it reduces the translation of a protein at lower temperatures. The RNA thermometers can be designed to respond to a range of different temperatures and are customizable to be as responsive as needed. The use of a constitutive promoter (e.g. stationary phase promoters) or inducible promoter (e.g. T7) may be used to control the transcription of the nucleic acid encoding the RNA thermometer and lytic gene. The use of stationary phase promoters can result in delayed transcription of the mRNA consisting of the RNA thermometer and lytic gene. This would allow for increased stability of the mRNA and reduce the metabolic load on the cell through delayed expression of the lysis gene. Stationary phase promoters are promoters that are more active during later stages of bacterial growth including late exponential and stationary phases.

The terms "nucleic acid", "nucleic acid molecule" and "polynucleotide" are used herein interchangeably and encompass both ribonucleotides (RNA) and deoxyribonucleotides (DNA), including cDNA, genomic DNA, and synthetic DNA. The nucleic acid may be double-stranded or single-stranded. Where the nucleic acid is single-stranded, the nucleic acid may be the sense strand or the antisense strand. A nucleic acid molecule may be any chain of two or more covalently bonded nucleotides, including naturally occurring or non-naturally occurring nucleotides, or nucleotide analogs or derivatives. The term "DNA" refers to a sequence of two or more covalently bonded, naturally occurring or modified deoxyribonucleotides.

The term "isolated", is used herein and means having been removed from its natural environment.

The term "purified", relates to the isolation of a molecule or compound in a form that is substantially free of contamination or contaminants. Contaminants are normally associated with the molecule or compound in a natural environment, purified thus means having an increase in purity as a result of being separated from the other components of an original composition. The term "purified nucleic acid" describes a nucleic acid sequence that has been separated from other compounds including, but not limited to polypeptides, lipids and carbohydrates which it is ordinarily associated with in its natural state.

The term "complementary" refers to two nucleic acids molecules which are capable of forming Watson-Crick base pairs to produce a region of double-strandedness between the two nucleic acid molecules. It will be appreciated by those of skill in the art that each nucleotide in a nucleic acid molecule need not form a matched Watson-Crick base pair with a nucleotide in an opposing complementary strand to form a duplex. One nucleic acid molecule is thus "complementary" to a second nucleic acid molecule if it hybridizes, under conditions of high stringency, with the second nucleic acid molecule. A nucleic acid molecule according to the invention includes both complementary molecules.

As used herein a "substantially identical" sequence is an amino acid or nucleotide sequence that differs from a reference sequence only by one or more conservative substitutions, or by one or more non-conservative substitutions, deletions, or insertions located at positions of the sequence that do not destroy or substantially reduce the antigenicity of one or more of the expressed fusion protein or of the polypeptides encoded by the nucleic acid molecules. Alignment for purposes of determining percent sequence identity can be achieved in various ways that are within the knowledge of those with skill in the art. These include using, for instance, computer software such as ALIGN, Megalign (DNASTAR), CLUSTALW or BLAST software. Those skilled in the art can readily determine appropriate parameters for measuring alignment, including any algorithms needed to achieve maximal alignment over the full length of the sequences being compared. In one embodiment of the invention there is provided for a polypeptide or polynucleotide sequence that has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or 100% sequence identity to the sequences described herein.

Alternatively, or additionally, two nucleic acid sequences may be "substantially identical" if they hybridize under high stringency conditions. The "stringency" of a hybridisation reaction is readily determinable by one of ordinary skill in the art, and generally is an empirical calculation which depends upon probe length, washing temperature, and salt concentration. In general, longer probes required higher temperatures for proper annealing, while shorter probes require lower temperatures. Hybridisation generally depends on the ability of denatured DNA to re-anneal when complementary strands are present in an environment below their melting temperature. A typical example of such "stringent" hybridisation conditions would be hybridisation carried out for 18 hours at 65° C. with gentle shaking, a first wash for 12 min at 65° C. in Wash Buffer A (0.5% SDS; 2×SSC), and a second wash for 10 min at 65° C. in Wash Buffer B (0.1% SDS; 0.5% SSC).

Polypeptides, peptides and peptide analogues can be prepared from their corresponding nucleic acid molecules using recombinant DNA technology.

As used herein, the term "gene" refers to a nucleic acid that encodes a functional product, for instance a RNA, polypeptide or protein. A gene may include regulatory sequences upstream or downstream of the sequence encoding the functional product.

As used herein, the term "coding sequence" refers to a nucleic acid sequence that encodes a specific amino acid sequence. On the other hand, a "regulatory sequence" refers to a nucleotide sequence located either upstream, downstream or within a coding sequence. Generally regulatory sequences influence the transcription, RNA processing or stability, or translation of an associated coding sequence. Regulatory sequences include but are not limited to: effector binding sites, enhancers, introns, polyadenylation recognition sequences, promoters, RNA processing sites, stem-loop structures, translation leader sequences and the like.

In some embodiments, the nucleic acid molecules used in the method of the invention may be operably linked to other sequences. By "operably linked" is meant that the nucleic acid molecules encoding the fusion proteins of the invention and regulatory sequences are connected in such a way as to permit expression of the proteins when the appropriate molecules are bound to the regulatory sequences. Such operably linked sequences may be contained in vectors or expression constructs which can be transformed or transfected into host cells for expression. It will be appreciated that any vector or vectors can be used for the purposes of expressing the fusion proteins of the invention.

The term "promoter" refers to a DNA sequence that is capable of controlling the expression of a nucleic acid coding sequence or functional RNA. A promoter may be based entirely on a native gene or it may be comprised of different elements from different promoters found in nature. Different promoters are capable of directing the expression of a gene in different cell types, or at different stages of development, or in response to different environmental or physiological conditions. A "constitutive promoter" is a promoter that direct the expression of a gene of interest in most host cell types most of the time or at certain growth phases.

The term "recombinant" means that something has been recombined. When used with reference to a nucleic acid construct the term refers to a molecule that comprises nucleic acid sequences that are joined together or produced by means of molecular biological techniques. The term "recombinant" when used in reference to a protein or a polypeptide refers to a protein or polypeptide molecule which is expressed from a recombinant nucleic acid construct created by means of molecular biological techniques. Recombinant nucleic acid constructs may include a nucleotide sequence which is ligated to, or is manipulated to become ligated to, a nucleic acid sequence to which it is not ligated in nature, or to which it is ligated at a different location in nature. Accordingly, a recombinant nucleic acid construct indicates that the nucleic acid molecule has been manipulated using genetic engineering, i.e. by human intervention. Recombinant nucleic acid constructs may be introduced into a host cell by transformation. Such recombinant nucleic acid constructs may include sequences derived from the same host cell species or from different host cell species.

The term "vector" refers to a means by which polynucleotides or gene sequences can be introduced into a cell. There are various types of vectors known in the art including plasmids, viruses, bacteriophages and cosmids. Generally, polynucleotides or gene sequences are introduced into a vector by means of a cassette. The term "cassette" refers to a polynucleotide or gene sequence that is expressed from a vector, for example, the polynucleotide or gene sequences encoding the fusion protein of the invention. A cassette generally comprises a gene sequence inserted into a vector, which in some embodiments, provides regulatory sequences for expressing the fluorescent fusion protein. In other embodiments, the vector provides the regulatory sequences for the expression of the acyl transferase polypeptides. In further embodiments, the vector provides some regulatory sequences, and the nucleotide or gene sequence provides other regulatory sequences. "Regulatory sequences" include but are not limited to promoters, transcription termination sequences, enhancers, splice acceptors, donor sequences, introns, ribosome binding sequences, poly(A) addition sequences, and/or origins of replication.

In some embodiments, the fusion proteins or compositions according to the invention may be provided in a kit, together with instructions for use.

The following examples are offered by way of illustration and not by way of limitation (all buffer compositions listed in table 7).

Example 1

Heterologous Expression of GFP-Fused Class I Lanthipeptides in *E. coli*
Construction of pRSFGFP-NisB Backbone and pACYC-NisC All PCR primers used in this example are provided in Table 1 below. Table 2 provides a description of each of the plasmids used or generated in this example. To construct plasmid pRSFGFP, the mgfp5 gene was amplified by PCR from pTRKH3-ermGFP, a plasmid containing GFP, Ery (Primers=SEQ ID NO:41 and 42) (from Michela Lizier, Addgene plasmid #27169). The PCR product and pRSF Duet-1 were digested with BamHI/PstI and ligated using T4 ligase. This resulted in His-tag fused GFP with a C-terminal WELQ site. The nisB and nisC genes were amplified by PCR using *L. lactis* gDNA as a template (Primers=SEQ ID NOs: 45-48).

The PCR products for nisC and nisB were cloned as Bg/II/XhoI fragments into pACYC Duet-1 and pRSFGFP, respectively. Constructs were transformed into chemically competent *E. coli* BL21 (DE3) and plated onto Luria-Bertani (LB) agar supplemented with kanamycin (50 µg/mL) or chloramphenicol (25 µg/mL) as selective antibiotics for pRSF- and pACYC-constructs, respectively. Single colonies were selected and used to inoculate LB broth supplemented with the respective antibiotics and incubated overnight at 30° C. Plasmid DNA was isolated and used for sequencing reactions (Central analytical facility, CAF, Stellenbosch University), cloning and transformations.
Construction of Lanthipeptide Expressing Strains The nisA gene was amplified by PCR using *L. lactis* genomic DNA as a template. Pep5 and epilancin 15X were amplified using their respective primers (Table 1). The forward primers used to amplify Pep5 and epilancin 15X incorporated a 5' overhang homologous to the 3' region of the nisin leader. The nisin leader was amplified by PCR using *L. lactis* DNA as template with primers 9 (SEQ ID NO:49) and 14 (SEQ ID NO:54) in Table 1 below, with the reverse primer incorporating the nucleotide sequence coding for the thrombin protease site (S-3V).

For fusion PCR, the nisin leader PCR product and the respective Pep5/epilancin 15X PCR products (using primers 10-11 (SEQ ID NOs: 50-51) and 12-13 (SEQ ID NOs: 52-53), respectively were mixed and amplified using primers 9 and 11 (SEQ ID NO:49 and SEQ ID NO:51) for Pep5, or primers 9 and 13 (SEQ ID NO:49 and SEQ ID NO:53) for epilancin 15X. The final fusion PCR results in the fusion of the core-lanthipeptides to the nisin leader. The final fused precursor lanthipeptides (pLanthipeptides) and pRSF Duet-1 were digested with PstI/HindIII and ligated using T4 ligase. The pLanthipeptides in pRSF were digested out with PstI/NotI and ligated into the corresponding sites in pRSFGFP-NisB.

Changing of the protease site in precursor Pep5 (pPep5) and precursor epilancin15X (pEpilancin15X) from a thrombin (AVPR) to a hNisP site (ASPR) was also done with fusion PCR. Template DNA was from the respective pRSFGFP-pLanthipeptides-NisB constructs with the thrombin protease site. The nisin leader was amplified using primers 9 (SEQ ID NO:49) and 16 (SEQ ID NO:56), the reverse primer results in nucleotide substations from GTA (valine) to TCA (serine). The respective core-peptides were amplified using forward primer 15 (SEQ ID NO:55) and their respective reverse primers (SEQ ID NO:51 for Pep5 and SEQ ID NO:53 for epilancin 15X). The PCR products for the leader- and core-peptides were mixed and fusion PCR was performed using the forward primer for the nisin leader (SEQ ID NO:50) and the reverse primers for the respective peptides. Final products were digested and ligated as described above to obtain pRSF-GFPpNisin-NisB (FIGS. 2 and 3).

Substitution of the NisP site to a thrombin site in the pre-nisin construct was achieved using fusion PCR as described above. Primer combinations used included primer 9 (SEQ ID NO:49 and primer 18 (SEQ ID NO:58); primer 17 (SEQ ID NO:57) and primer 4 (SEQ ID NO:44); and primer 9 (SEQ ID NO:49) and primer 4 (SEQ ID NO: 44), using pRSFGFPpNisin-NisB pDNA as template.

The resulting constructs were transformed into chemical competent *E. coli* BL21 (DE3) and plated onto LB agar supplemented with kanamycin (50 µg/mL). Single colonies were selected and used to inoculate LB broth supplemented with kanamycin (50 µg/mL) and incubated at 30° C. overnight. Plasmid DNA was isolated and used for subsequent sequencing reactions (CAF, Stellenbosch) and cloning/transformations. The respective constructs were subsequently co-transformed with pACYCNisC into chemically competent *E. coli* BL21 (DE3) cells and plated onto LB agar supplemented with kanamycin (50 µg/mL) and chloramphenicol (25 µg/mL) and incubated overnight at 30° C. Single colonies were isolated and used in subsequent expression experiments.

Figure 2:
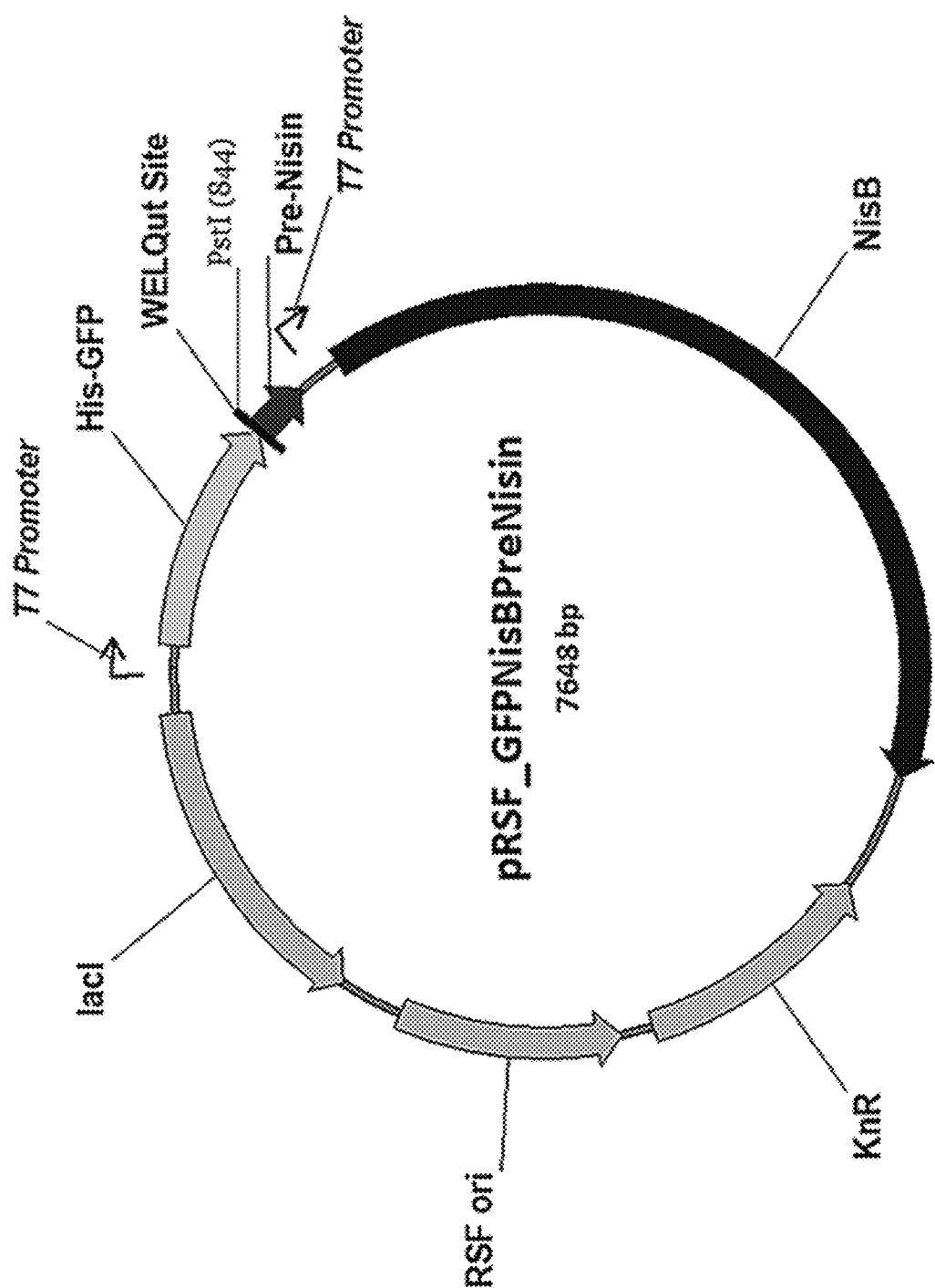
FIG. 2: Plasmid map of pRSF Duet-1 with GFP fused to precursor nisin in MCS-1 and nisB in MCS-2. Relevant restriction sites and WELQut protease site are indicated.
Figure 3:
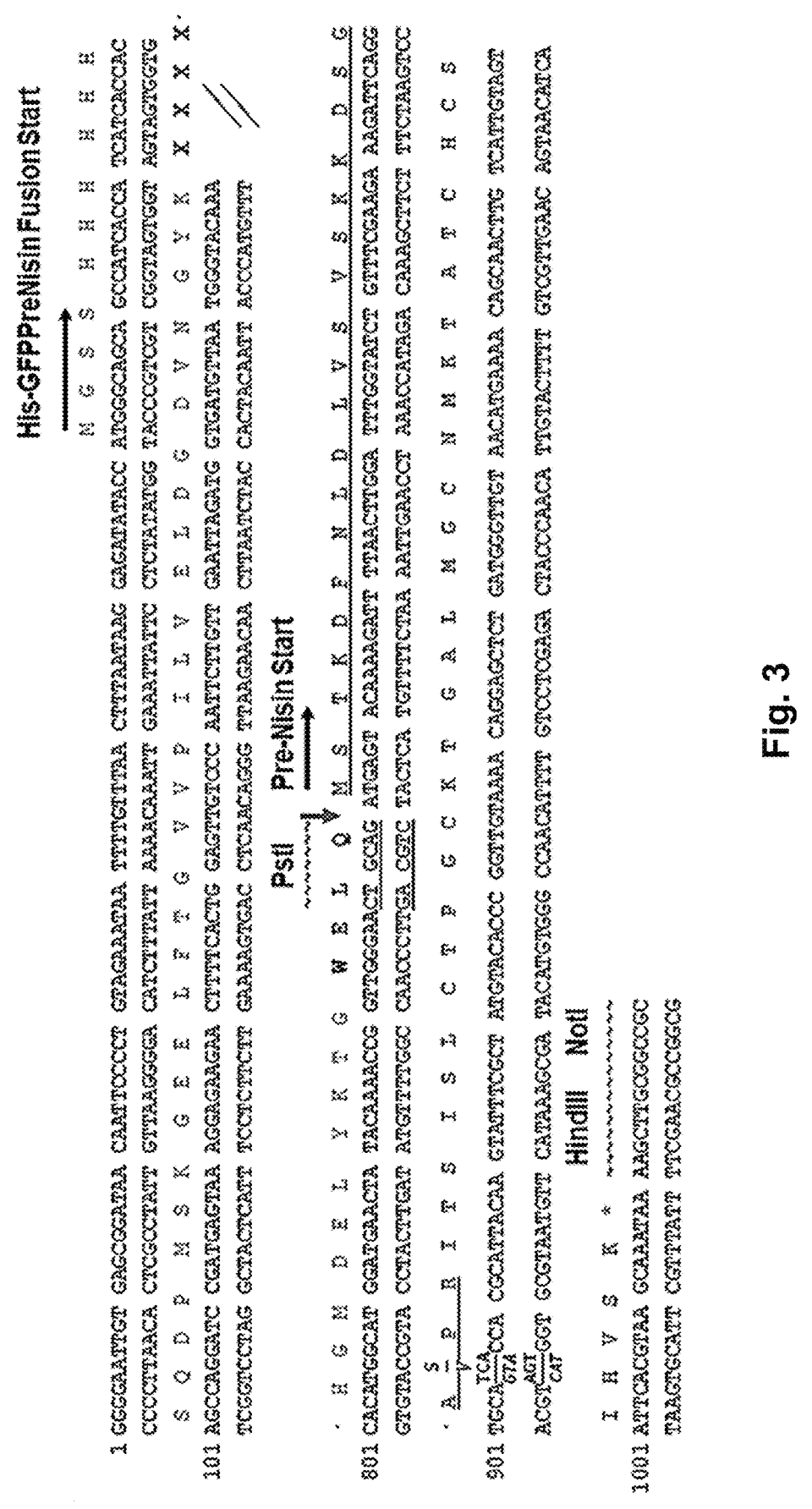

As is detailed above, the inventors of the present invention thus created a backbone plasmid that could be used as a "plug and play" system for a number of precursor peptides (FIGS. 2 and 3).

Construction of non-GFP tagged His-pLanthipeptides was performed. Briefly, the nisA gene was amplified out of *L. lactis* gDNA, nisB and nisC were amplified and cloned as previously described. For generation of His-prePep5 and preEpilancin15X the respective pLanthipeptides were amplified from pRSFGFP-pPep5Th-NisB/pEpilancin15XTh-NisB using forward primer 3 (SEQ ID NO:43) and the respective reverse primers for Pep5 (SEQ ID NO:51) and epilancin 15X (SEQ ID NO: 53). The respective PCR products and pRSF Duet-1 were digested with BamHI/HindIII and ligated using T4 ligase, generating N-terminal His-tagged pre-Lanthipeptides. The His-pLanthipeptides in pRSF were digested out with BamHI/NotI and ligated into the corresponding sites in pRSF-NisB. Transformation and cell culture were performed as described above.

TABLE 1

Primers used in GFP-Fused Class I Lanthipeptides expression in *E. coli*.

| No | Primer | Orientation | Sequence (5'-3') | SEQ ID NO: |
|---|---|---|---|---|
| 1 | GFP_BamHI_F | Forward | GGATCCGATGAGTAAAGGAGAAGAACTTTTCACTGGAGTTGTCCCAATTC | SEQ ID NO: 41 |
| 2 | GFPWELQ_PstI_R | Reverse | CTGCAGTTCCCAACCGGTTTTGTATAGTTCATCCATGCCATGTGTAATCC | SEQ ID NO: 42 |
| 3 | NisA_BamHI_F | Forward | CTAGATGGATCCGATGAGTACAAAAGATTTTAACTTGG | SEQ ID NO: 43 |
| 4 | NisA_HindIII_R | Reverse | CTAGAAGCTTTTATTTGCTTACGTGAATACTACAATG | SEQ ID NO: 44 |
| 5 | NisB_BglII_F | Forward | CAGCCGAGATCTGATGATAAAAAGTTCATTTAAAGCTCAACCG | SEQ ID NO: 45 |
| 6 | NisB_XhoI_R | Reverse | CTAGCTCGAGTCATTTCATGTATTCTTCCGAAACAAACAACC | SEQ ID NO: 46 |
| 7 | NisC_BglII_F | Forward | CTAGGGAAGATCTGATGAATAAAAAAAATATAAAAAGAAATGTTG | SEQ ID NO: 47 |
| 8 | NisC_XhoI_R | Reverse | CTAGCTCGAGTCATTTCCTCTTCCCTCCTTTCAAAAAATCGTC | SEQ ID NO: 48 |
| 9 | GFPNisLeader_PstI_F | Forward | GGAACTGCAGATGAGTACAAAAGA | SEQ ID NO: 49 |
| 10 | NisinLThPep5_F | Forward | CAGGTGCAGTACCACGCACCGCGGGTCCGGCGATCCG | SEQ ID NO: 50 |
| 11 | Pep5HindIII_R | Reverse | CACCAAGCTTTTATTTGCAGCCGTTTTTAC | SEQ ID NO: 51 |
| 12 | NisinLTh15X_F | Forward | CAGGTGCAGTACCACGCAGCGCGAGCATCGTGAAGAC | SEQ ID NO: 52 |
| 13 | 15XHindIII_R | Reverse | GCGCCAAGCTTTTATTTCTTGCCGGTAAAGT | SEQ ID NO: 53 |
| 14 | NisLeaderThr_R | Reverse | GCGTGGTACTGCACCTGAATC | SEQ ID NO: 54 |
| 15 | NisLeaderOri_F | Forward | GAAAGATTCAGGTGCATCACCACGC | SEQ ID NO: 55 |
| 16 | NisLeaderOri_R | Reverse | GCGTGGTGATGCACCTGAATCTTTC | SEQ ID NO: 56 |
| 17 | NisLeaderNis_Thr_F | Forward | TTCAGGTGCAGTACCACGCATTACAAGTAT | SEQ ID NO: 57 |
| 18 | NisLeaderNis_Thr_R | Reverse | ATACTTGTAATGCGTGGTACTGCACCTGAA | SEQ ID NO: 58 |

TABLE 2

Vectors used in GFP-Fused Class I Lanthipeptides expression in *E. coli*.

| Plasmid | Description |
|---|---|
| pRSF Duet-1 | Vector with the IPTG inducible $P_{T7}$, $Km^R$ and cloning site for N-terminal His tag fusion. |
| pACYC | Vector with the IPTG inducible $P_{T7}$, $Cm^R$. |
| pTRKH3-ermGFP | Plasmid containing GFP, $Ery^R$ |
| pRSF-NisB | Used for expression of non-GFP tagged lanthipeptides |
| pACYC-NisC | Used for co-expression of NisC. $Cm^R$ |

TABLE 2-continued

Vectors used in GFP-Fused Class I Lanthipeptides expression in *E. coli*.

| Plasmid | Description |
| --- | --- |
| pRSFGFP | N-terminal His tagged GFP with C-terminal WELQut site. $Km^R$ |
| pRSFGFP-NisB | N-terminal His tagged GFP with C-terminal WELQut site. nisB in multiple cloning site 2. $Km^R$ |
| pRSF-GFPpNisin-NisB | N-terminal His tagged GFP with C-terminal WELQut site fused to precursor nisin (original ASPR, hNisP cleavage site). nisB in multiple cloning site 2. $Km^R$ |
| pRSF-GFPpPep5-NisB | N-terminal His tagged GFP with C-terminal WELQut site fused to nisin leader-Pep5 core peptide (original ASPR, hNisP cleavage site). nisB in multiple cloning site 2. $Km^R$ |
| pRSF-GFPpEpilancin15X-NisB | N-terminal His tagged GFP with C-terminal WELQut site fused to nisin leader-epilancin 15X core peptide, (original ASPR, hNisP cleavage site). nisB in multiple cloning site 2. $Km^R$ |
| pRSF-GFPpNisinTh-NisB | N-terminal His tagged GFP with C-terminal WELQut site fused to precursor nisin, S-3V mutant with AVPR replacing the ASPR hNisP cleavage site. nisB in multiple cloning site 2. $Km^R$ |
| pRSF-GFPpPep5Th-NisB | N-terminal His tagged GFP with C-terminal WELQut site fused to nisin leader-Pep5 core peptide, S-3V mutant with AVPR replacing the ASPR hNisP cleavage site. nisB in multiple cloning site 2. $Km^R$ |
| pRSF-GFPpEpilancin15XTh-NisB | N-terminal His tagged GFP with C-terminal WELQut site fused to nisin leader-epilancin 15X core peptide, S-3V mutant with AVPR replacing the ASPR hNisP cleavage site. nisB in multiple cloning site 2. $Km^R$ |
| pRSF-HispNisin-NisB | N-terminal His tag precursor nisin with ASPR cleavage site. nisB in multiple cloning site 2. $Km^R$ |
| pRSF-HispPep5Th-NisB | N-terminal His tag nisin leader-Pep5 core peptide with AVPR thrombin cleavage site. nisB in multiple cloning site 2. $Km^R$ |
| pRSF-HispEpilancin15XTh-NisB | N-terminal His tag nisin leader-epilancin 15X core peptide with AVPR thrombin cleavage site. nisB in multiple cloning site 2. $Km^R$ |
| pRSF-hNisP | Truncated and C-terminally 8xHis tagged NisP. $Km^R$ |

Optimisation of GFP-pNisin Expression

In all cases overnight cultures of pRSFGFP-pNisin *E. coli* BL21 (DE3) were used to inoculate (1.0% v/v) flasks containing 200 mL of terrific broth supplemented with kanamycin (50 µg/mL) and chloramphenicol (25 µg/mL). The cultures were incubated at 37° C. until an $OD_{600nm}$ of 0.6 was reached, induced and incubated further. For temperature, the cultures were induced with 1 mM IPTG, and further incubated at 4 different temperatures (18° C., 26° C., 30° C. or 37° C.) for 48 hours. IPTG concentration was evaluated at 4 different concentrations (0.1 mM, 0.25 mM, 0.5 mM and 1 mM) and induced cultures were incubated at 26° C. for 24 hours. Incubation after induction (1 mM IPTG) was evaluated at three different times (12 h, 24 h and 48 h) at 26° C. The cells were lysed, purified and tested for activity.

Expression and Purification of Non-GFP Fused His-pLanthipeptides

*E. coli* BL21 (DE3) co-transformed with pRSF-His-pLanthipeptides-NisB and pACYC-NisC were incubated under aeration in LB broth supplemented with kanamycin (50 µg/mL) and chloramphenicol (25 µg/mL) at 30° C. overnight. The overnight culture was used to inoculate (1.0% v/v) 100 mL terrific broth (TB) supplemented with antibiotics. These cultures were incubated under aeration at 37° C. until an $OD_{600}$ of 0.6 was reached. The cultures were induced with 1 mM IPTG and moved to their respective induction temperatures and allowed to express for 18 h. His-pNisin cultures were expressed at 18° C., 26° C. and 37° C. (overnight) and His-pPep5/pEpilancin15X cultures were expressed at 18° C. (overnight). After expression cells were harvested by centrifugation (6164×g, 20 min, 4° C.).

For the soluble fraction the cell pellet was resuspended in 10 mL SB supplemented with lysozyme (1 mg/mL), protease inhibitors, DNAse (1 U/mL) and RNAse (6 U/mL). Cells were incubated on ice for 30 min and subsequently disrupted by sonication on ice (3 times at 70% power output, 50% pulses for 3 min). Lysed samples were centrifuged at 15870×g for 60 minutes, 4° C. The resulting supernatant was used for purification of the soluble fraction and the pellet was resuspended in 10 mL Start Buffer Urea (SBU: 50 mM Tris, 500 mM NaCl, 8M urea, pH 8.0). The resuspended pellet was lysed at room temperature for 30 min followed by sonication and centrifugation at 15870×g for 60 minutes, 4° C. Protein purification was achieved using the AKTA Purifier purification system using prepacked HisTrap HP columns as per manufacturer's instructions. The resulting eluents were desalted against PBS buffer using a prepacked Sephadex G25 column. Desalted samples were used in subsequent activity tests and SDSPAGE gel separations.

Initial Antimicrobial Activity

For initial antimicrobial efficacy testing, both GFP-fused and non-GFP-fused pLanthipeptides were loaded (GFP-pNisin and GFP-pPep5) and cleaved directly in wells with trypsin (5 µg/mL for GFPpNisin) or thrombin (3 U/100 µL for GFP-pPep5). Antimicrobial activity was evaluated against *Lactobacillus* sakei for nisin and against *S. carnosus* for GFP-pPep5. Plates were incubated at 30° C. overnight until visible clear zones were observed. *Lactobacillus* sakei was cultured in MRS broth or agar and *S. carnosus* was cultured in Mueller Hinton Broth or agar.

Figure 4A:
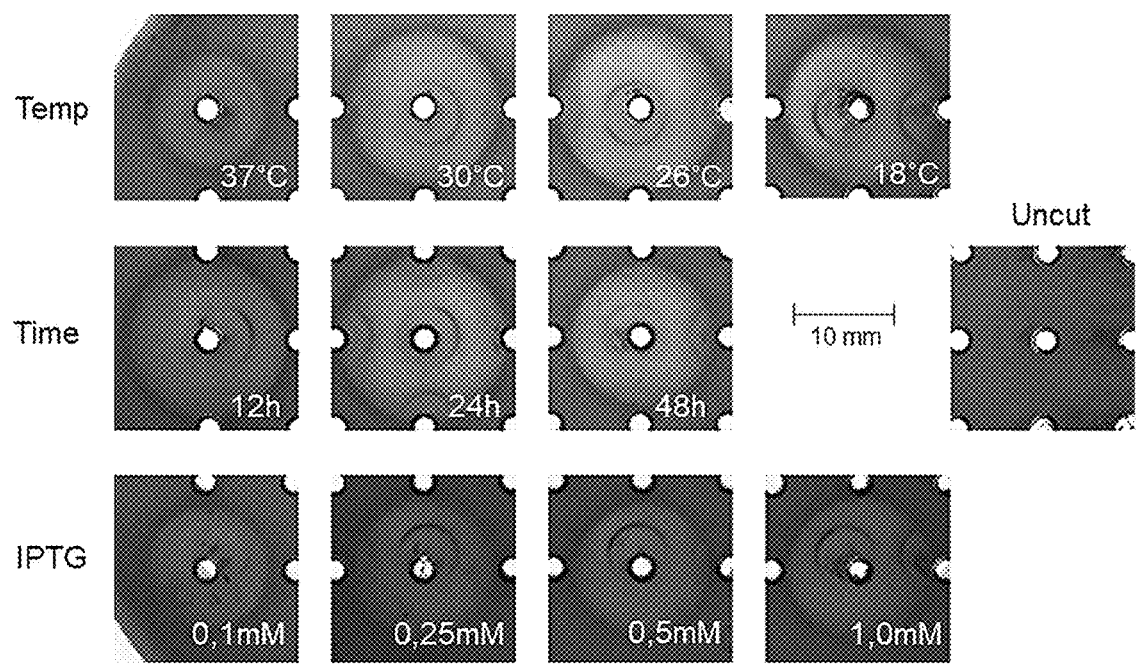
FIGS. 4A and 4B: Optimization and activity results for GFP-pNisin and HispNisin cleaved with trypsin. (4A) Temperature, induction time, and IPTG concentration optimization for GFP-pNisin. (4B) Activity of IMAC-purified and desalted soluble/insoluble E. coli fractions of HispNisin (no fluorescent fusion) expressed at different temperatures. Antimicrobial activity was tested against Lb. sakei.
Figure 4B:
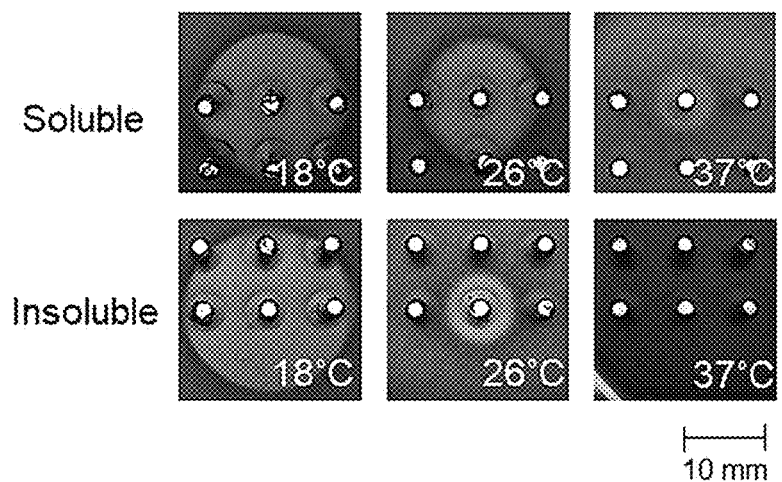

From activity data it was established first that GFP-pNisin was successfully expressed (i.e., modified) in *E. coli* and, second, that expression was robust, as activity was detected when expression was performed at a range of temperatures, induction times and IPTG concentrations. The highest activity (after cleavage with trypsin) was observed for His-tagged precursor nisin (HispNisin) purified from the soluble and insoluble fractions when expression was performed at 18° C. A decrease and substantial loss in activity was observed when expression was performed at 26° C. and 37° C., respectively (FIG. 4). However, electrophoretic separation of soluble and insoluble fractions using SDS-PAGE indicated that higher levels of His-pNisin were obtained at higher temperatures. Due to increased expression rates and possible toxicity, the His-tagged precursor peptide is sequestered to inclusion bodies, which decreases contact time with the respective modification enzymes. In the case of GFP-pNisin the highest activity (after liberation of the core peptide) was observed at 26° C. (FIG. 4)—this may be as a result of increased contact time with the respective modification enzymes in the cytosol, even at higher temperatures, resulting in more effective dehydration and cyclization reactions. Preliminary yield results indicate that using the present invention, ~1.99 mg/L antimicrobially active nisin (after cleavage with nisin protease, NisP, and HPLC purification) could be obtained after 48 h induction. According to ESI-MS, ~0.67-1.08 mg/L of the antimicrobially active product obtained corresponded to fully modified nisin.

Figures 5A, 5B:
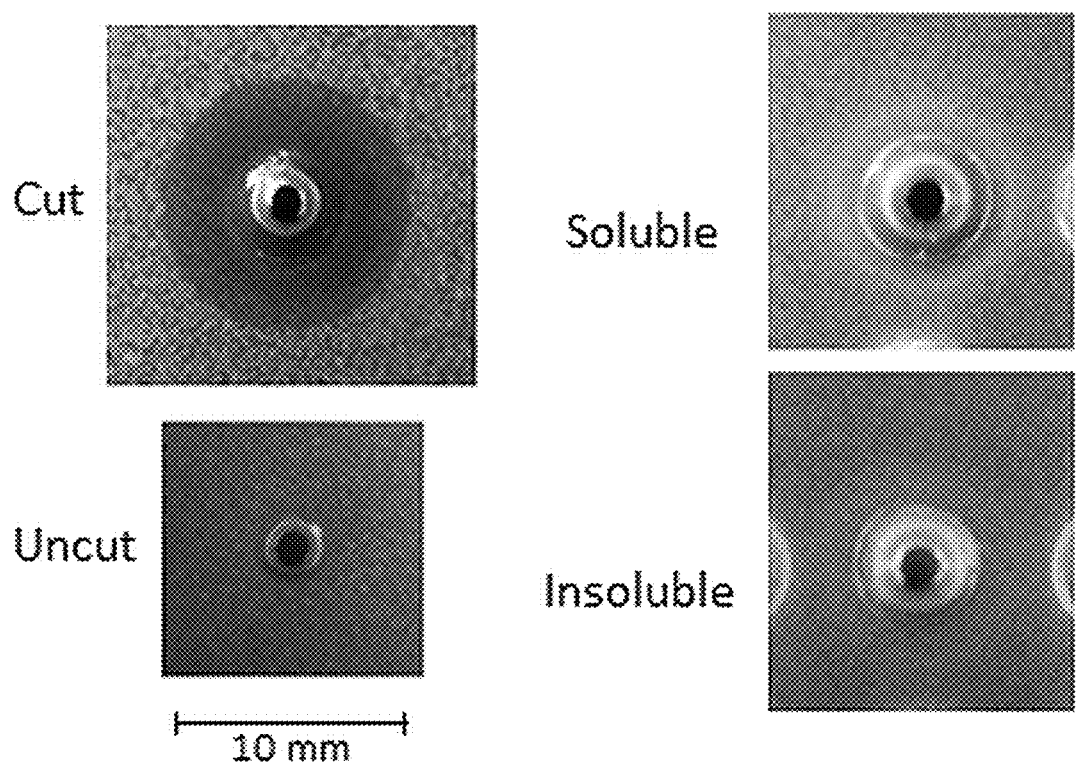
FIGS. 5A and 5B: Antimicrobial activity against S. carnosus of thrombin-cleaved (5A) GFP-pPep5 as well as (5B) IMAC-purified and desalted soluble/insoluble E. coli fractions of His-pPep5.
Figure 6A:
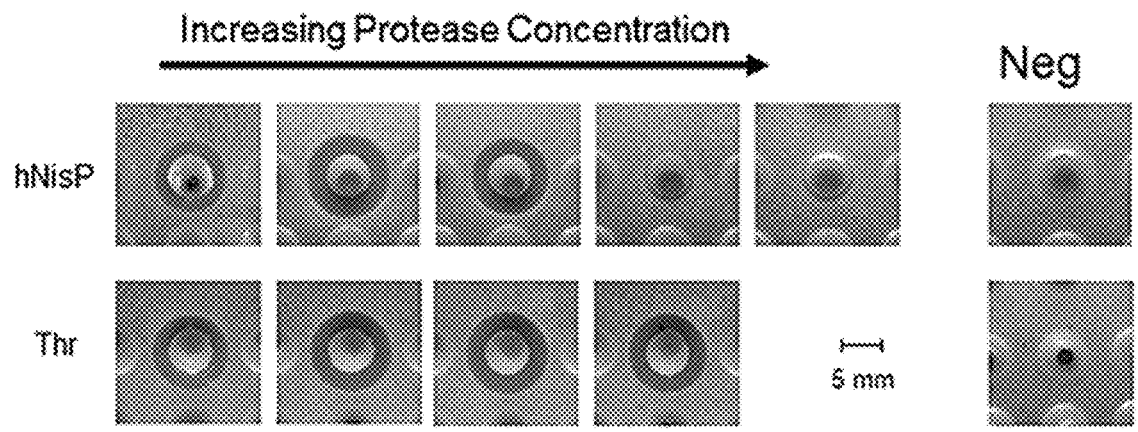
FIGS. 6A-6D: Cleavage optimization of GFP-pLanthipeptides using thrombin and hNisP. GFP-pPep5 after cleavage for (6A) 4 h and (6B) 20 h, and GFPpNisin after cleavage for (6C) 4 h and (6D) 20 h, respectively. GFP-pPep5 activity was tested against *S. carnosus* and GFP-pNisin activity tested against *Lb. sakei*. hNisP was added at concentrations of 0.01, 5, 10, 50 and 70 ng/μL. Thrombin was added at 0.75, 4.5, 3 and 6 U.
Figure 6B:
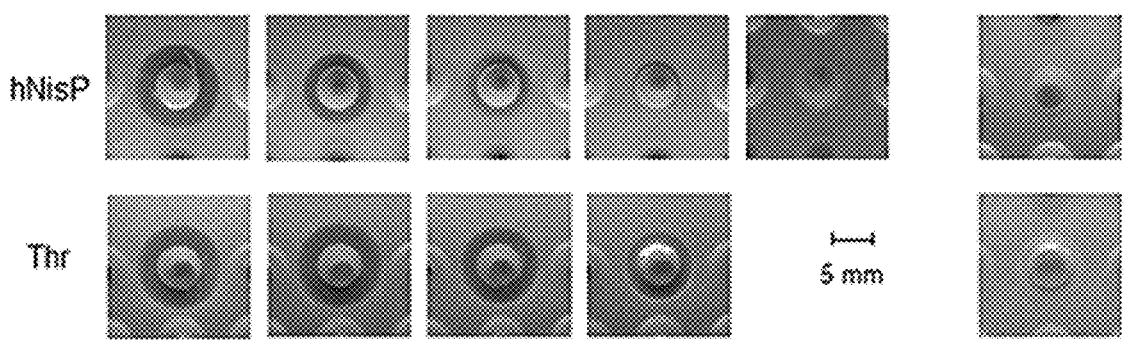
Figure 6C:
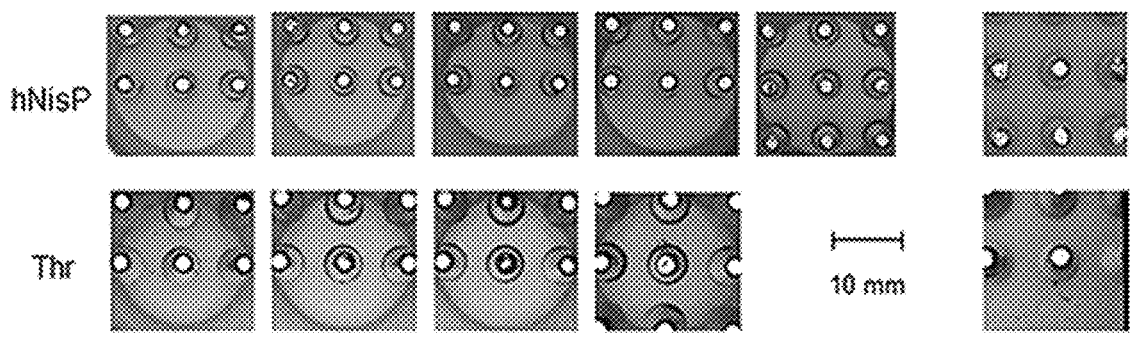
Figure 6D:
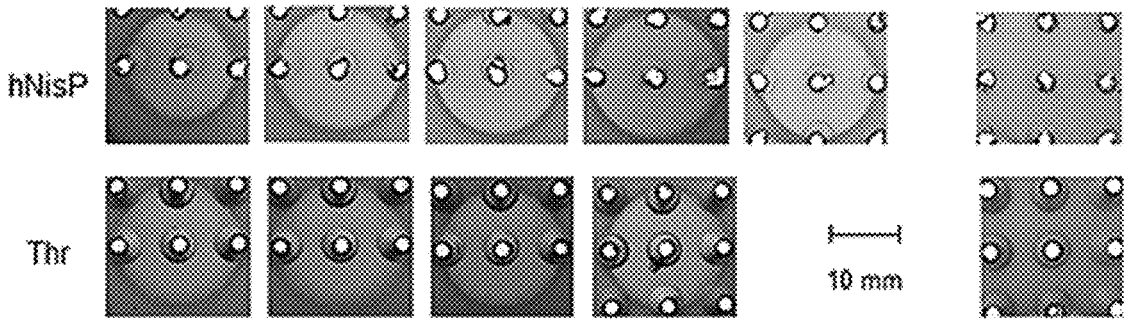
Figure 7A:
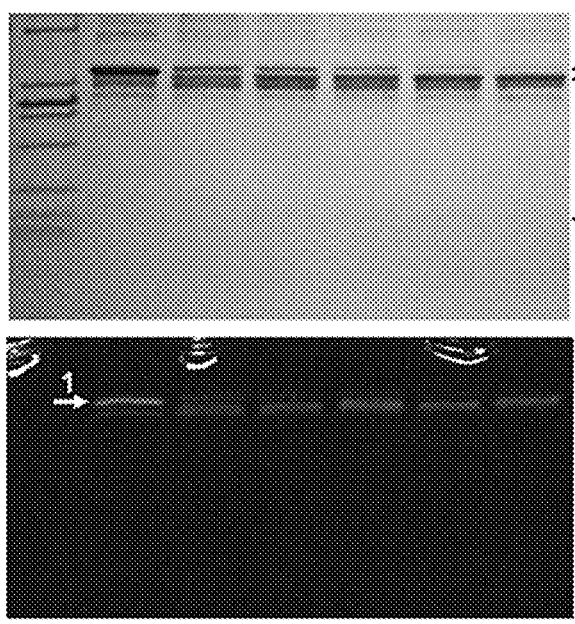
FIGS. 7A-7D: SDS-PAGE stained gels and GFP fluorescent images representing cleavage of GFP-pNisin with thrombin and hNisP. For cleavage of GFP-pNisin with concentration series of (7A) hNisP and (7B) thrombin, top images represent stained gels and bottom images represent GFP fluorescence in SDS-PAGE gels before fixing and staining. For cleavage of GFP-pNisin at optimal concentrations of (7C) hNisP and (7D) thrombin, images on the left represent stained gels and those on the right fluorescence of GFP in SDS-PAGE gels before fixing and staining (top), with activity of uncleaved and cleaved samples loaded onto gels (bottom). Activity was tested against *Lb. sakei*. L=ladder; UC=Uncleaved sample; C=Cleaved sample; 1=Uncleaved GFP-pNisin; 2=Cleaved GFP; and 3=nisin.
Figure 7B:
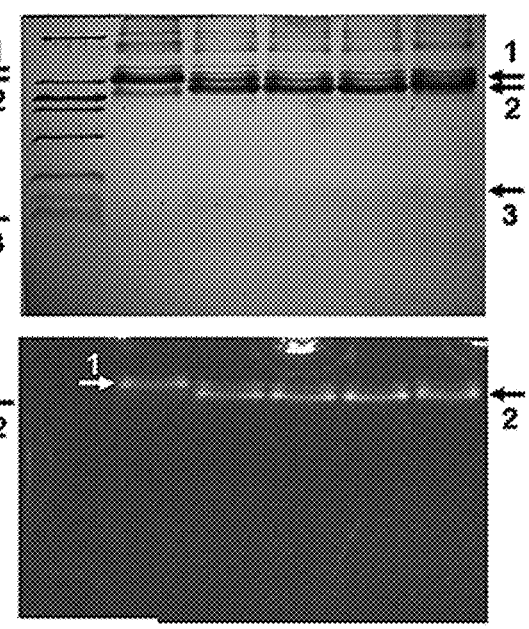
Figure 7C:
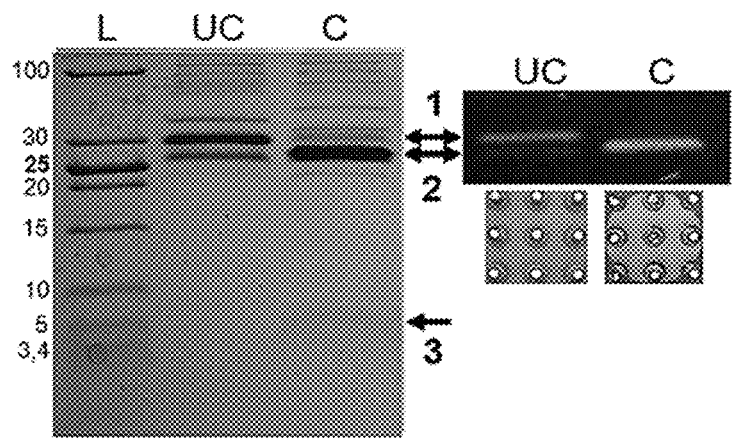
Figure 7D:
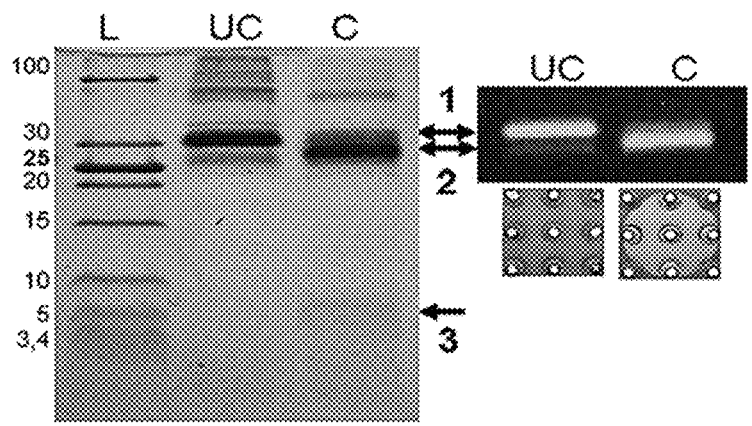

Activity was detected for GFP-pPep5 after cleavage with thrombin with no activity detected in the absence of cleavage (FIG. 5). Fully modified Pep5 could also be detected (using ESI-MS) after cleavage and purification.

Protease Digestion

Protease digestion of the peptides was used to establish whether traceless removal of the core peptides from their respective GFP-leader peptide fusions could be achieved. This is an important aspect to consider when utilizing heterologous expression for the production of lanthipeptides or when using fusion tags. Several commercial proteases are capable of traceless cleavage but are expensive and may not effectively cleave near PTMs. The inventors thus evaluated the capability of NisP to cleave GFP-fused precursor lanthipeptides (GFP-pLanthipeptides).

GFP-pLanthipeptides were cleaved at 37° C. for 4 h and 20 h, with thrombin or hNisP. Heterologously expressed hNisP was added to concentrations of 0.01 ng/μL, 5 ng/μL, 10 ng/μL, 50 ng/μL and 70 ng/μL. Thrombin was added at 0.75 U, 4.5 U, 3 U and 6 U. Cleavage reactions were performed in 100 μL reactions and protein concentrations of GFP-pLanthipeptides were adjusted to final concentrations of 1 mg/ml with the exception of GFP-pPep5Th which was adjusted to 0.9 mg/mL. Cleavage reactions were stopped by the addition of protease inhibitors. Antimicrobial activity was evaluated against Lb. sakei and S. carnosus for GFP-pNisin (30 μL) and GFP-pPep5 (80 μL), respectively. Plates were incubated at 30° C. overnight until visible clear zones were observed. Samples were separated using SDS-PAGE.

Cleavage with both thrombin and hNisP resulted in the liberation of active lanthipeptides after 4 and 20 h of cleavage (FIG. 6). Interestingly, increasing the concentration and cleavage time with both thrombin and hNisP had a detrimental effect on the antimicrobial activity of Pep5, most likely due to nonspecific hNisP cleavage sites within the core peptide that are not protected by lanthionine/methyl-lanthionine bridges.

SDS-PAGE

In order to visualize GFP fluorescence after electrophoretic separation, samples were not boiled in sample buffer but incubated at 37° C. for 30 min. Subsequently 7 μL sample was loaded into wells of a 20% tricine SDS-PAGE gel. To reduce heat generation and aid in separation of smaller peptides SDS-PAGE gels were run at 8° C. For visualization of GFP fluorescence in SDS-PAGE gels, direct photographic images were taken of samples exposed to UV light (312 nm) using a digital camera or the MiniBIS Pro DNR Bio-imaging system (DNR Bio-imaging systems, Israel). After UV imaging, gels were washed with dH2O and fixed in 5% (v/v) glutaraldehyde for 1 h. After fixing gels were washed in dH2O and stained using Blue silver Coomassie stain until protein bands could be visualized.

Traditionally, cleavage efficiency would be evaluated using SDS-PAGE. However, conventional staining methods do not always provide a clear picture of cleavage efficiency. The inventors of the present inventions present alternative assessment methods made possible using GFPfusion. By taking advantage of the fluorescent properties of GFP-pNisin, cleavage efficiency could be visualized more clearly by using both UV imaging and conventional Coomassie staining by tracking the migration of cleaved and uncleaved GFP-pNisin (FIG. 7). Using this combined method, the inventors were able to distinguish clearly uncleaved and cleaved GFP-pNisin from background proteins by overlaying UV and stained images. In the uncleaved sample two fluorescent bands were detected, but this does not indicate partially cleaved GFPpNisin as antimicrobial activity was absent in the uncleaved sample (FIG. 7 C and D). Satisfactory cleavage was observed for GFP-pNisin at thrombin and hNisP concentrations tested (FIG. 7 A and B).

Using the methods described in Example 1 above, the inventors expressed antimicrobially active post translationally modified lanthipeptides. The inventors also illustrated the potential of expressing additional modification enzymes along with the fluorescently fused PoI with the fluorescent fusion not interfering with modification enzyme activity. Furthermore, the inventors illustrate the successful use of a protease to liberate the active lanthipeptides from their fluorescent fusion partners using at least two different proteases.

Example 2

Heterologous Expression of GFP-Fused Subclass 11a Bacteriocins in E. coli

Construction of the Plantaricin 423 and Mundticin ST4SA GFP-Bacteriocin Expression Vectors All PCR primers used in this example are provided in Table 3 below. Table 4 provides a description of each of the plasmids used or generated in this example. The same pRSFGFP backbone plasmid described in example 1 was used here.

Genomic DNA from L. plantarum 423 and E. mundtii ST4SA was used as a template to amplify mature plantaricin 423 and mundticin ST4SA bacteriocin genes using the GFP-PlaX_Pst_Fwd/GFP-PlaX_Hind_Rev (SEQ ID NO:59 and SEQ ID NO: 60) and GFP-MunX_Pst_Fwd/GFP-MunX_Hind_Rev (SEQ ID NO:61 and SEQ ID NO: 62) primer sets, respectively. These primer sets added 5' PstI and 3' HindIII restriction sites for cloning mature plantaricin 423 (plaA) or mundticin ST4SA (munST4SA) genes as GFP fusions in pRSFDuet-1. The amplified bacteriocin genes were purified using the GeneJet PCR purification kit (Thermo Scientific) and digested with PstI and HindIII. The digestion mixtures were purified again using the GeneJet PCR purification kit according to the manufacturer's instructions and used in subsequent cloning experiments.

Figure 8:
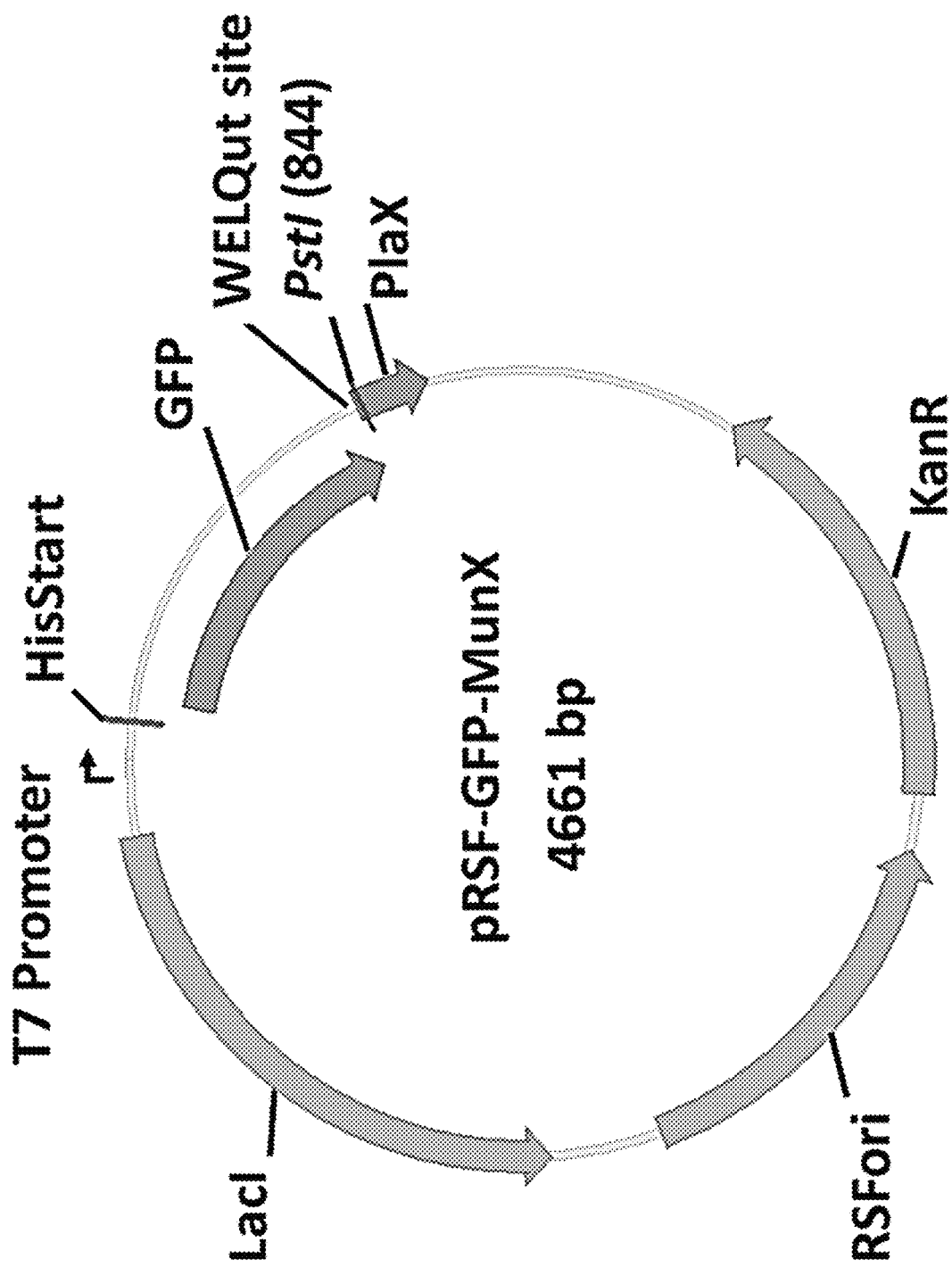
FIG. 8: Plasmid map of pRSF-GFP-MunX for the T7 controlled heterologous expression of GFP-MunX. Liberation of mundticin ST4SA using the WELQut protease.
Figure 9:
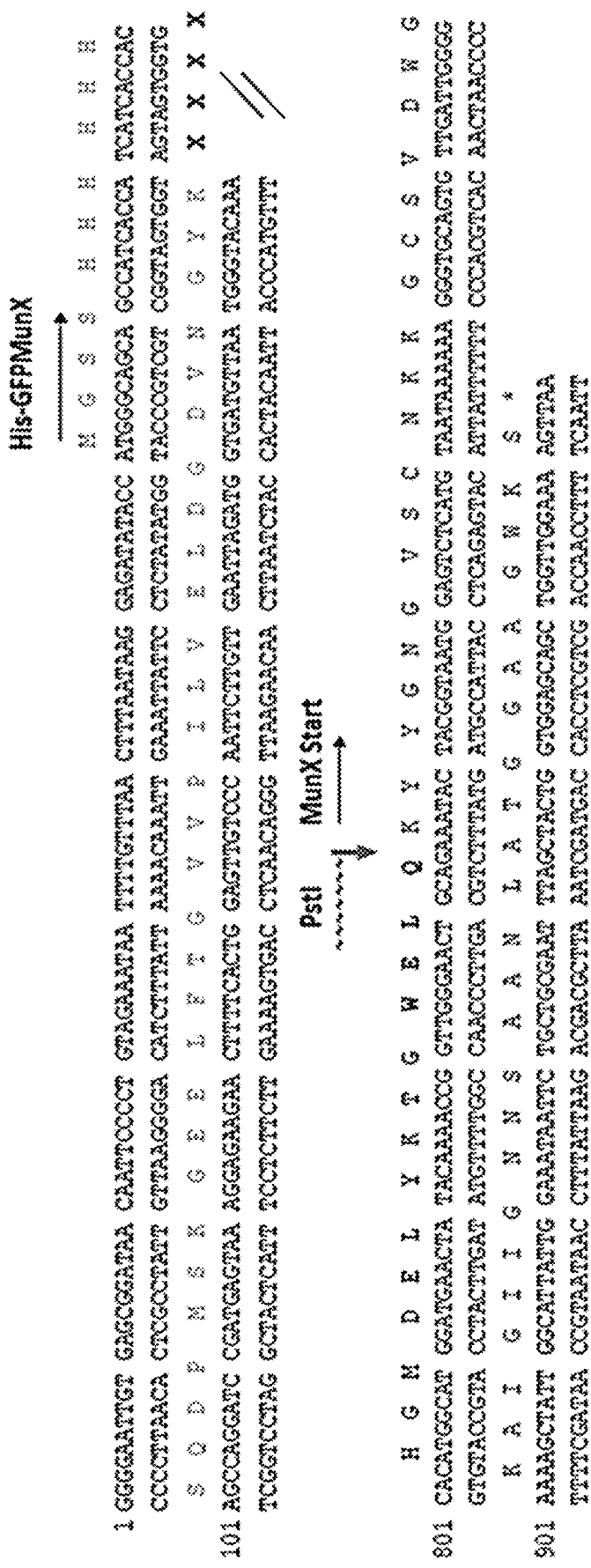
FIG. 9: The amino acid sequence for GFP-MunX (SEQ ID NO:32) with the WELQut protease cleavage sequence indicated (grey arrow). The corresponding nucleotide sequence is also shown (SEQ ID NO:33).
Figure 10:
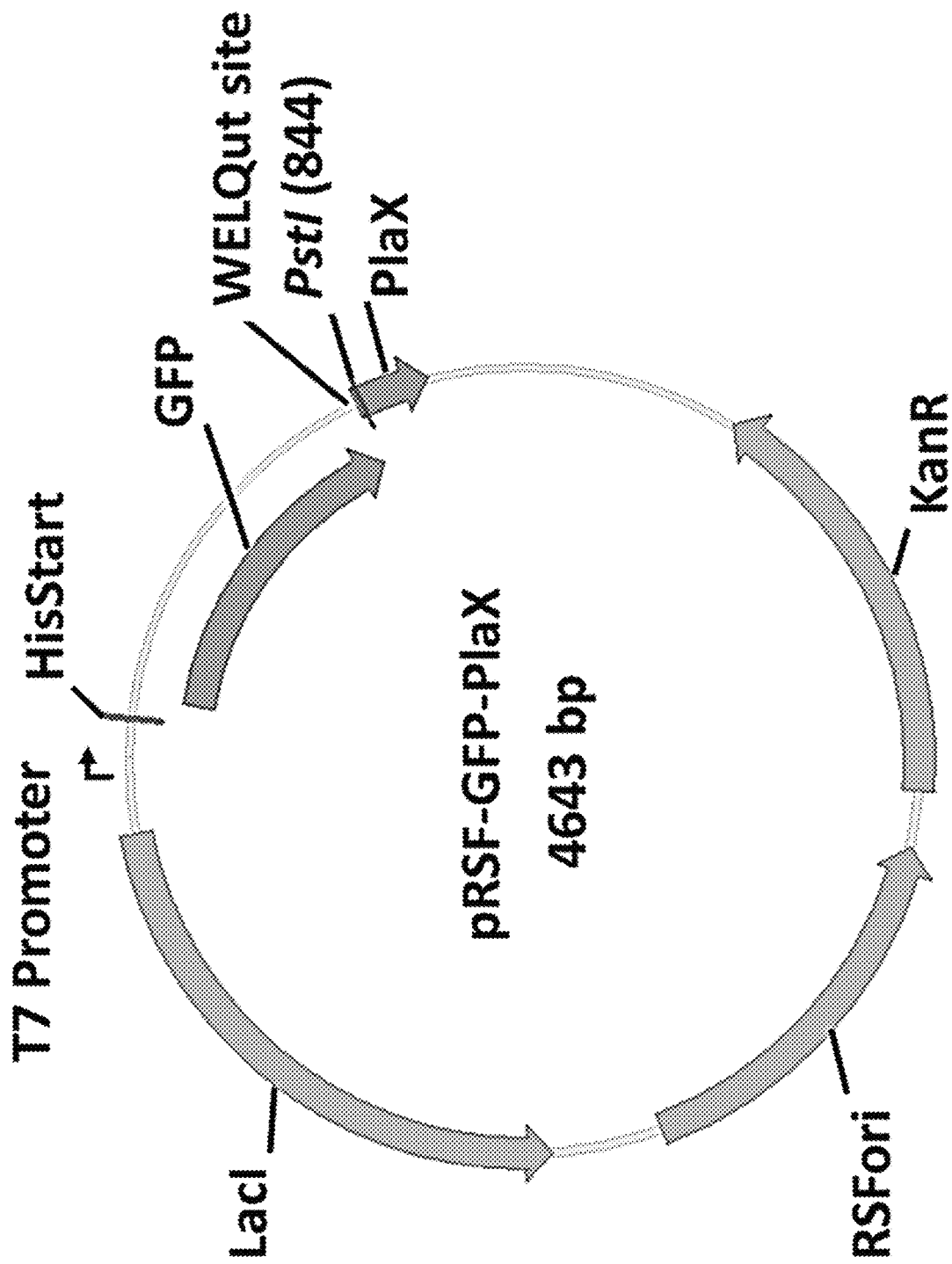
FIG. 10: Plasmid map of pRSF-GFP-PlaX for the T7 controlled heterologous expression of GFP-PlaX. Liberation of plantaricin 423 using the WELQut protease.
Figure 11:
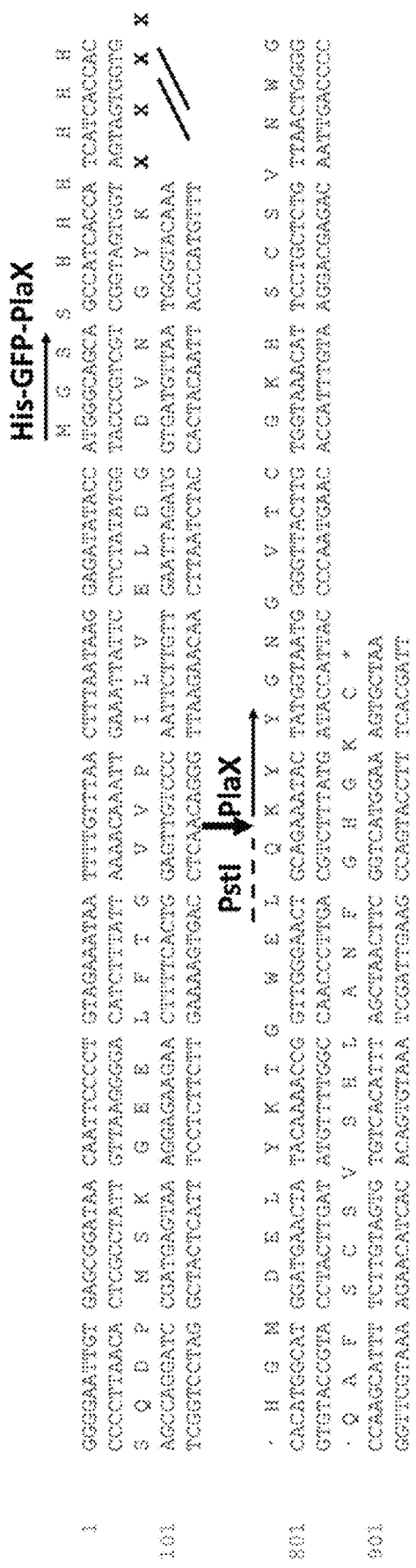
FIG. 11: The amino acid sequence for GFP-PlaX (SEQ ID NO:34) with the WELQut protease cleavage sequence indicated (grey arrow). The corresponding nucleotide sequence is also shown (SEQ ID NO:35).

The pJET-GFP plasmid was digested with BamHI/PstI; the pRSFDuet-1 vector was digested with BamHI/HindIII. The linear pRSFDuet-1 vector and digested GFP fragment were purified using agarose gel electrophoresis, gel-excised and recovered. In one single ligation reaction, the BamHI/PstI GFP fragment and PstI/HindIII bacteriocin fragment was ligated into the linear pRSFDuet-1 vector (BamHI/HindIII). The fragments were ligated using a Vector:Insert_GFP:Insert_Bacteriocin molar end ratio of 1:3:3. The resulting constructs, pRSF-GFP-PlaX (FIGS. 10 and 11), and pRSF-GFP-MunX (FIGS. 8 and 9), were used to transform chemically competent E. coli BL21 (DE3) cells. The pRSF-GFP-PlaX and pRSF-GFP-MunX plasmids were extracted from phenotypically green fluorescent, kanamycin (50 μg/mL) resistant colonies of E. coli BL21 (DE3). The mature plantaricin 423 and mundticin ST4SA genes were sequenced in pRSF-GFP-PlaX and pRSF-GFP-MunX plasmids using the MCS1_Rev primer (SEQ ID NO:63) and confirmed to be correct.

cell pellet was resuspended in 15 mL/g wet weight SB buffer supplemented with 1 mg/mL lysozyme and incubated with agitation at 8° C. for 45 min. After incubation, the lysed cells were subjected to sonication (50% amplitude, 2 s pulse, 2 s pause, 6 min) using the Omni Ruptor 400 (Ultrasonic Homogenizer, Omni International). RNaseI and DNaseI were added to a final concentration of 10 and 5 mg/mL, respectively, and the lysate incubated at room temperature for 15 min. The cell lysate was then centrifuged for 90 min at 20 000 g at 4° C.; the cell-free supernatant was collected. Imidazole was added to the cell-free supernatant to a final concentration of 10 mM.

The His-tagged GFP-bacteriocin fusion proteins, GFP-PlaX and GFP-MunX, were purified with IMAC using the Ni-NTA superflow resin, according to the Qiagen expressionist handbook's instructions for batch purification. The ÄKTA purifier system was used in conjunction with Sephadex G25 resin packed into column (16×65 mm, GE Healthcare) for exchanging the sample from SB500 to WELQut cut

TABLE 3

Primers used in GFP-Fused Subclass IIa Bacteriocins expression in E. coli.

| No | Primer | Orientation | Sequence (5'-3') | SEQ ID NO: |
|---|---|---|---|---|
| 1 | GFP-PlaX_Pst_Fwd | Forward | TAAGGGATCCGTGGGAACTGCAG AAATACTATG | SEQ ID NO: 59 |
| 2 | GFP-PlaX_Hind_Rev | Reverse | TATTAAGCTTAGCACTTTCCATGAC CGAAGTTAGCTAAATG | SEQ ID NO: 60 |
| 3 | GFP-MunX_Pst_Fwd | Forward | ATCGCTGCAGAAATACTACGGTAA TGGAGTCTCATGTAATAAAAAAG | SEQ ID NO: 61 |
| 4 | GFP-MunX_Hind_Rev | Reverse | ACGCAAGCTTAACTTTTCCAACCA GCTGC | SEQ ID NO: 62 |
| 5 | pRSFMCS1_R | Reverse | GATTATGCGGCCGTGTACAA | SEQ ID NO: 63 |

TABLE 4

Vectors used in GFP-Fused Subclass IIa Bacteriocins expression in E. coli.

| Plasmid | Description |
|---|---|
| pRSF Duet-1 | Vector with the IPTG inducible $P_{T7}$, $Km^R$ and cloning site for N-terminal His tag fusion. |
| pTRKH3-ermGFP | Plasmid containing GFP, $Ery^R$ |
| pJET-GFP | GFP-cloning vector |
| pRSF-GFP-PlaX | Heterologous expression of GFP-PlaX |
| pRSF-GFP-MunX | Heterologous expression of GFP-MunX |

Overexpression of GFP-Bacteriocin Fusion Proteins in E. coli BL21 (DE3)

Starter cultures of 30 mL LB broth containing 50 mg/mL kanamycin were inoculated with respective E. coli BL21 (DE3) transformants containing pRSF-GFP-PlaX or pRSF-GFP-MunX constructs. The starter cultures were incubated at 37° C. for 12 h with constant agitation. Starter cultures were used as an inoculum for the expression of GFP-PlaX and GFP-MunX, respectively, (1% v/v). At an $OD_{600nm}$ of 0.6-0.65, expression of the respective GFP fusion proteins was induced using 0.1 mM IPTG.

The newly generated GFP-fusion proteins, GFP-PlaX and GFP-MunX were successfully expressed in E. coli while retaining the autofluorescent properties of GFP.

Ni-NTA Purification of GFP-MunX and GFP-PlaX Proteins

Induced cells were harvested by centrifugation at 8000 g for 20 min at 4° C. The supernatant was discarded, and the buffer. Following successful purification of the proteins, the fluorescent properties of GFP was used to evaluate the optimal expression conditions for increased yield production in terms of fluorescent output. This included different temperatures, expression times and IPTG concentrations, respectively.

Incubation Temperature Optimization for GFP-MunX Expression

Only the GFP-MunX fermentation was temperature optimized as cleaved GFP-MunX had a higher specific activity. The GFPMunX expression temperature optimization was performed at 18, 26, and 37° C. with three biological repeats of E. coli BL21 (DE3) harbouring the pRSF-GFP-MunX plasmid. The three biological repeats of E. coli pRSF-GFP-MunX were used to inoculate three 400 mL flasks of terrific broth containing 50 mg/mL kanamycin. The cultures were grown at 37° C. until induction using 0.1 mM IPTG at an $OD_{600nm}$ of 0.6-0.65. Each 400 mL culture was split into three 100 mL cultures that were incubated at 18, 26, and 37° C. for 48 h, respectively.

To measure in vivo GFP-MunX expression, 1 mL samples from each flask were collected in triplicate at the time of induction; samples were collected again at 24 and 48 h and frozen at −80° C. After collection, samples were thawed, centrifuged and washed twice with potassium phosphate buffer (pH 7.4). The in vivo expression of GFP-MunX was fluorometrically measured in relative fluorescent units (RFUs) at 488 nm (excitation) and 509 nm (emission) using a Tecan Spark M10™ (Tecan Group Ltd., Austria).

After 48 h, the total GFP-MunX RFU production for each sample was calculated by harvesting the induced cells from 80 mL of culture (centrifugation 8000×g for 20 min at 4° C.). The mass of each cell pellet was then measured before resuspension in 15 mL/g wet weight SB buffer. The GFP-MunX in each sample was extracted and purified using IMAC as described previously. Briefly, 5 mL from each cell-free lysate was purified using 5 ml Ni-NTA Superflow cartridges. The RFUs of each Ni-NTA purified GFP-MunX sample was measured using the Tecan M10™ Spark (Tecan Group Ltd., Austria). The RFUs/g were then calculated for each sample by dividing the measured RFUs by the equivalent wet weight (g) of cells lysed for purification (i.e., grams of lysed cells in 5 mL). The total RFUs produced for each sample was calculated by multiplying the RFUs/g by the total wet weight of cells harvested in each sample.

Figure 12A:
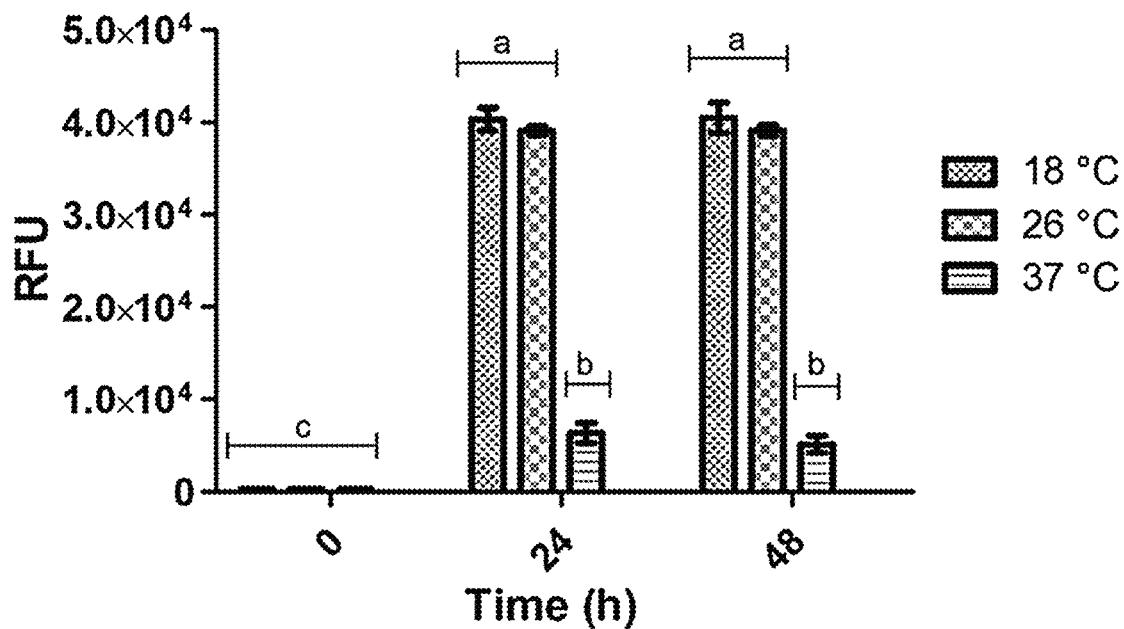
FIGS. 12A and 12B: Fluorometric intensity of *E. coli* pRSF-GFP-MunEx expressing GFP-MunEx at 18, 26, and 37° C. (12A) In vivo fluorometric measurements after 0, 24, and 48 h. (12B) The total relative amounts of GFP-MunEx calculated after protein extraction and Ni-NTA purification of the 48 h expression. Fluorometric intensity measured in Relative fluorescent units (RFU). Dissimilar letters on bars indicates means which are significantly different from one another according to Bonferroni post-test ($P<0.05$).

Significantly higher fluorescent intensity was measured in vivo at 18 and 26° C. compared to 37° C. after 24 and 48 h of expression, respectively (FIG. 12). However, these in vivo measurements do not consider total wet cell weight and do not accurately represent total target protein expression at each temperature. For measurement of total target protein expression in terms of relative fluorescence units (RFUs), the following formula (1) was used:

$$\text{Total } RFU = \frac{RFUs \text{ of Ni–NTA purified eluent}}{\text{wet cell weight used for purification}} \times \text{total cell weight} \quad (1)$$

Figure 12B:
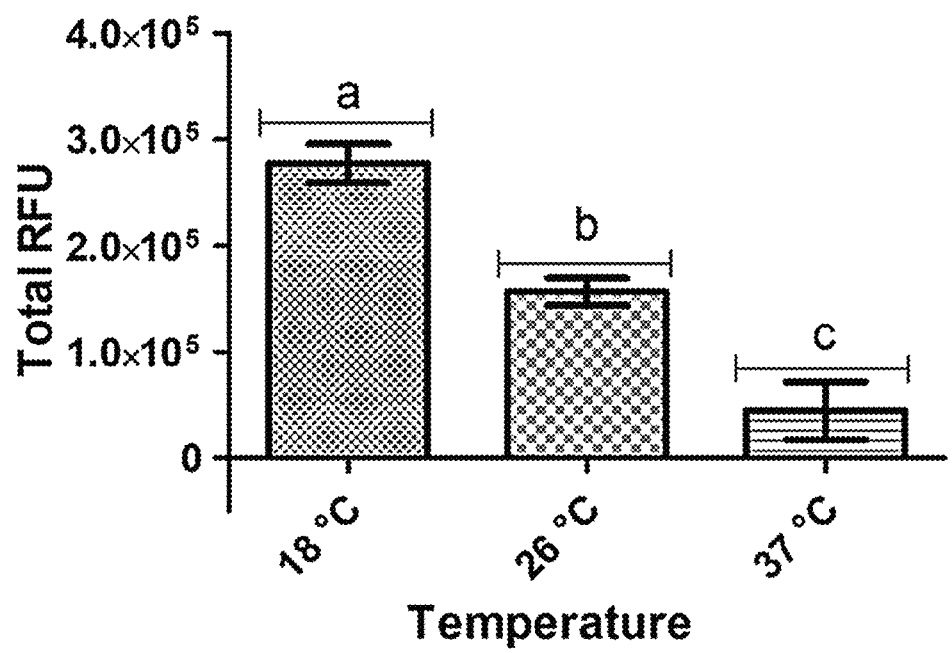

Total RFU production for GFP-MunX is represented in FIG. 12B, where significantly higher RFUs were produced at 18° C. This fluorescent intensity was correlated to the presence of antimicrobial activity after cleavage using SDS-PAGE analysis.

Optimization of IPTG Concentration for Induction

Fluorometric intensity was used to optimize IPTG induction concentration for GFP-MunX expression using the Tecan Spark M10TM's (Tecan Group Ltd., Austria) kinetic incubation program and humidity cassette in a 96 well microtiter plate. Three biological repeats of *E. coli* BL21 (DE3) harbouring the pRSF-GFPMunX plasmid were inoculated into three 1 L Erlenmeyer flasks containing 200 mL filter sterilized terrific broth supplemented with 50 mg/ml kanamycin, and incubated at 37° C. Once an $OD_{600nm}$ of 0.55 was reached, each culture was chilled in an ice bath. Culture aliquots were then incubated with 0.01, 0.05, 0.1, 0.2, 0.4, 0.6, 0.8, 1, and 2 mM IPTG (final concentration) in triplicate in a 96 well microtiter plate. The microtiter plate was incubated within a humidity chamber by the Tecan Spark M10™ at 26° C. for 20 h. Every 20 min the microtiter plate was shaken for 30 s, allowed to settle for 10 s, RFUs were then measured at 509 nm (emission) after excitation at 488 nm.

Figure 13A:
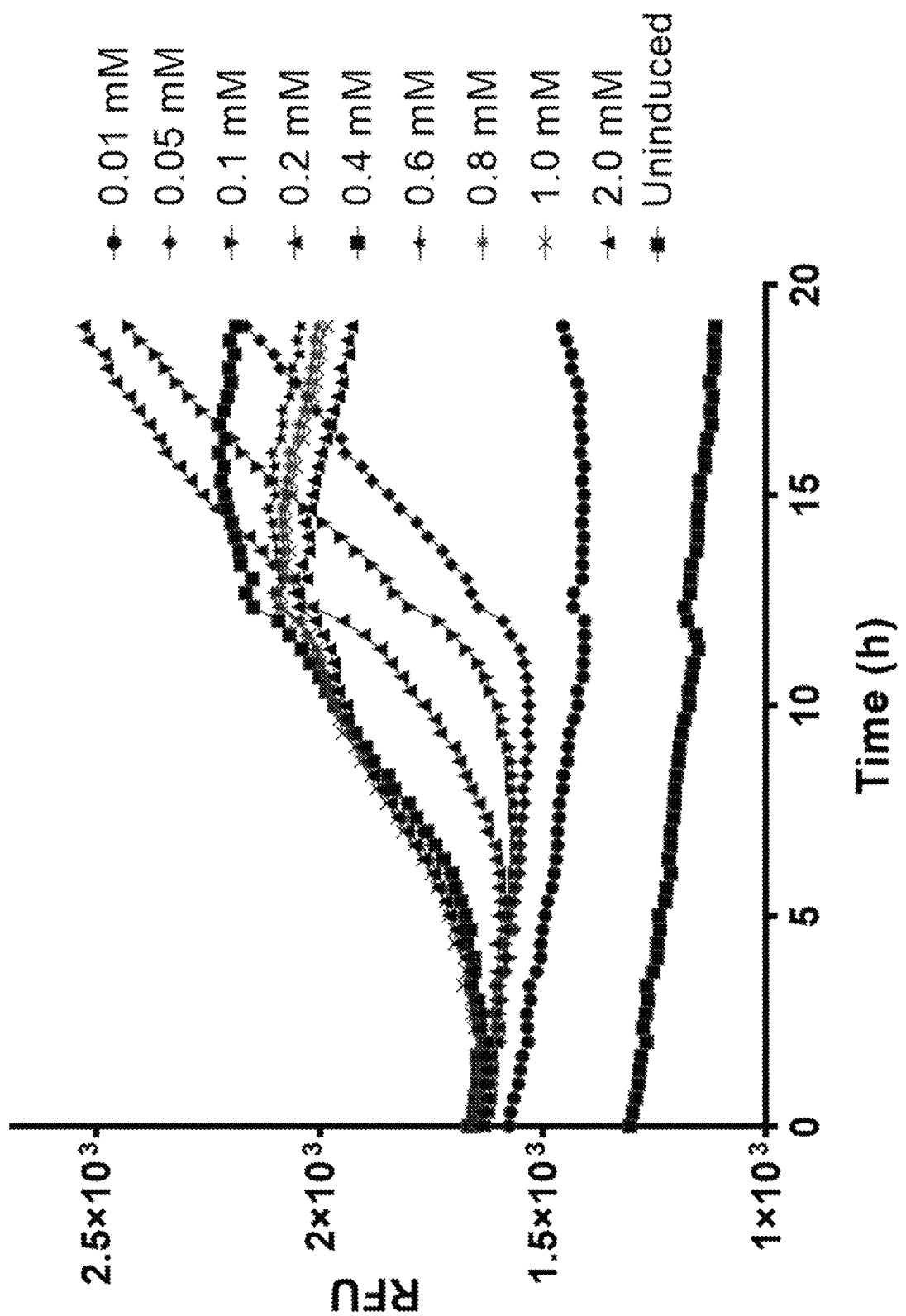
FIGS. 13A and 13B: Optimization of IPTG concentration for GFP-MunX expression at 26° C. over time, fluorescent intensity was measured in relative fluorescent units (RFUs). (13A) In vivo RFU measurements captured every 25 min, were n=3 (biological triplicates measured in technical triplicate), each point represents the mean with SEM indicated by error bars. (13B) Mean RFU output comparison for GFP-MunX expression after 19 h incubation over the indicated range of IPTG concentrations. Arrows indicate Tukey's multiple comparison test results identifying that 0.1 and 0.2 mM produce significantly higher RFU outputs from all other tests ($P<0.05$).
Figure 13B:
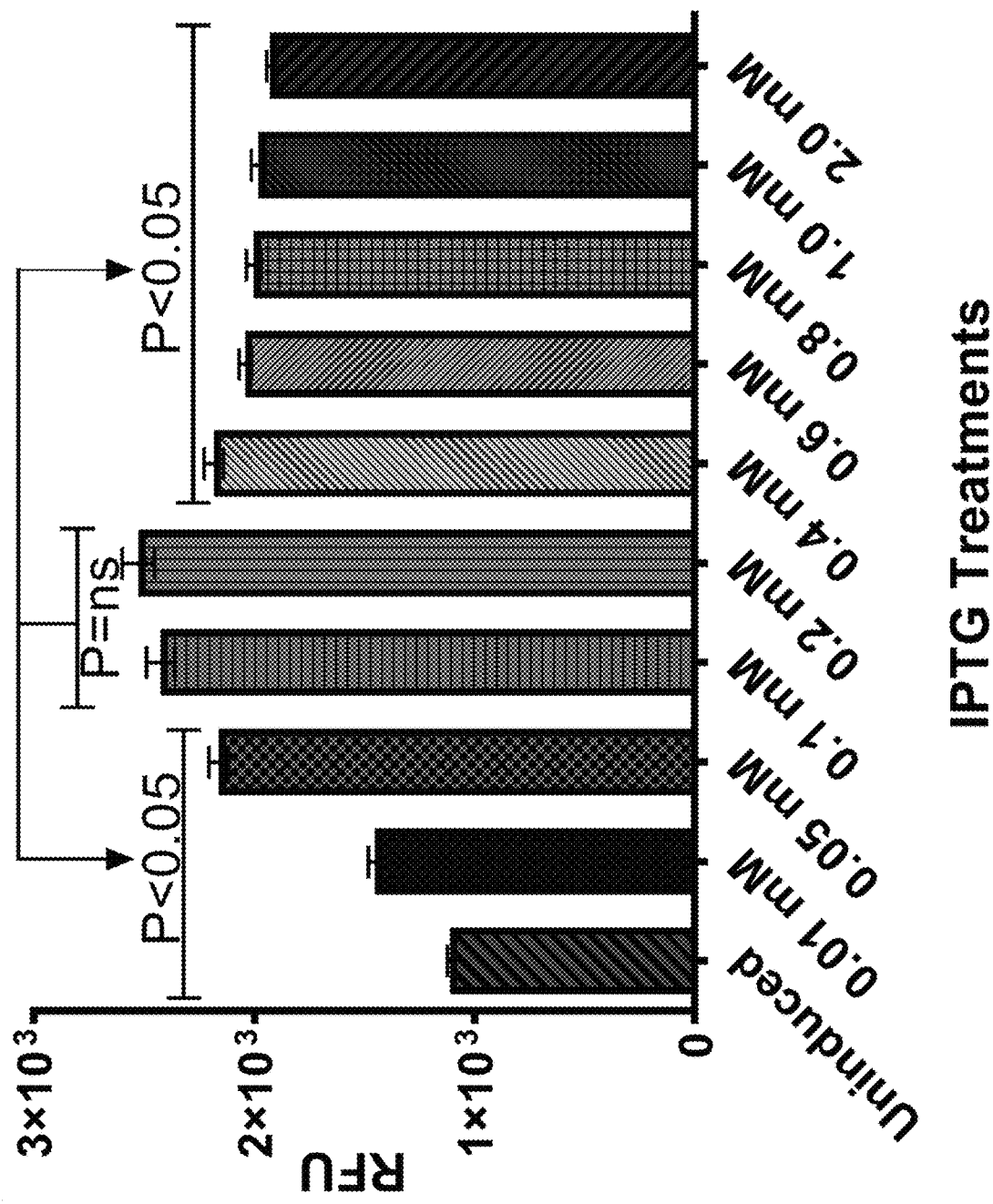

Fluorometric output of induced samples increased with time and were significantly affected by the IPTG concentration used for induction (FIG. 13A). IPTG concentrations of 0.1 and 0.2 mM induced significantly higher fluorescence after 18 h incubation at 26° C. compared to other IPTG concentrations (FIG. 13B).

Concentration Estimation

One millilitre of Ni-NTA purified and buffer exchanged GFP-PlaX and GFP-MunX eluents were lyophilized and analytically weighed off in triplicate to estimate total protein mass. The purified GFP-PlaX and GFP-MunX samples were electrophoretically separated using tricine SDS-PAGE to estimate sample purity (Schägger and von Jagow, 1987). To avoid saturation during Coomassie staining the 10× dilutions of GFP-PlaX and GFP-MunX were used to estimate protein purity. Gel analyzer 2010a was used to determine the pixel density of each stained band in respective lanes and used to estimate sample purity (Lazer and GelAnalyzer, 2010).

Upscaled Production of GFP-PlaX and GFP-MunX

In order to determine the effect of larger scale expressions on the yield of the GFP-fusion system the inventors performed experiments under, respectively, optimized conditions using the Minifors 5 L fermenter. Upscaled heterologous expression of the plantaricin 423 and mundticin ST4SA GFP fusion proteins was performed using a 5 L fermenter (Minifors, Infors AG; 3 L max recommended capacity). Terrific broth (2.7 L), containing 0.005% antifoam 204 (Sigma-Aldrich), was prepared and autoclaved. Once cool, 300 mL of sterile 10× TB buffer and kanamycin (50 µg/mL final concentration) was aseptically added. The broth was heated to 37° C., aerated at 1 L/min with sterile compressed air and stirred at 300 RPM. The pH and dissolved oxygen levels were not controlled.

The starter cultures of *E. coli* BL21 (DE3) pRSF-GFP-PlaX and pRSF-GFP-MunX were used as an inoculum at 1% v/v, for respective expressions. At an $OD_{600nm}$ of 0.6-0.65, expression of the respective GFP fusion proteins was induced using 0.1 mM IPTG (Thermo-Fisher Scientific). Respective fermentations were then cooled to 18° C. and incubated for 48 h.

After extraction, Ni-NTA purification and buffer exchange of the GFP-PlaX and GFP-MunX proteins, 39 mL of GFP-PlaX and 42 mL of GFP-MunX eluent was obtained. After lyophilization of 1 mL GFP-PlaX and GFP-MunX, 12.96 mg and 17.96 mg residual mass was measured, respectively. From SDS-PAGE analysis the purity of GFP-PlaX and GFP-MunX are approximately 72 and 61%, producing approximate concentrations of 9.33 and 10.95 mg/mL, respectively. At these purities, the approximate yield of GFP-PlaX and GFP-MunX was 121.29 mg/L of culture and 153.30 mg/L of culture, respectively.

Antimicrobial Activity Assays

While the respective bacteriocins were fused to GFP and produced a fluorescent complex, it was important to determine that antimicrobial activity was due to the liberated bacteriocin. Antimicrobial activity of plantaricin 423 and mundticin ST4SA was assessed against *Listeria monocytogenes* EDG-e grown on Brain Heart Infusion media (BHI) containing 7.5 mg/mL chloramphenicol. The spot plate method was performed on solid medium (1% w/v agar) seeded with *Listeria monocytogenes* EDG-e. SDS-PAGE separations were assayed for activity by casting the polyacrylamide gel in an agar bilayer seeded with *Listeria monocytogenes* EDG-e. Before casting, the poly acrylamide gels were fixed for 20 min in a 25% isopropanol, 10% acetic acid fixing solution and then rinsed 3×15 min with sterile ultra-pure water.

Cleavage parameters were optimized using a modified method from that supplied by the manufacturer. The WELQut-to-Sample ratios were set to 1:100, 1:50, 1:25, 1:5 (v/v) for 50 µL samples of GFP-PlaX and GFP-MunX, respectively, and diluted to a final volume of 250 µL in WELQut cut buffer. The approximate corresponding units of WELQ to 466.5 µg of GFP-PlaX was 2.5 U, 5 U, 10 U and 50 U respectively. The approximate corresponding units of WELQ to 547.5 µg of GFP-MunX was 2.5 U, 5 U, 10 U and 50 U respectively. Cleavage reactions were incubated at 28° C., and 50 µL samples were collected at 2 h, 4 h, 8 h, and 16 h, respectively. Cleavage was assessed by the spot plate method using BHI solid medium (1% w/v agar) seeded with *Listeria monocytogenes* EGD-e.

Figure 14A:
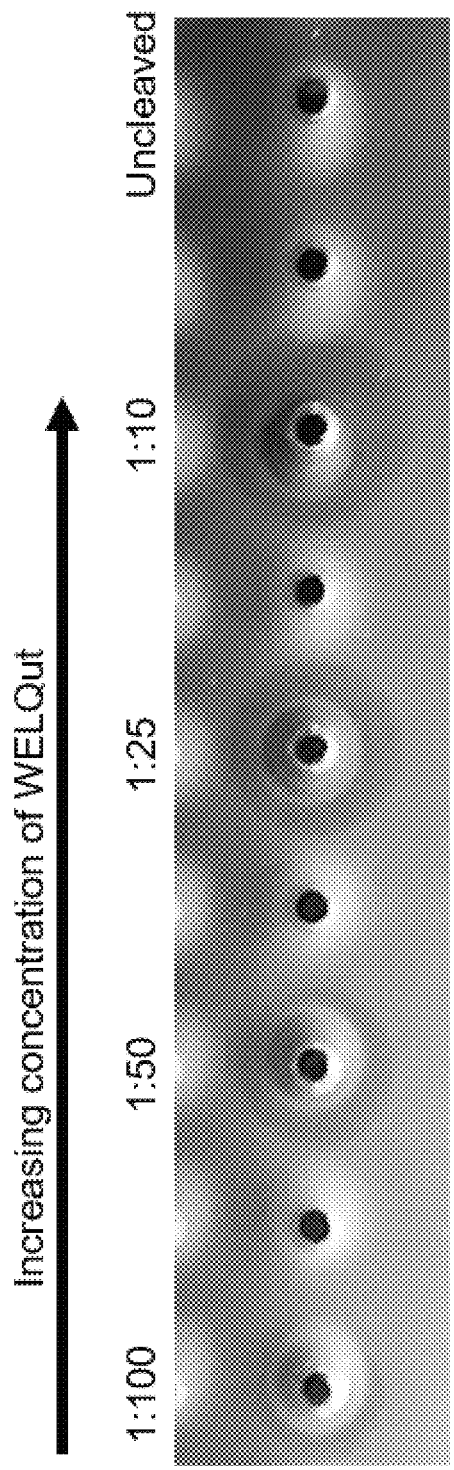
FIGS. 14A and 14B: Antimicrobial activity of plantaricin 423 and mundticin ST4SA at various WELQut: sample ratios. Antimicrobial activity of plantaricin 423 (14A) and mundticin ST4SA (14B) cleaved from Ni-NTA purified GFP-PlaX and GFP-MunX proteins, respectively. Cleavage assessed using the spot plate technique against *L. monocytogenes*. Cleavage ratios of WELQut: sample (mL:mL) indicated on top of panel. Cleavage was performed at 28° C. for 16 h. Post cleavage, 100 ml of GFP-PlaX (14A) and 10 mL GFP-MunX (14B) was spotted from each cleavage reaction. Uncleaved GFP-PlaX (14A) and GFP-MunX (14B) did not show antilisterial activity.
Figure 14B:
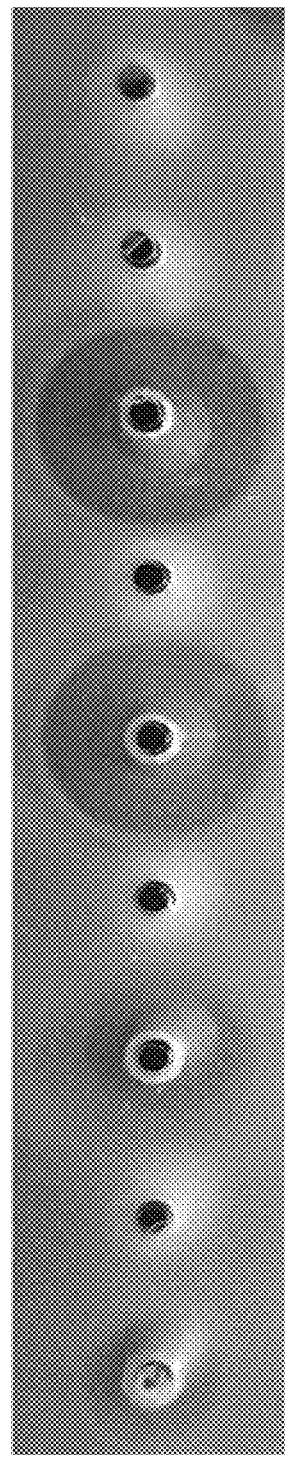

The cleavage ratios which produced maximal antilisterial activity for GFP-PlaX and GFP-MunX cleavage after 16 h was confirmed at a WELQut to sample ratio of 1:10 and 1:25 (mL:mL), respectively (FIG. 14).

An important advantage of using GFP as a fusion partner is the ability to evaluate protease cleavage by visualizing migration patterns of fluorescent bands after electrophoretic separation. Determining optimal cleavage conditions in terms of activity of heterologously produced bacteriocin fusions is dependent on many variables. As such the inventors confirmed the results for optimal cleavage by utilizing the maintained fluorescent properties of GFP after SDS-PAGE electrophoresis. Fluorescent bands were observed for GFP-PlaX, GFP-MunX, and GFP before and after cleavage, respectively. These bands were then correlated to stained bands on the same SDS-PAGE gels (FIG. 15).

The intensity of the uncleaved GFP-PlaX and GFP-MunX fluorescent bands decreases as the WELQut: sample ratio increases (FIG. 15). Complete cleavage could be observed for GFP-PlaX and corresponds to the highest spot activity observed. Complete cleavage was not achieved for GFP-MunX, with a slight fluorescent band observed at the location of uncleaved GFP-MunX.

Figure 16A:
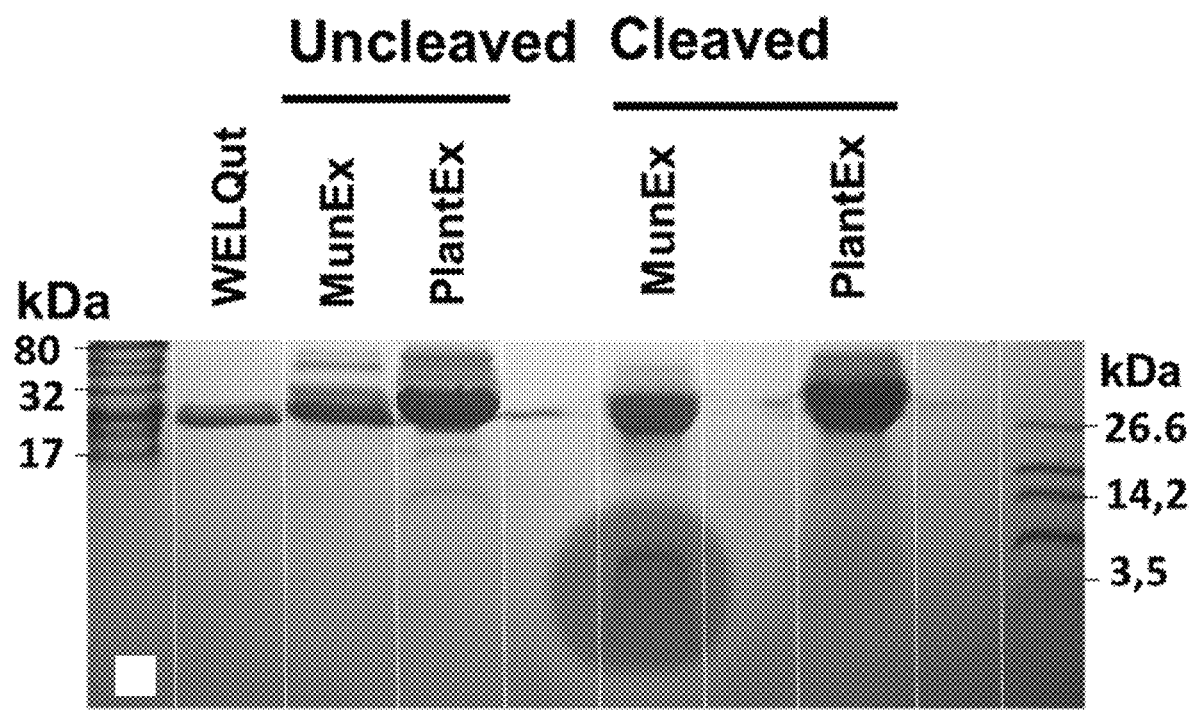
FIGS. 16A-16C: Observed post cleavage antilisterial activity of liberated mundticin ST4SA and plantaricin 423 separated by SDS-PAGE. (16A) Superimposition of duplicate SDS-PAGE separations which indicates the size of bands showing antilisterial activity. (16B) Antilisterial SDS-PAGE overlay showing activity post WELQut cleavage at locations correlating to I—GFP-PlaX, II—GFP-MunX, III—mundticin ST4SA and IV-plantaricin 423. (16C) Location of fluorescent bands in (16A).
Figure 16B:
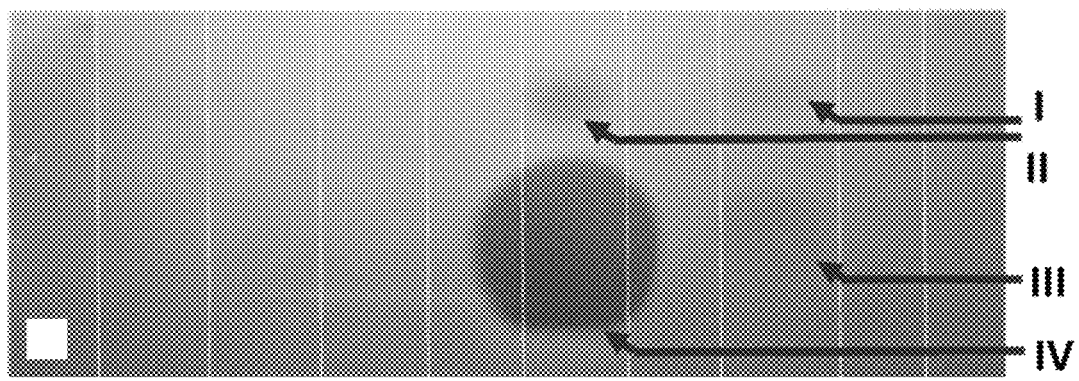
Figure 16C:
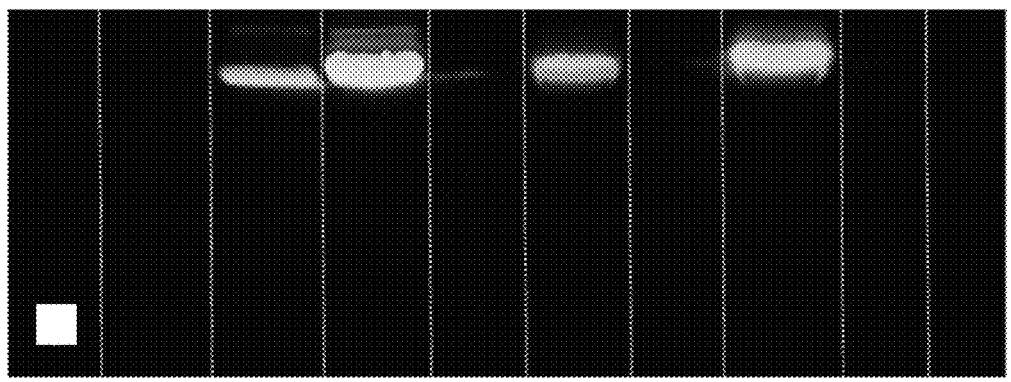

Using SDS-PAGE under semi-native conditions the location of fluorescent GFP fusion proteins on the separated gel could be photographed and superimposed on the stained- and antilisterial gel overlay (FIG. 16). Antilisterial activity was observed as clear zones for the WELQut cleaved GFP-PlaX and GFPMunX samples. Antilisterial zones III and IV in FIG. 16 correspond to the locations of mundticin ST4SA (4285 Da) and plantaricin 423 (3928 Da), respectively, indicating liberation of the core peptides from their respective GFP fusion partners. However, two additional zones of antilisterial activity (I and II in FIG. 16) were observed, which correspond to the approximate size and location of fluorescent GFP-MunX (31 874 Da) and GFP-PlaX (31 520 Da).

HPLC and LC-ESI-MS

Mundticin ST4SA and plantaricin 423 were cleaved from one millilitre of His-tag purified GFP-MunX and GFP-PlaX, respectively, under optimal cleavage conditions. Cleavage reactions were purified using high performance liquid chromatography (HPLC), single peaks were spot tested for antilisterial activity.

Figure 17A:
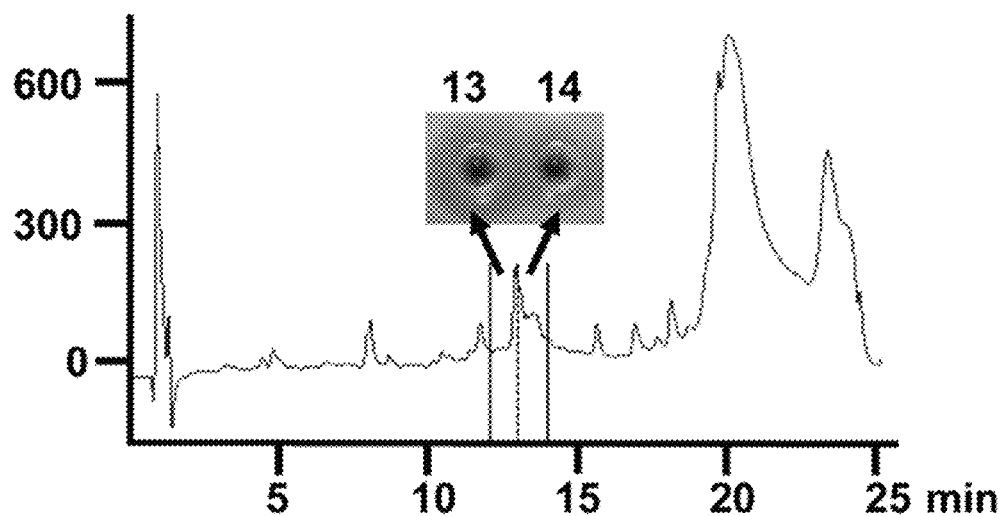
FIGS. 17A and 17B: HPLC purification and accurate mass determination of mundticin ST4SA liberated from GFP-MunX. (17A) HPLC fractionation of WELQut cleaved GFP-MunX mixture with antilisterial activity identified in fractions 13 and 14. (17B) Segment of raw mass spectrum showing the observed m/z isotopic envelopes of mundticin ST4SA carrying +5 charges ([M+5H]C5 expected m/z 858.0232). The monoisotopic peak in (17B) is indicated with an arrow and corresponds to an accurate mass measurement of 4258.1355 Da, which is in agreement with the exact mass of mundticin ST4SA with one disulfide bond (4285.0796 Da).
Figure 17B:
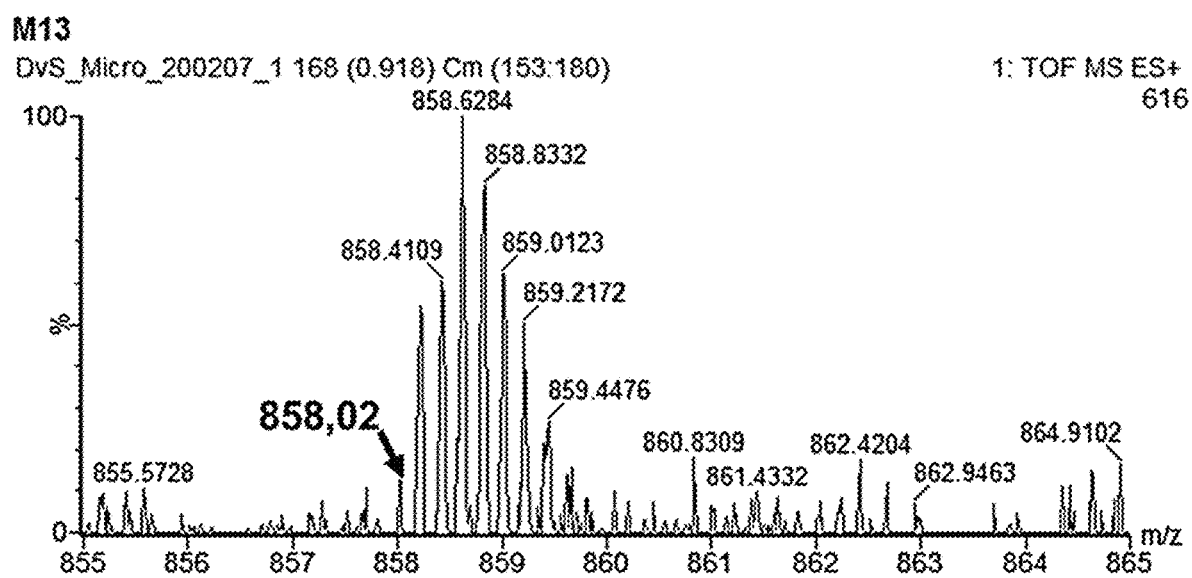

Electrospray ionization-MS performed on HPLC-purified mundticin ST4SA confirmed the presence of a peptide with a mass corresponding to mature mundticin ST4SA (FIG. 17). While an accurate mass of 4285.1355 Da was determined for mundticin ST4SA from the isotopic envelope of the $[M+5H]^{+5}$ species, the abundance of this charged species within the raw spectrum was low (FIG. 17). However, the accurate mass measurement is in close agreement with the theoretical monoisotopic mass of 4285.0796 Da (equivalent to the formation of one disulfide bridge).

Mundticin ST4SA activity was observed from a single peak while plantaricin 423 produced multiple active peaks with low levels of activity. The mundticin ST4SA fraction was lyophilized and the residual mass was weighed off. Optimal cleavage of GFP-MunX yielded 0.88 mg of active mundticin ST4SA, indicating that approximately 37.3 mg could be obtained from the 3 L fermentation corresponding to 12.4 mg/L mundticin ST4SA.

Using the methods described in example 2 above, the inventors expressed antimicrobially active bacteriocins. The inventors also illustrated the potential of upscaling the system by using larger scale fermentation reactors. The inventors were able to accurately and quickly evaluate expression by taking advantage of the fluorescent properties of the fusion proteins in vitro and in vivo.

Example 3

Production of GFP-Fused Bacterial Toxins Lysteriolysin (LLO) and ActA in *E. coli*

Figure 18:
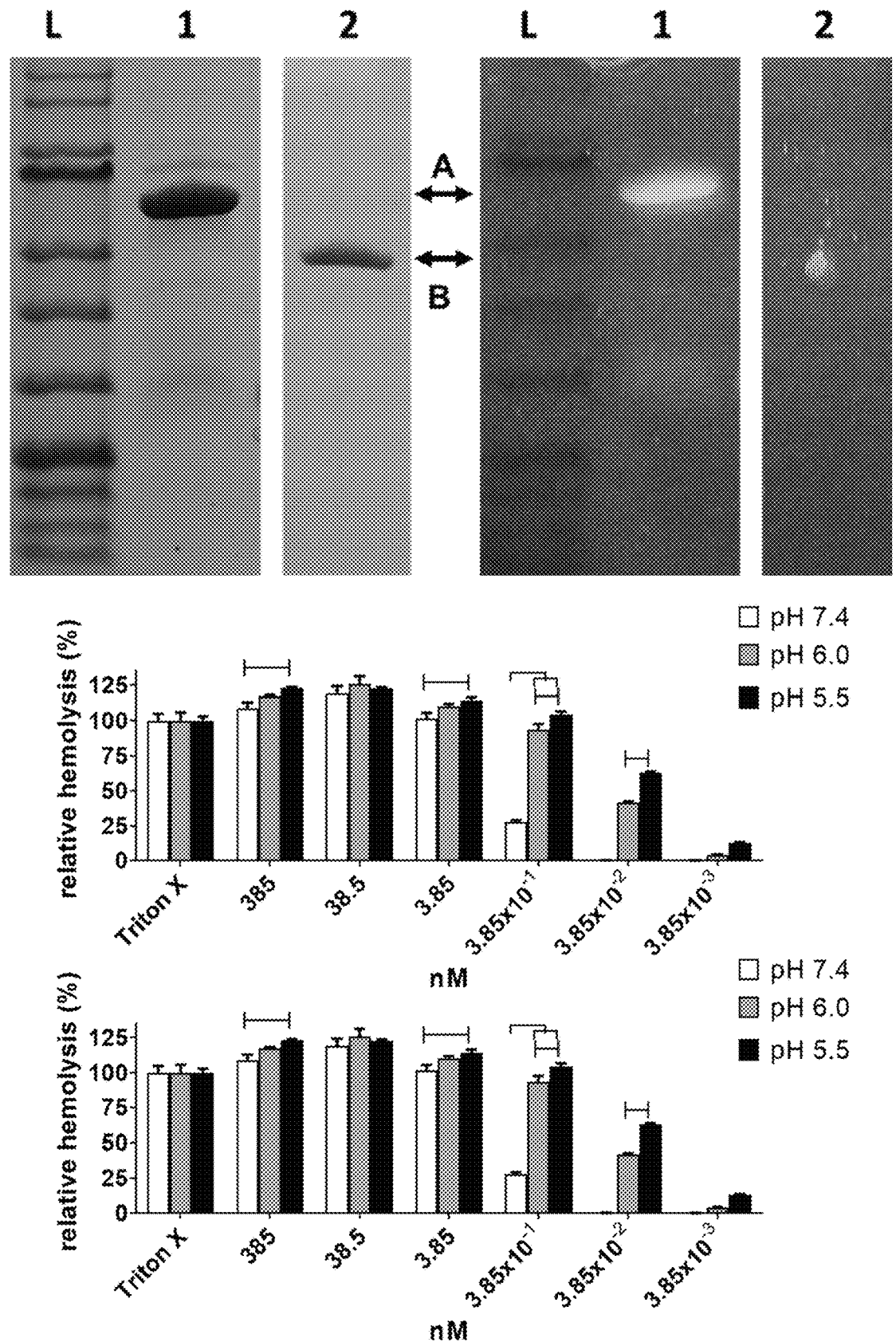
FIG. 18: Top Panel-SDS-PAGE of purified GFP-LLO and LLO used in erythrocyte lysis assay. Left: Stained gel. Right: Fluorescent image of GFP-LLO and GFP, L: Ladder (NEB ladder #P7712), 1: Uncut GFP-LLO, 2: Cleaved, IMAS purified and desalted LLO. A: GFP-LLO, B: LLO. Bottom Panel-Erythrocyte haemolysis following GFP-LLO exposure at varying pH. Relative haemoglobin absorbance was collected at 540 nm, values expressed as percentage of positive control, mean±SEM (n=3), Analysis via t-test concluded *=$p<0.001$, ***=$p<0.0001$ vs Untreated.
Figure 19:
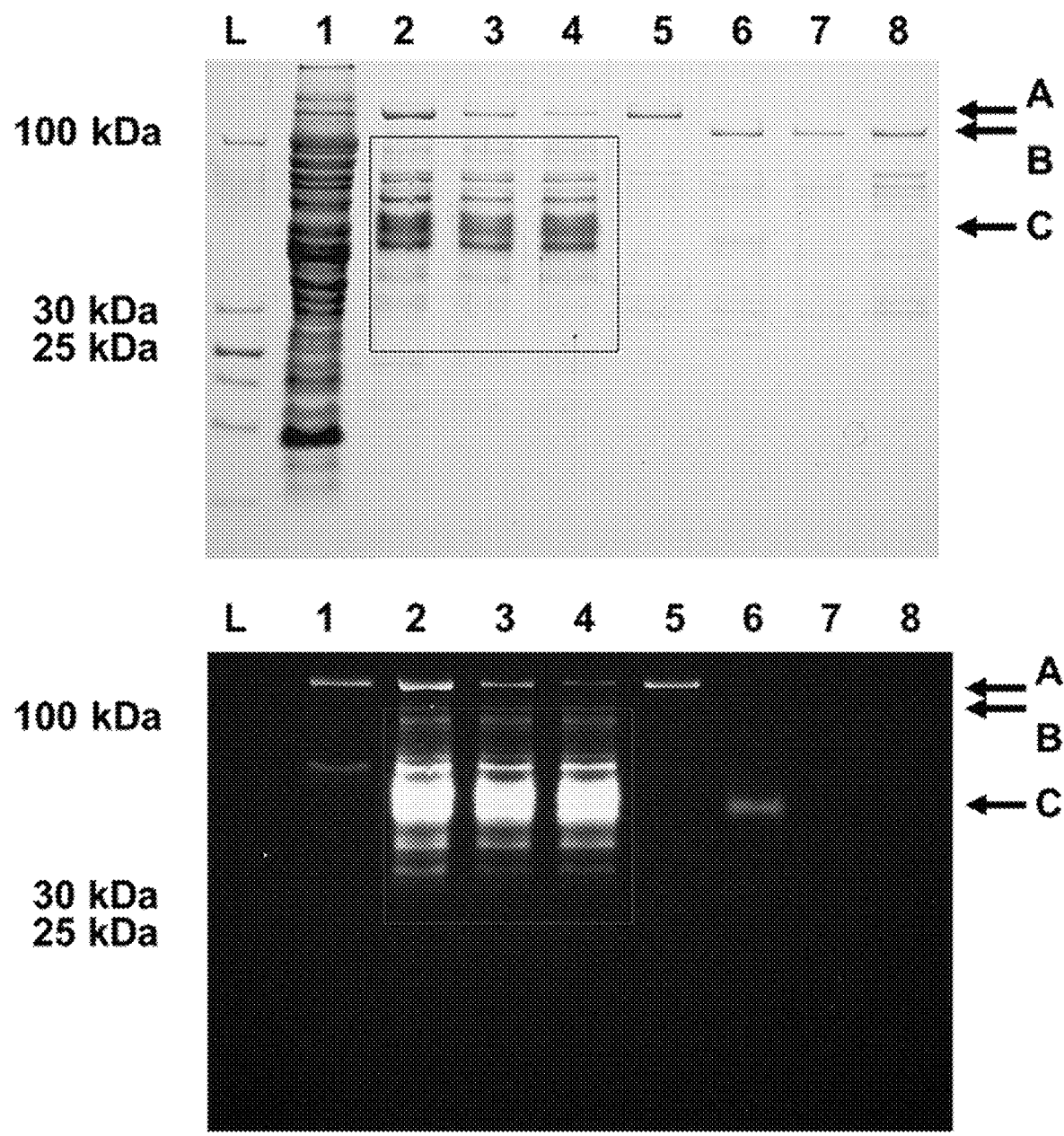
FIG. 19: SDS-PAGE of GFP-ActA-GST purification. Left: Stained gel, Right: Fluorescent image of GFP-ActA-GST and GFP. L: Ladder (PageRuler #26632), 1: IMAC flow through, 2: IMAC elution containing GFP-ActA-GST, 3: Dilution of IMAC elution before GST purification, 4: Flow through for GST column, 5: Elution from GST column containing GFP-ActA-GST, 6: WELQut protease cleavage of GFP-ActA-GST eluted from GST column, 7: Flow through from IMAC column containing ActA-GST after WELQut digestion, 8: Desalted and concentrated ActA-GST obtained from IMAC flow through. A: GFP-ActA-GST, B: ActA-GST, C: GFP. Degradation products are shown in the box.

The inventors of the present invention have shown successful expression of the bacterial toxin Listeriolysin O (FIG. 18) and ActA (FIG. 19).

Plasmid Design

The *Listeria monocytogenes* effectors LLO and ActA, were translationally fused to green fluorescent protein (GFP) and expressed in *Escherichia coli*. Generation of a backbone plasmid containing mgfp5 including an N-terminal 6× polyhistidine-tag (His tag) and C-terminal WELQut protease site was done as explained in examples 1 and 2. The LLO gene was amplified from *L. monocytogenes* EDG-e genomic DNA using the primers listed in Table 5, with the forward primer designed to exclude the N-terminal signal peptide (SEQ ID NO:66-67). Digested (PstI/NotI) and purified LLO was cloned into pRSF-GFP on a PstI/NotI fragment using T4 ligase, resulting in the translational fusion of LLO to His tagged GFP having the amino acid sequence of SEQ ID NO:37 and the nucleotide sequence of SEQ ID NO:38. The resulting pRSFGFP-LLO construct was transformed into chemically competent *E. coli* BL21 (DE3) cells.

TABLE 5

Primers used in GFP-Fused LLO and ActA expression in *E. coli*.

| ID | Primer Name | Primer Sequence | SEQ ID NO: |
|---|---|---|---|
| 1 | GST_NotI_F | GCGCGGCCGCGTCCCCTATACTAGGTTATTGGAAA | SEQ ID NO: 64 |
| 2 | GST_XhoI_R | CAGACTCGAGTTACGATTTTGGAGGATGGTCGCCA | SEQ ID NO: 65 |
| 3 | WLLO_PstI_F | GGGAACTGCAGGCATCTGCATTCAATAAAG | SEQ ID NO: 66 |
| 4 | LLO_NotI_R | ATTATGCGGCCGCTTATTCGATTGGATTAT | SEQ ID NO: 67 |
| 5 | WActA_PstI_F | GGGAACTGCAGGATAGCGAAGATTCTAGTCTAAACAC | SEQ ID NO: 68 |
| 6 | ActA_NotI_R | ATGCGGCCGCTTACGTCGTATGGTTCCCTG | SEQ ID NO: 69 |

Several plasmid constructs were generated for the expression of ActA, due to degradation products observed during the expression and purification of ActA. The final construct resulted in the translational fusion of ActA to His tagged GFP on its N-terminal and a GST tag on the C-terminal having the amino acid sequence of SEQ ID NO: 39 and the nucleotide sequence of SEQ ID NO:40. ActA was amplified from *L. monocytogenes* EDG-e gDNA with the primers designed to exclude the N- and C-terminal signal peptide and transmembrane domain, respectively (SEQ ID NOs: 68-69). The GST tag was amplified from pET41a(+) using primers listed in Table 5 (SEQ ID NOs: 64-65). Purified ActA PCR product was digested with PstI/NotI and ligated into pRSFGFP previously digested with PstI/NotI. The ligation product was transformed and purified. The resulting pRSFGFP-ActA construct was digested with NotI/XhoI and used in a ligation reaction with the GST tag (digested with NotI/XhoI). The product from the ligation reaction was used to transform chemically competent *E. coli* BL21 (DE3) cells and pDNA isolated as described previously. Stability of ActA during expression was increased using an *E. coli* strain, ArcticExpress, harbouring the cold-adapted chaperonins Cpn10 and Cpn60. Transformation and culturing of ArcticExpress was performed as described for *E. coli* BL21 (DE3) with the exception of gentamicin (20 µg/mL) being included in order to maintain the plasmid harbouring cpn10 and cpn60.

Protein Synthesis and Purification

Listeriolysin-O: *E. coli* expressing GFP-LLO was performed a similar manner as explained in examples 1 and 2. Eluent from His tag purification was desalted against PBS (pH 7.4) using 10 kDa spin columns. Protein concentration for yield determination of desalted proteins were determined using the BCA protein assay.

Using optimal cleavage conditions, LLO was further purified to remove GFP and WELQut (also His tagged) (FIG. 18). Imidazole was added at 10 mM and applied to an equilibrated His Trap HP Ni-NTA column. LLO containing flow through was collected and purified LLO was desalted with PBS (pH 7.4) using 10 kDa protein concentrators.

Actin Assembly-Inducing Protein: Purification of GFP-ActA-GST was done in a similar manner to that of GFP-LLO except for an additional GST tag purification step (FIG. 19). *Escherichia coli* ArcticExpress cells expressing GFP-ActA-GST were inoculated in LB broth containing 50 µg/mL kanamycin and 20 µg/mL gentamycin and incubated overnight at 30° C. under agitation. This was inoculated in 500 mL TB (2% v/v) containing 50 µg/mL kanamycin and 20 µg/mL gentamycin. Flasks were incubated at 30° C. while shaking until an $OD_{600nm}$ of 0.5 was reached. Cells were induced with 0.5 mM IPTG and allowed to express at 26° C. with agitation for 18 hours. Cells were collected via centrifugation at 6164×g for 20 min at 10° C. and lysed as described previously. All subsequent purification steps were done on ice to reduce degradation of GFP-ActA-GST. Prior to protein isolations via IMAC, His Trap HP Ni-NTA His tag columns were equilibrated with SB containing 20 mM imidazole (SB20) supplemented with protease inhibitors, followed by application of supernatant. Columns were washed twice, first with SB20 containing protease inhibitors followed by PBS containing 20 mM imidazole (PBS20) before eluting GFP-ActA-GST with PBS containing 125 mM imidazole. The eluent was diluted 1:1 in PBS (pH 7.4) and supplemented with dithiothreitol (DTT) at a final concentration of 5 mM. The diluted eluent was applied to a column packed with glutathione agarose (2 mL) and circulated for 1 hour to allow adequate binding of GST-tagged protein. Columns were washed with PBS (pH 7.4) and bound GFP-ActA-GST eluted with PBS containing 10 mM reduced glutathione (pH 8).

Liberation of ActA-GST from GFP was achieved with WELQut cleavage (FIG. 19). The GST-tag purification eluent was cleaved with 10 U WELQut protease per millilitre of eluent and incubated for 16 hours at 8° C. After cleavage, imidazole was added at 10 mM and applied to a His Trap HP Ni-NTA column pre-equilibrated with 10 mM imidazole. The liberated ActA-GST flow through was collected and desalted in 4-(2-hydroxyethyl)-1-piperazineethanesulfonic acid (HEPES) buffer (20 mM HEPES, 50 mM KCl; pH 7.5) using a 10 kDa protein concentrator and protein yield determined. Samples were collected throughout purification and cleavage reactions for analysis by SDS-PAGE as described in examples 1 and 2.

Using the methods described in example 3 above, the inventors expressed Listeriolysin O (LLO) at a yield 15 times (51 mg/L vs 3.4-8 mg/L) greater than that reported in the prior art. Using non-optimised conditions (1 L of media) the inventors were able to produce pure LLO. Additionally, it was shown that the LLO fused to its fluorescent partner still has activity. To further demonstrate the versatility of the method and how it can quickly be used for optimization for other peptides, the inventors of the present invention used the methods described herein to produce another bacterial toxin ActA which is prone to degradation (FIG. 19). Specifically, the inventors of the present invention were able to quickly evaluate that the protein of interest was being degraded by monitoring fluorescence of the fluorescent fusion partner and based on this observation, were able to prevent degradation by implementing a dual purification setup in order to obtain pure product.

Example 4

Lytic Protein Expression in *E. coli*

The inventors have identified two highly active lytic proteins from lambda Phage, namely GpR (SEQ ID NO: 15) and GpE (SEQ ID NO: 17). For proof of concept GpR was used to determine the capability of GpR to induce the lysis of *E. coli*. The gpR gene (endolysinR-NP_040645.1) was PCR amplified from lambda phage using GpR-F and GpR-R primers (SEQ ID NOs: 70 and 71). The gpE gene (lysozyme murein hydrolase-YP_002854084.1) was PCR amplified from T4 phage using GpE-F and GpE-R primers (SEQ ID NOs: 72 and 73). The amplified product was cloned into the second multiple cloning site of pRSFGFP using the restriction enzymes BglII and KpnI to yield pRSFGFPGpR and BglII and XhoI to yield pRSFGFPGpE.

TABLE 6

Primers used in lytic protein expression in *E. coli*.

| ID | Primer Name | Primer Sequence | SEQ ID NO: |
|---|---|---|---|
| 1 | GPR-F | ATGGCAGATCTGGTAGAAATCAATAATCAA | SEQ ID NO: 70 |
| 2 | GPR-R | ATAGGTACCTCATACATCAATCTCTCTGACCGT | SEQ ID NO: 71 |

TABLE 6-continued

Primers used in lytic protein expression in *E. coli*.

| ID | Primer Name | Primer Sequence | SEQ ID NO: |
|----|-------------|-----------------|------------|
| 3 | GPE-F | ATGGCAGATCTGAATATTTTTGAAATGCTG | SEQ ID NO: 72 |
| 4 | GPE-R | CAGACTCGAGTTACAGATTTTTATATGCAT | SEQ ID NO: 73 |

Example 5

Proof of Concept for the Regulation of Lytic Protein Expression Using an RNA Thermometer To illustrate proof of concept for the use of an RNA thermometer to reduce the metabolic load of GpR on *E. coli* cells the inventors utilized RNA thermometer U7Tap (SEQ ID NO:19) for the production of recombinant His tagged GFP. pRSF-Duet1 was used as the backbone plasmid for generation of pTAP (RNA thermometer backbone vector). The selected RNA thermometer results in down regulation of gene expression at lower temperatures with increased translation at higher temperatures. GpR was digested out of pRSFGFPGpR using BglII-XhoI and cloned into the newly generated pTAP (SEQ ID NO:36) plasmid on a BglII-XhoI site placing the autolysin under the control of the P7 promoter and the included RNA thermometer. After ligation and transformation cells were plated onto BHI agar supplemented with kanamycin (50 μg/mL). Positive clones were identified and used for further validation.

For proof of concept, cells harbouring pRSFGFP (CONTROLGFP); pRSFGFPGpR (GFPGPR) and pTAPGFPGpR (GFPRTGPR), all these constructs will express recombinant His tagged GFP in addition to the lytic proteins indicated for GFPGPR and GFPRTGPR. were inoculated in BHI broth supplemented with kanamycin (50 μg/mL) and incubated at 26° C. with aeration for 18 h. This culture was then used to inoculate 200 mL of terrific broth supplemented with kanamycin and incubated at 26° C. under aeration. When the $OD_{600nm}$ readings reached 0.1-0.2 the cells were moved to 18° C. and incubated until and OD of 0.55-0.6 was reached. The cells were subsequently induced with induced with 0.125 mM IPTG and incubated at 18° C. for 12 h. After incubation the respective cultures harbouring the different vectors were split into 2 flasks each and these were incubated at 26° C. and 37° C., respectively. Samples were collected at 3 h, 6 h, 9 h and placed at 8° C. until further use. At each time point cells were diluted 1/10 and OD readings taken at 595 nm to determine cell density. At 9 h samples were centrifuged and pellets frozen at −20° C. for at least 1 h. Samples (400 μL each) were allowed to thaw at room temperature after which SB buffer (Table 7) and SB supplemented with 1% SDS was added to half the original volume (200 μL) and incubated proprietary at 37° C. with occasional mixing for 1-2 h. After incubation OD readings were taken at 595 nm to determine extent of cell lysis. The amount of His tagged GFP that could be obtained from samples incubated for 9 h was evaluated using immobilized metal ion chromatography. Two mL of each respective sample (different temperature and construct samples) were centrifuged, and pellets frozen at −20° C. for at least 1 h. Samples were allowed to thaw at room temperature and 1 mL buffer added (Lysis buffer for CONTROLGFP and SB buffer supplemented with 1% SDS for GFPGPR and GFPRTGPR). In all cases buffers were supplemented with DNAse, RNAse and incubated at 37° C. with occasional mixing for 1-2 h.

Samples containing the CONTROLGFP construct were lysed according to standard procedures as described in example 1 with GFPGPR and GFPRTGPR lysed using SB buffer supplemented with 1% SDS as described above. After lysis samples were centrifuged at 12000 rpm to pellet cell debris and non-lysed cells. The supernatant of the samples was removed, and imidazole added to a final concertation of 5 mM and 600 μL was subsequently added to a HisPur (ThermoScientific) spin columns to bind His tagged GFP. The spin columns were washed three times with SB buffer supplemented with 5 mM imidazole. Finally, GFP was eluted with 600 μL SB buffer supplemented with 500 mM imidazole. These samples were subsequently used for SDS-PAGE analysis.

Figure 20:
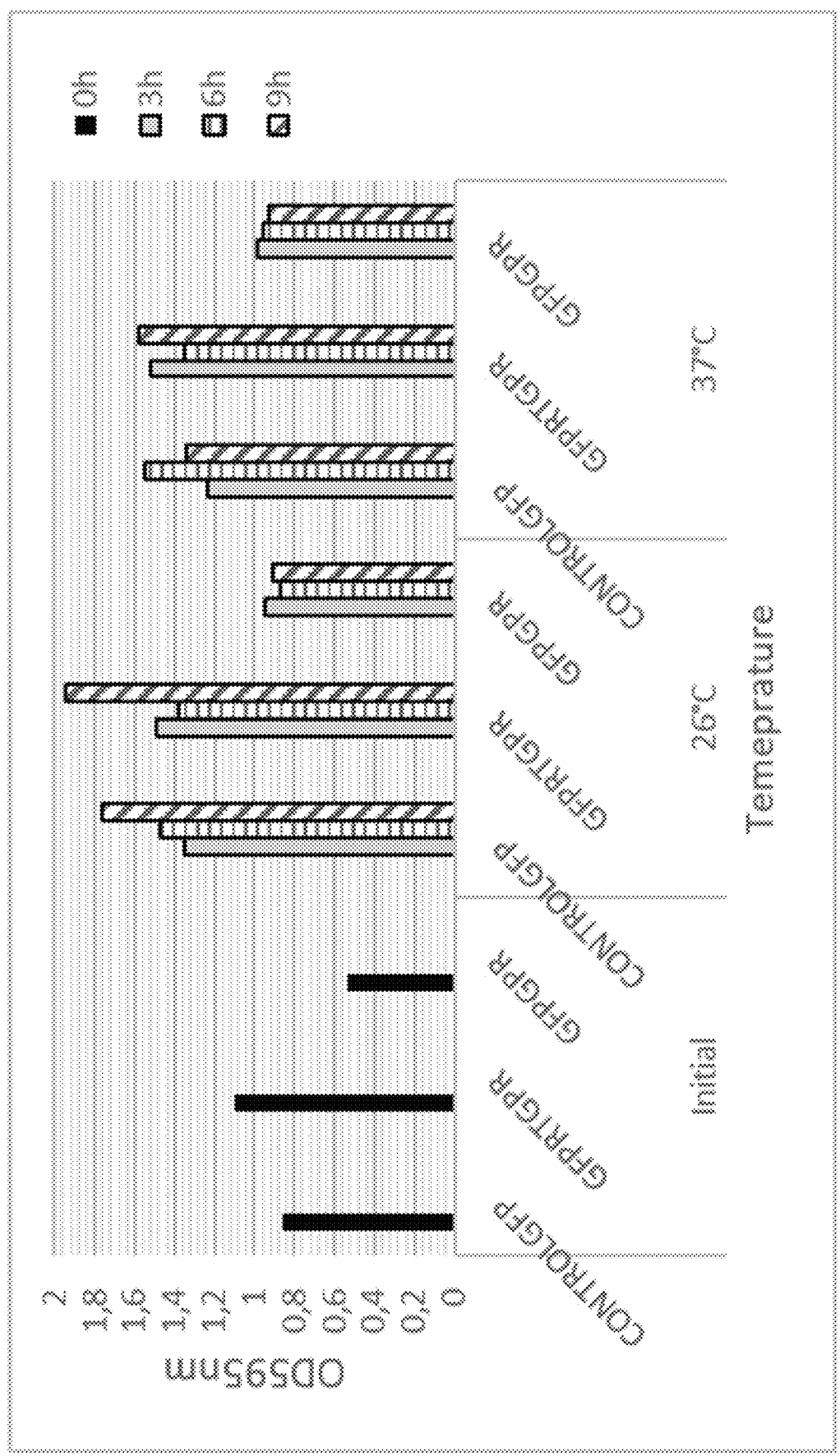
FIG. 20: Optical density of cell cultures taken directly after removal from 18° C. expression temperature (initial). Subsequent readings were taken after incubation at either 26° C. or 37° C. for 3 h, 6 h and 9 h. Optical density readings were taken at 595 nm using a microplate reader. CONTROLGFP=cells harbouring pRSFGFP expressing GFP. GFPRTGPR=cells harbouring pTAPGFP-GPR expressing GFP and GpR regulated by an RNA thermometer. GFPGPR=cells harbouring pRSFGFP-GpR expressing GFP and GpR.

The inclusion of the RNA thermometer (GFPRTGPR) resulted in consistently higher optical density readings compared to the cells harbouring either the CONTROLGFP or GFPGPR constructs (FIG. 20). Additionally, the lack of an RNA thermometer in the GFPGPR construct resulted in consistently lower optical density readings, indicative of high metabolic load and potential toxicity (FIG. 20).

Figure 21:
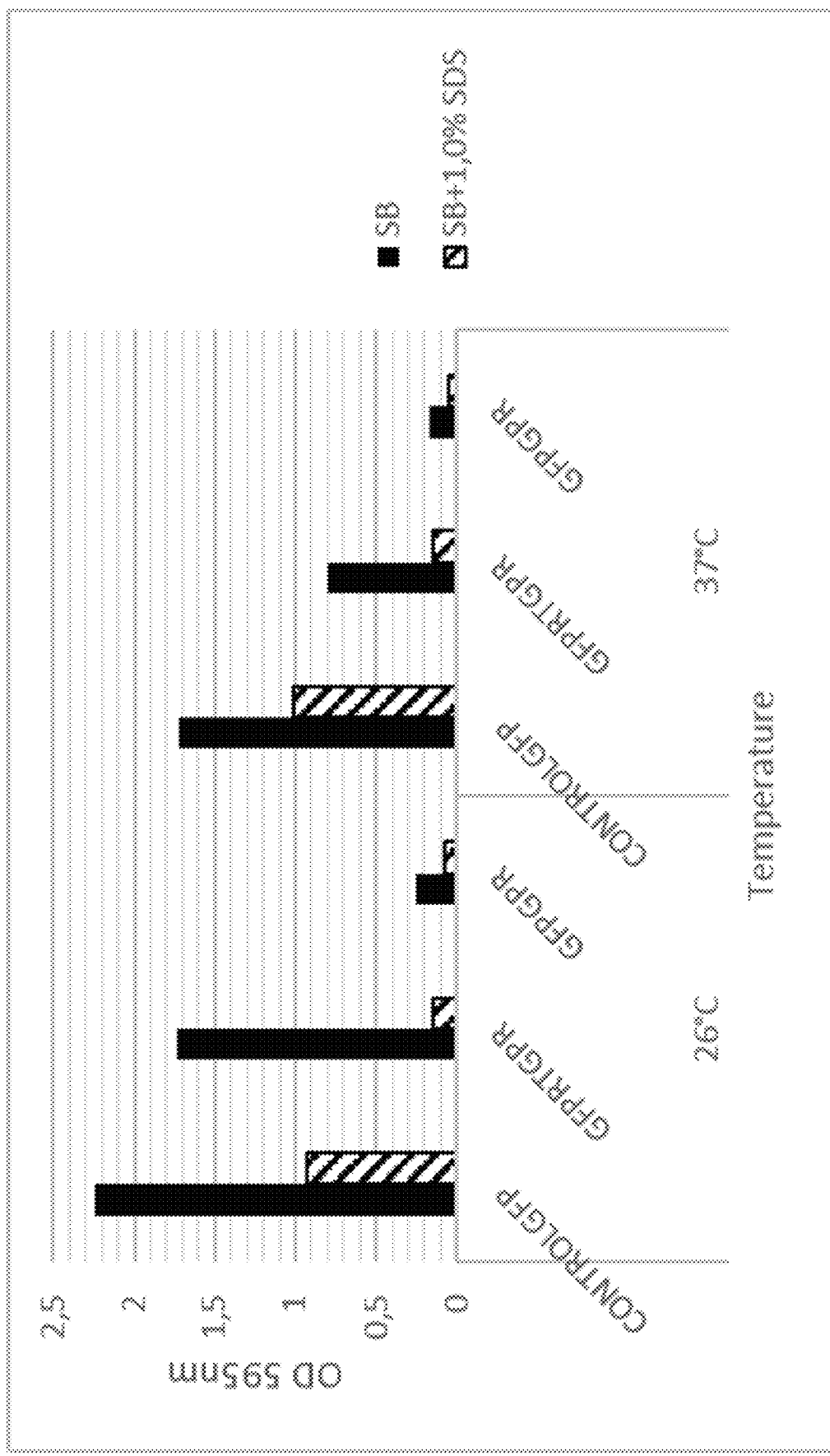
FIG. 21: Lysis of cells after freeze thaw cycle and resuspension in lysis buffer. Cells incubated at 26° C. or 37° C. for 9 h after expression were frozen, allowed to thaw and resuspended in either SB or SB supplemented with 1% SDS and incubated at 37° C. Optical density readings were taken at 595 nm using a microplate reader. CONTROLGFP=cells harbouring pRSFGFP. GFPRTGPR=cells harbouring pTAPGFP-GPR and GFPGPR=cells harbouring pRSFGFP-GpR.

Pronounced lysis was observed for the construct without the RNA thermometer irrespective of whether the cells were grown at 26° C. or 37° C. (FIG. 21). However, inclusion of the RNA thermometer in the GFPRTGPR constructs resulted in ~2 fold less lysis at 26° C. compared to 37° C. when resuspended in SB buffer, indicating successful throttling of GpR expression when cells are grown at 26° C. (FIG. 21). Addition of 1% SDS to either cells harbouring the GFPGPR or GFPRTGPR construct resulted in complete lysis of cells (FIG. 21). This indicates that the chosen RNA thermometer was capable of throttling expression at 26° C. but does not completely inhibit translation of GpR at this temperature. This also illustrates the potency of the selected autolytic protein. Cells harbouring just the CONTROLGFP construct were also influenced by freeze-thawing and the addition of SDS but not to the same extent as cells harbouring either GFPGPR or GFPRTGPR.

Figure 22:
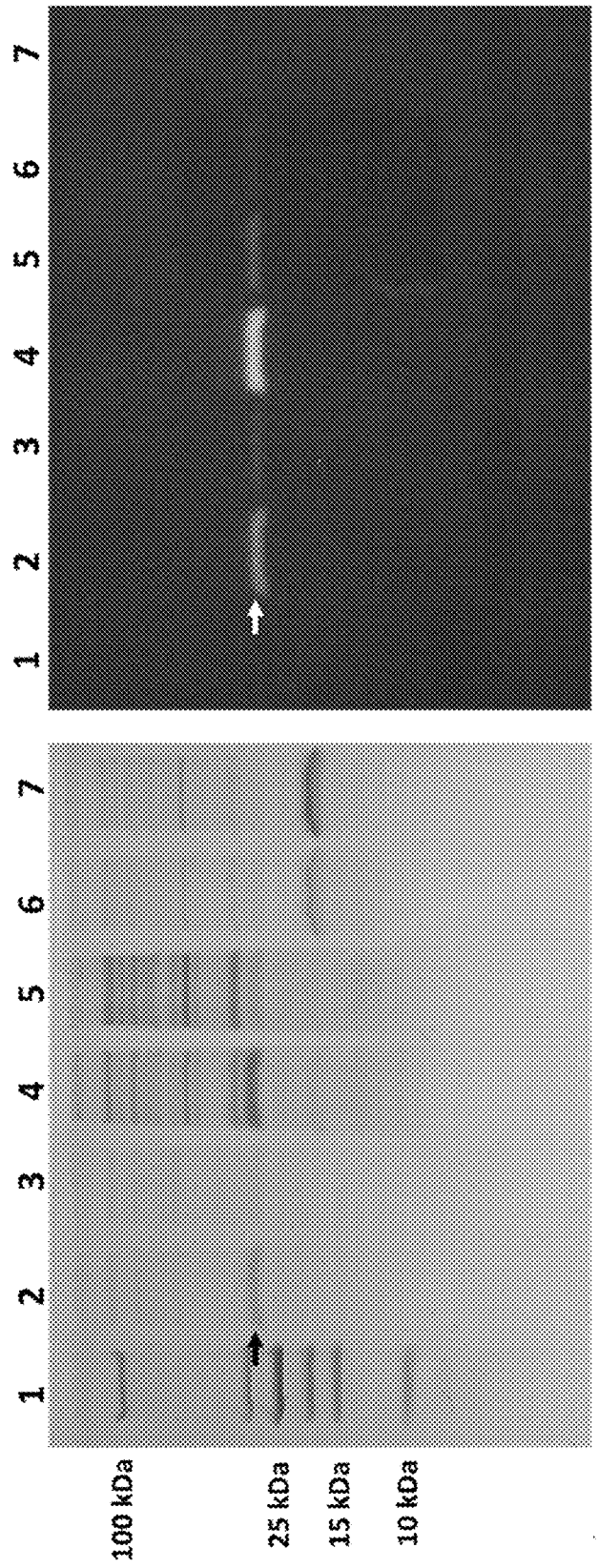
FIGS. 22A-22C: SDS PAGE analysis of small scale His tag purifications. 22A) Stained SDS PAGE gel (arrow indicates band corresponding to GFP). 22B) Fluorescence of GFP in SDS PAGE from (22A). 1=Ladder; 2=CONTROLGFP 26° C.; 3=CONTROLGFP 37° C.; 4=GFPRTGPR 26° C.; 5=GFPRTGPR 37° C.; 6=GFPGPR 26° C. and 7=GFPGPR 37° C. 22C) Comparison of GFP band intensity fold changes between different samples. Band intensity was determine using ImageJ software. Images taken using FluorSee prototype using white light or blue light with Amber filter for fluorescence.

Lysis of cells using standard lysis protocols resulted in incomplete lysis. Both GFPGPR and GFPRTGPR samples indicated complete lysis with the addition of 1% SDS with no incomplete lysis of cells observed. The lack of a RNA thermometer resulted in substantially reduced amounts of GFP, indicating lower expression of GFP (FIG. 22). However, addition of the RNA thermometer resulted more recombinant GFP compared to both the CONTROLGFP and GFPGPR constructs. Analysis using SDS PAGE indicated that temperature and addition of the RNA thermometer had an influence on the amount of GFP that could be obtained (FIG. 22). In all cases incubation of cells at 37° C. resulted in reduced GFP and may be due to stability of GFP at this temperature. The inclusion of the RNA thermometer resulted in up to 4 fold and 2.8 fold more GFP compared to CONTROLGFP (when cells were grown at 26° C. or 37° C., respectively). Compared to the GFPGPR sample the inclusion of the RNA thermometer resulted in a 30 fold and 11-fold increase in the amount of GFP (when cells were grown at 26° C. or 37° C., respectively).

In example 5 the inventors have illustrated that the inclusion of an RNA thermometer resulted in i) increased yield of recombinant GFP after His tag purification compared to what could be obtained from the control (CONTROLGFP) and the GFPGPR construct lacking the RNA thermometer and ii) increased lysis of cells at higher temperatures. The inclusion of the RNA thermometer was also shown to be essential for proper expression of recombinant His tagged GFP as well as proper growth of cells when compared to the GFPGPR construct lacking the RNA thermometer. RNA thermometers with different temperature sensitivities can be included to alter the stringency of lytic protein expression as well as any other recombinant protein that would require controlled expression in addition to standard induction or autoinduction control.

Example 6

Production of GFP-Fused and mCherry-Fused Autophagic Peptide TATBeclin in *E. coli*

Figure 23:
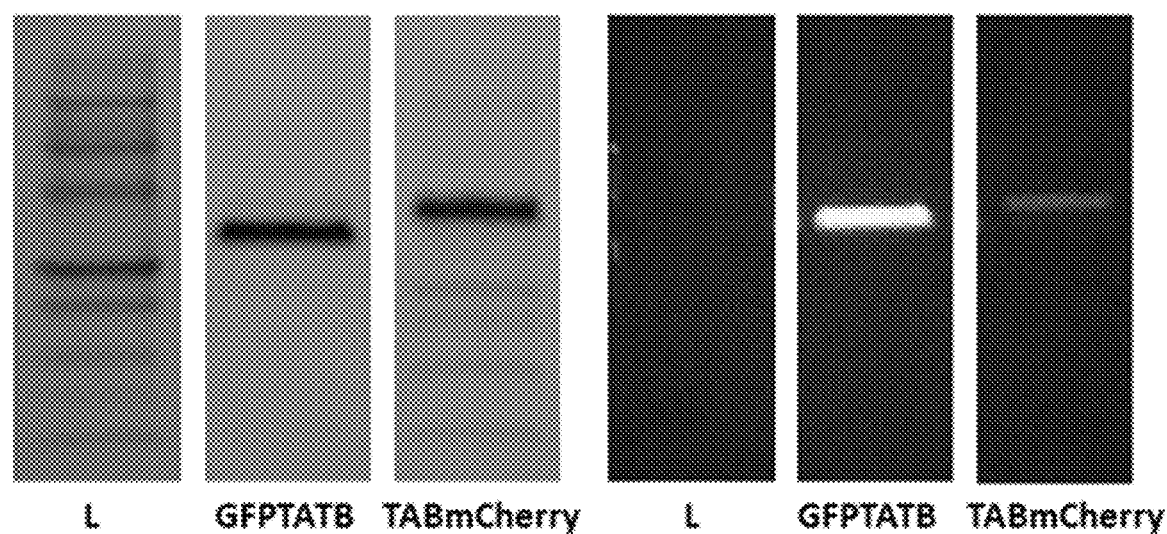
FIG. 23: SDS-PAGE stained gels and GFP fluorescent images representing GFPTATB and TATBmCherry. Left Coomassie stained gel; Right images taken under blue light.

Using the method set out in example 1-5 above, the inventors have produced an autophagic peptide TATBeclin fused to both GFP and mCherry (FIG. 23). This peptide was bioactive even while attached to the fluorescent fusion partners, adding functionality in terms of visualization and tracking capabilities.

The goal here was to reconstruct the TAT-Beclin construct so that it can be fused to either GFP or mCherry. In the case of GFP, TATBeclin (32.96 kDa) is fused to the C-terminal of GFP with a protease site (WELQut) between GFP and TATBeclin. For mCherry, TATBeclin is N-terminally His tagged and fused to mCherry at its C-terminal (34.37 kDa).

TATBeclin was synthesized by using two long primers with homology in the middle (SEQ ID. 74 and 75). This construct was used to generate GFP-TATBeclin (GFPTATB) (SEQ ID 76 and 77).

These two primers were made up to 100 uM stocks in fresh 10 mM Tris (pH 8.0). Klenow (NEB) was used to build in nucleotides and fuse TatBecF and TatBecR (SEQ ID. 74 and 75). A reaction mixture of 50 uL using buffer M (10×, Roche), primer stocks (1 uL each; equal to 2.2 ug each) and Klenow (3 μL) was made up and incubated 37C for 1 hour. After this the reaction was purified and concentrated using a PCR purification kit. The purified product and pRSFGFP was digested with PstI and HindIII (NEB) overnight at 37° C. The digestion products were purified and ligated together using T4 ligase (NEB). The resulting ligation mixture was used to transform *E. coli* BL21 (DE3) which was subsequently plated onto LB agar supplemented with 50 ug/mL kanamycin and incubated at 37° C. until visible colonies formed. Colonies were used to inoculate LB broth and incubated under aeration at 37° C. for 18 h. Plasmid extractions were performed on the overnight cultures.

For fusion of TATBeclin to mCherry additional primers were required (TATBmCherry; SEQ ID. 78 and 79). The forward primer has a BamHI site (with a WELQut protease) and the reverse primer has a NotI site (Table 1). TATBeclin was amplified out of the pRSF-GFPTATB (SEQ ID. 80 and 81) construct using these primers. The resulting PCR product was purified and digested with BamHI and NotI. Similarly, the plasmid containing mCherry for C-terminal fusion was digested with the same restriction enzymes. The digested TAT-Beclin and plasmid were purified, ligated and transformed as previously described.

TATBeclin fusions were expressed and purified as described in examples 1-2. The eluents were desalted against PBS buffer with 250 mM or 150 mM NaCl for GFPTAT-Beclin and TATmCherry, respectively using 20 kDa dialysis cassettes (20 kDa Cutoff) or 10 kDa protein concentrators (10 kDa cut-off).

Both fusions were successfully expressed and purified using immobilized metal affinity chromatography (IMAC). Preliminary total protein yields of IMAC purified and desalted samples were 113.8 mg/L for GFPTATB and 41.7 mg/L TATBmCherry. The relative purity of the samples as determined by SDS PAGE ranged from 70-82% for GFP-TATB and 48-50% for TATBmCherry (FIG. 23). These yields and purities can be further increased by optimization of the process and use of specialized strains and techniques.

TABLE 7

Buffers used in the Examples

| Buffer | Composition | Description |
|---|---|---|
| Terrific Broth (TB) | To 900 mL dH$_2$O add Tryptone - 12 g, Yeast Extract - 24 g, Glycerol - 4 mL. Autoclave. After autoclave add 10x TB Buffer: 170 mM KH$_2$PO$_4$, 720 mM K$_2$HPO$_4$, and autoclave, add to TB to make up 1 L TB broth. | Expression media for heterologous expression in *E. coli*. |
| Start Buffer (SB) | 50 mM Tris, 500 mM NaCl, pH 8.0. Filter (0.45 μm cellulose acetate filter) and autoclave. | Buffer used for lysis and purification of heterologously expressed proteins in soluble fraction of *E. coli*. Imidazole is added to appropriate concentration for washing and elution. |
| Lysis Buffer | SB buffer supplemented with 1 mg/mL lysozyme, 1 U/mL RNAse and 6 U/mL DNAse and protease inhibitors | Standard buffer used for lysis *E. coli* during purification of heterologously expressed proteins. |
| Phosphate Buffered Saline (PBS) | 10 mM Na$_2$HPO$_4$, 1.8 mM KH$_2$PO$_4$, 2.7 mM KCl, 140 mM NaCl, pH 7.4. Filter (0.45 μm cellulose acetate filter) and autoclave | Buffer used for desalting. |

Example 7

Design of Additional RNA Thermometers and Use of Stationary Phase Promoters

To further improve on the proof-of-concept different RNA thermometers (RNATs) can be used in combination with stationary phase promoters. Examples of RNATs include SEQ ID NOs: 19-27 and SEQ ID NOs: 105-111 and promoters included SEQ ID NOs: 74-76. To illustrate this the RNAT/promoter combinations of SEQ ID NO: 81 (G5), SEQ ID NO:84 (G8), SEQ ID NO:91 (G15), SEQ ID NO:93 (G17) and SEQ ID NO:94 (G18) was used for preliminary illustration. The different promoter/RNAT combinations were cloned into the vector pHXk (SEQ ID NO: 101) using the restriction enzymes KasI and BamHI. The vector pHXk was designed to include a Kanamycin resistance gene, LacIq (lac repressor) gene, pUC19 origin of replication and two multiple cloning sites (MCS) with their own T7 promoter and LacO operator followed by transcription stop sequences L3S2P56 and BBa0015, respectively (Restriction enzyme sites for MCS1-PacI, NdeI, BamHi, XhoI, PstI, NotI MfeI; MCS2-NcoI, BglII, SalI, SacI, HindIII, EcoRI). A second vector was designed (SEQ ID NO: 102), using the same backbone plasmid with a chloramphenicol resistance marker instead of kanamycin. An additional two vectors were designed (SEQ ID NO:103-104), using the same basic vector sequence as described above, with alterations in the sequences between their respective promoters/operators and start codons and differences in the multiple cloning sites: MCS1 has the BBa0015 transcriptional terminator and MCS2 has a T7 terminator. Subsequently the lytic protein GPR was cloned into these new vectors using BamHI and XhoI. These new vectors were then used to transform *E. coli* BL21 and used for preliminary evaluation.

An experiment using the different *E. coli* BL21 constructs was performed to simulate expression conditions. Cultures were inoculated into 5 mL Luria Bertani (LB) broth (supplemented with 50 ug/mL Kanamycin) and grown overnight at 26° C. The overnight cultures were subsequently used to inoculate 150 mL LB broth at 1% v/v and incubated at 26° C. until cultures reached an OD600 of between 0.6-0.8. Subsequently, 50 mL of each culture were split into flasks and either grown at 26° C. or 37° C. Readings were taken every 2 hours for 12 hours. After 15 hours (total incubation time) cells were incubated for an additional 11 hours (for a total of 26 hours). After 26 hours all remaining samples grown at 26° C. were moved and incubated at 37° C. for an additional 5 hours.

All optical density readings were taken using a cuvette and a SmartSPec Plus (Biorad). When needed samples were diluted in Tris buffer (pH 7.4) to keep OD600 values below 1.0.

At selected time points 1 mL culture was taken and centrifuged at 8000 rpm (2 min) and pellets frozen at −20° C. for at least 2 hours. After freezing cells pellets were thawed at room temperature and resuspended in 1 mL Lysis buffer (Tris buffer (pH 7.4) supplemented with 25 U/mL ThermoScientific Universal Nuclease). After 5 min incubation at room temperature optical density readings were taken as described above (dilutions were made where needed as described above).

To calculate the % lysis the optical density readings obtained from each resuspended freeze-thaw pellet (ODFreeze) was divided by the optical density reading of its original culture before freezing (ODOriginal) (Equation 1).

$$\% \text{ lysis} = (1 - \text{ODFreeze}/\text{ODOriginal}) \times 100 \quad \text{Equation 1}$$

Figure 24:
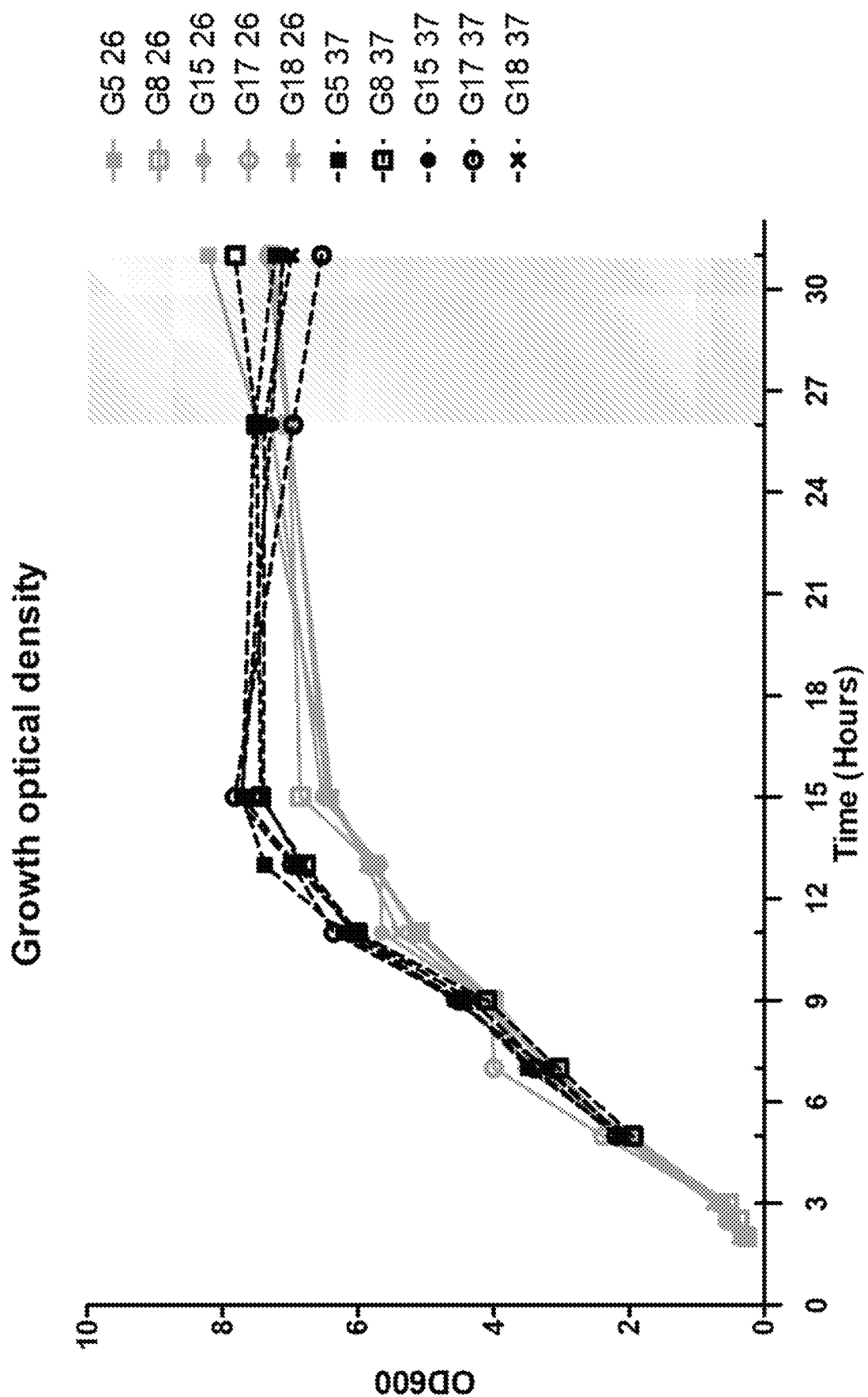
FIG. 24: Optical density readings of the different *E. coli* constructs grown at 26° C. (solids lines) and 37° C. (dashed lines). Shaded grey block indicates the move of samples grown at 26° C. to 37° C. for an additional 5 hours of growth
Figure 25:
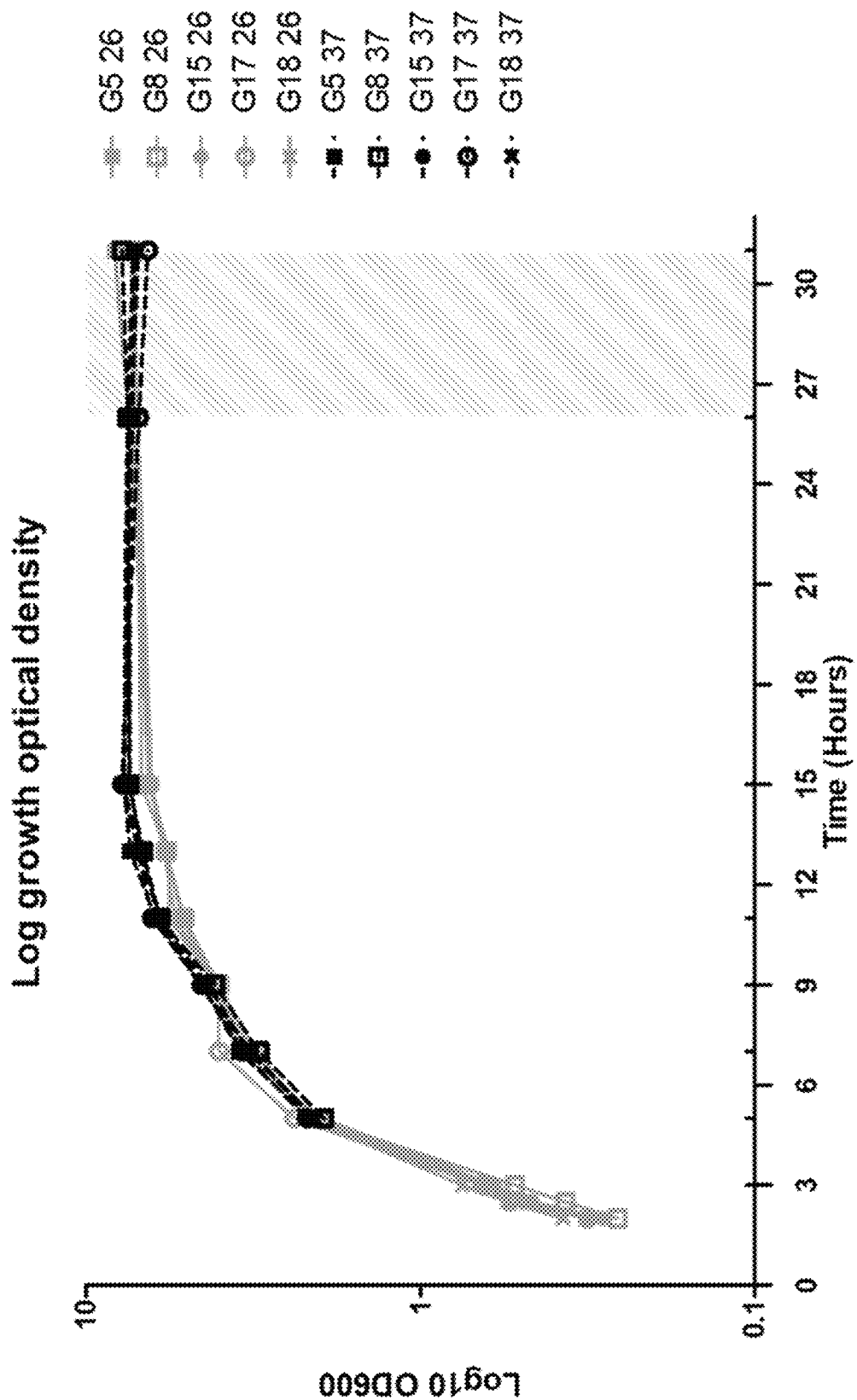
FIG. 25: Log graph of optical density readings of the different *E. coli* constructs grown at 26° C. (solids lines) and 37° C. (dashed lines). Shaded grey block indicates the move of samples grown at 26° C. to 37° C. for an additional 5 hours of growth.
Figure 26:
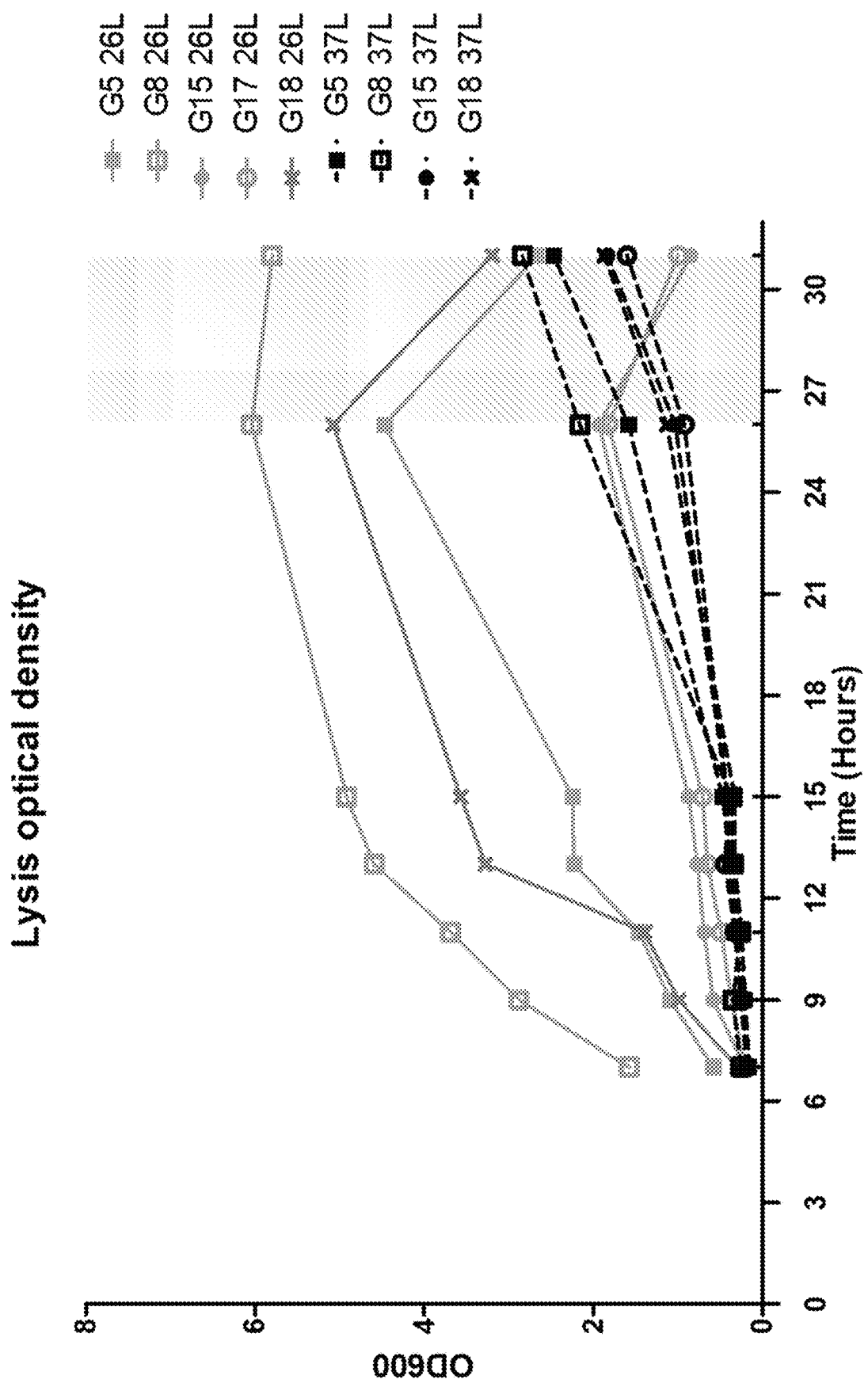
FIG. 26: Optical density readings of the different *E. coli* constructs (after lysis) grown at different temperatures after one freeze thaw cycle. 26° C. (solids lines) and 37° C. (dashed lines). Shaded grey block indicates the move of samples grown at 26° C. to 37° C. for an additional 5 hours of growth.
Figure 27:
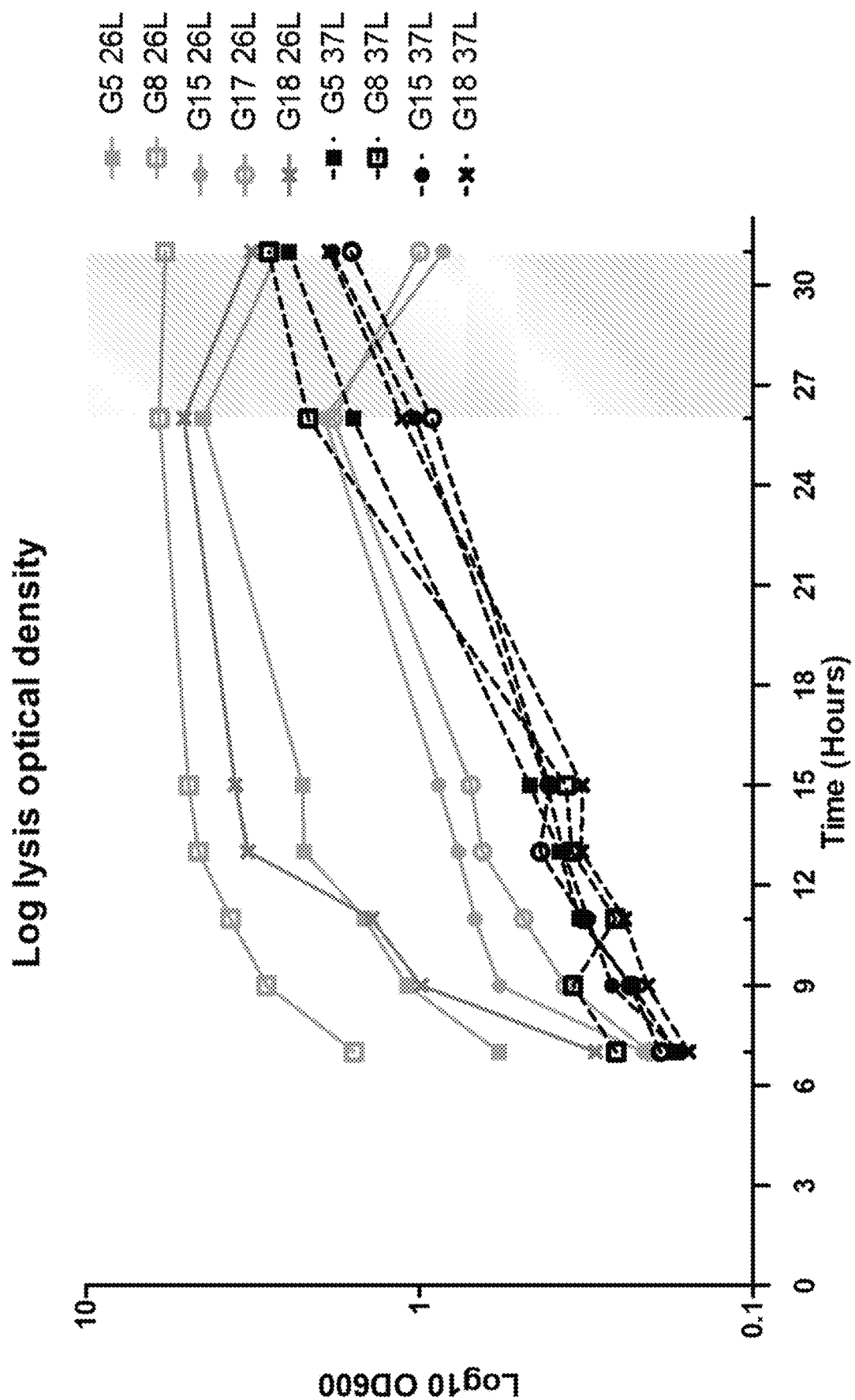
FIG. 27: Log optical density readings of the different *E. coli* constructs (after lysis) grown at different temperatures after one freeze thaw cycle. 26° C. (solids lines) and 37° C. (dashed lines). Shaded grey block indicates the move of samples grown at 26° C. to 37° C. for an additional 5 hours of growth.
Figure 28:
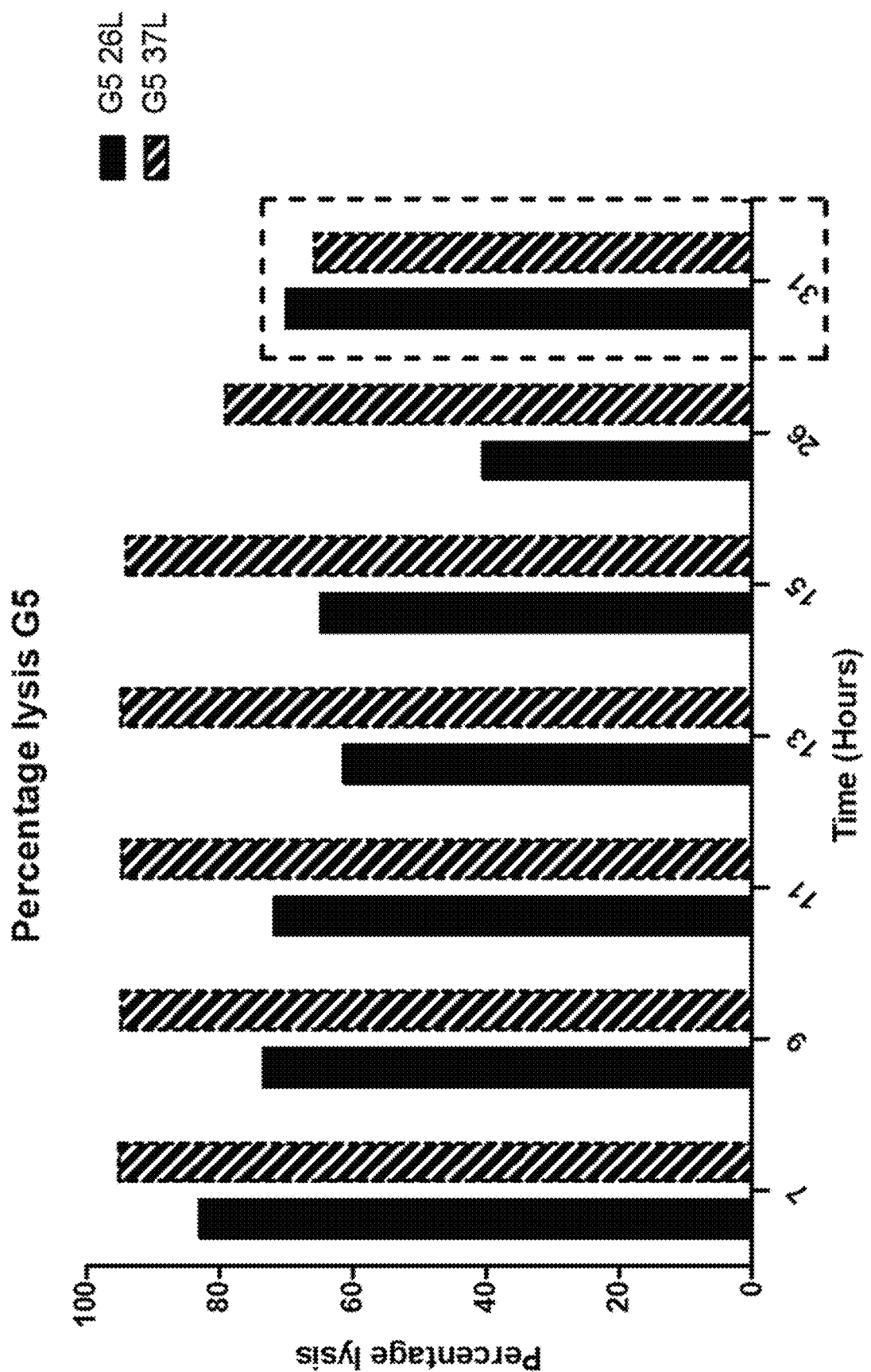
FIG. 28: Percentage lysis of the sample G5 grown at different temperatures after one freeze thaw cycle. Dashed square indicates the move of samples grown at 26° C. to 37° C. for an additional 5 hours of growth.
Figure 29:
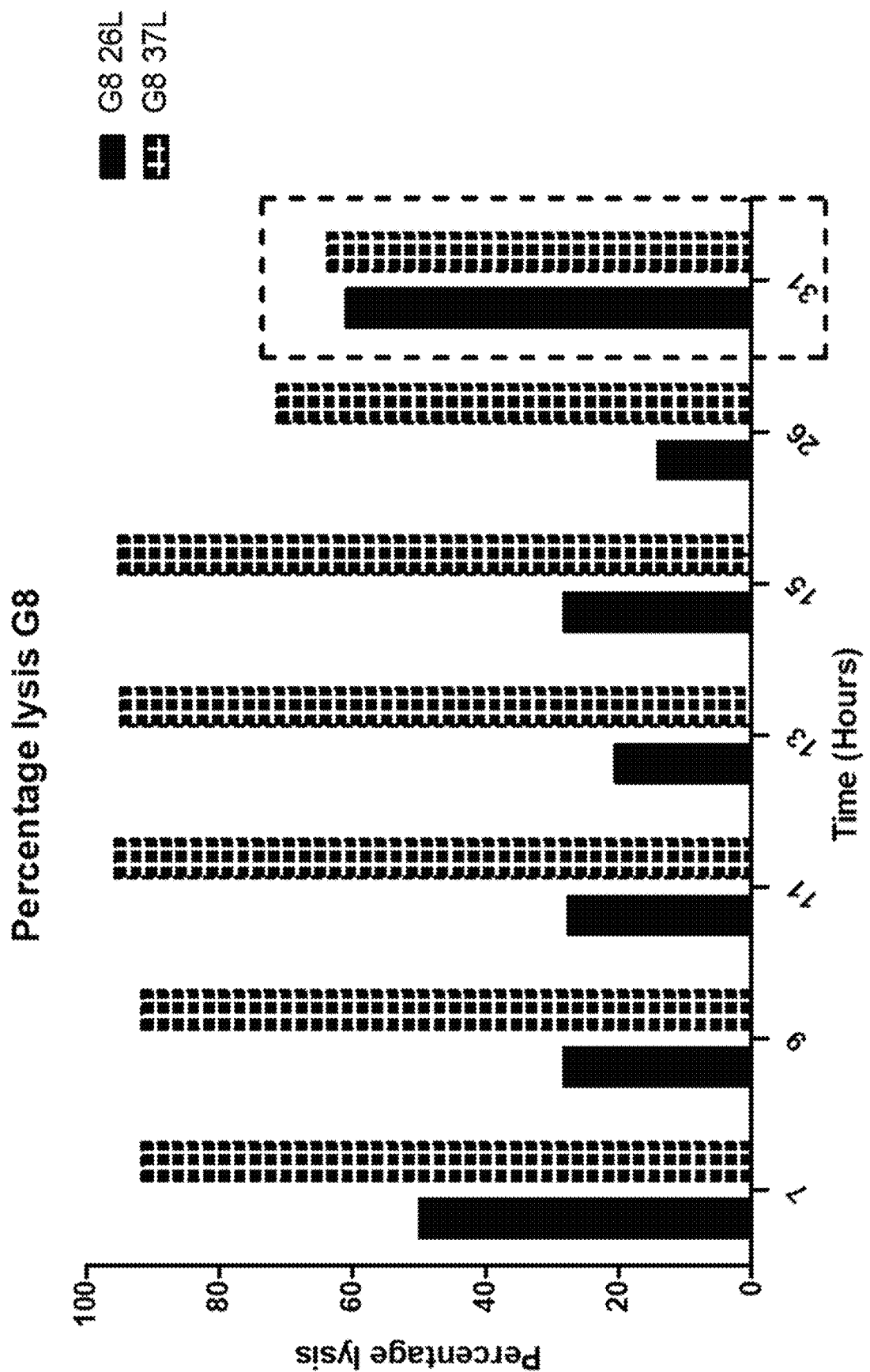
FIG. 29: Percentage lysis of the sample G8 grown at different temperatures after one freeze thaw cycle. Dashed square indicates the move of samples grown at 26° C. to 37° C. for an additional 5 hours of growth.
Figure 30:
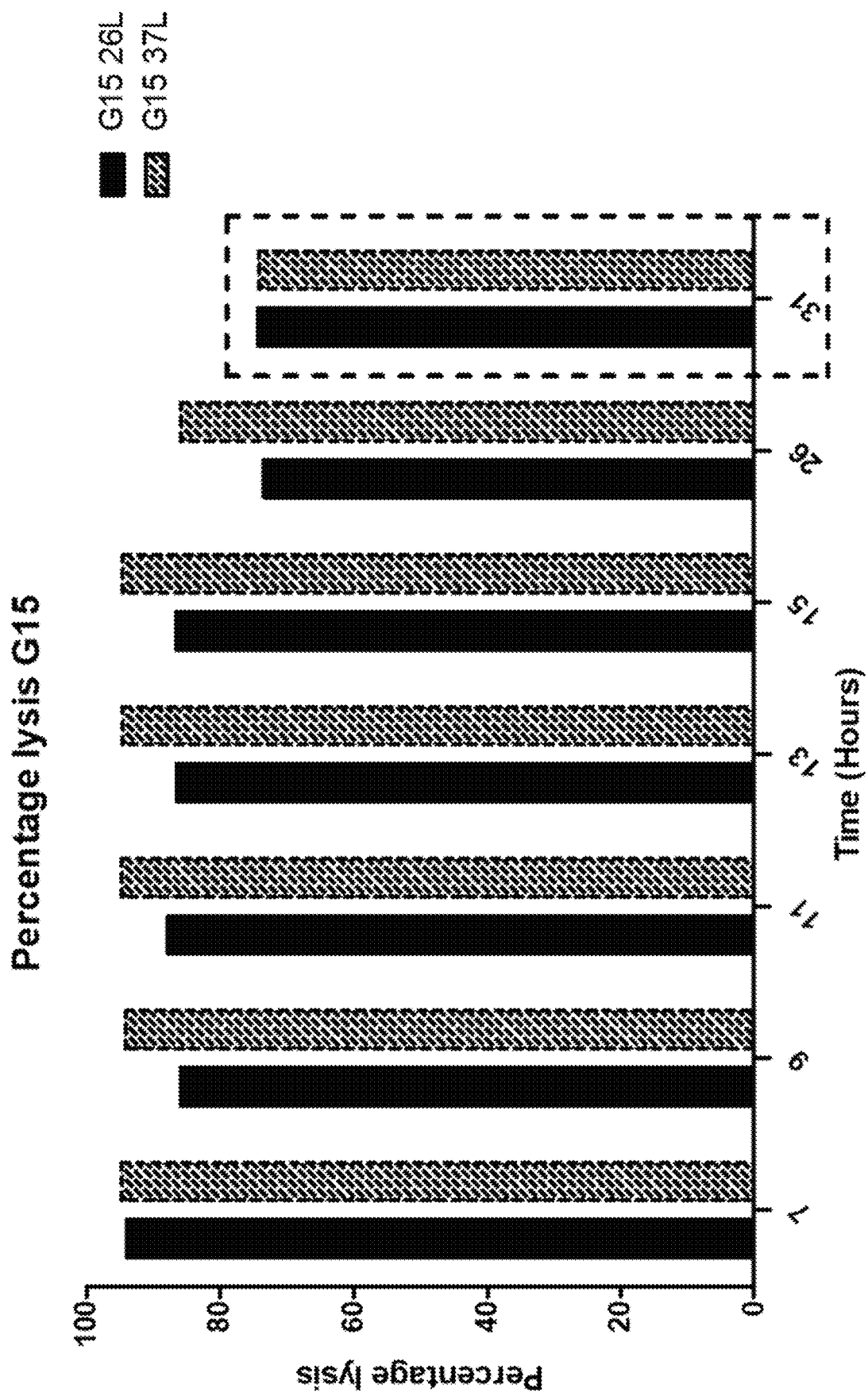
FIG. 30: Percentage lysis of the sample G15 grown at different temperatures after one freeze thaw cycle. Dashed square indicates the move of samples grown at 26° C. to 37° C. for an additional 5 hours of growth.
Figure 31:
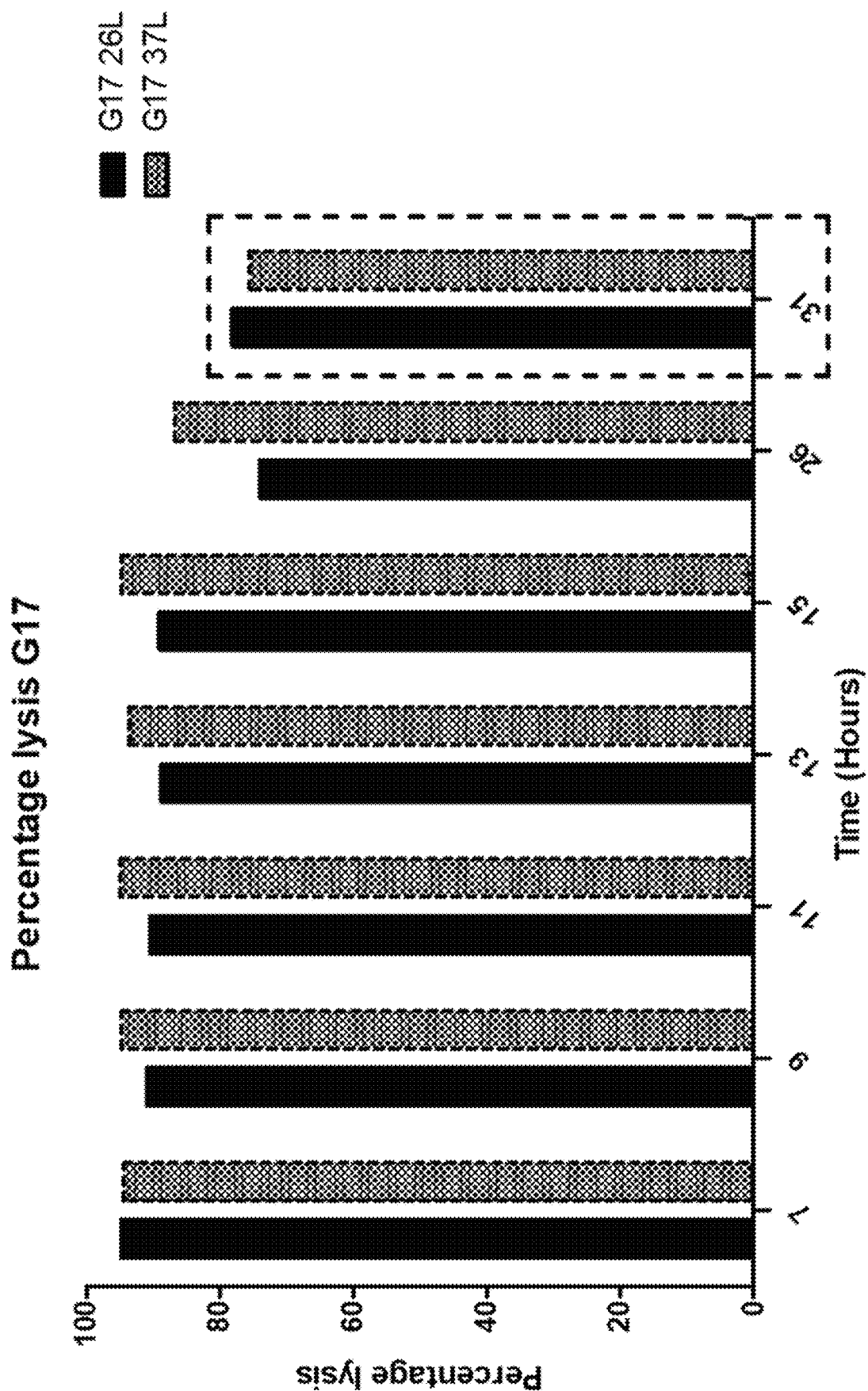
FIG. 31: Percentage lysis of the sample G17 grown at different temperatures after one freeze thaw cycle. Dashed square indicates the move of samples grown at 26° C. to 37° C. for an additional 5 hours of growth.
Figure 32:
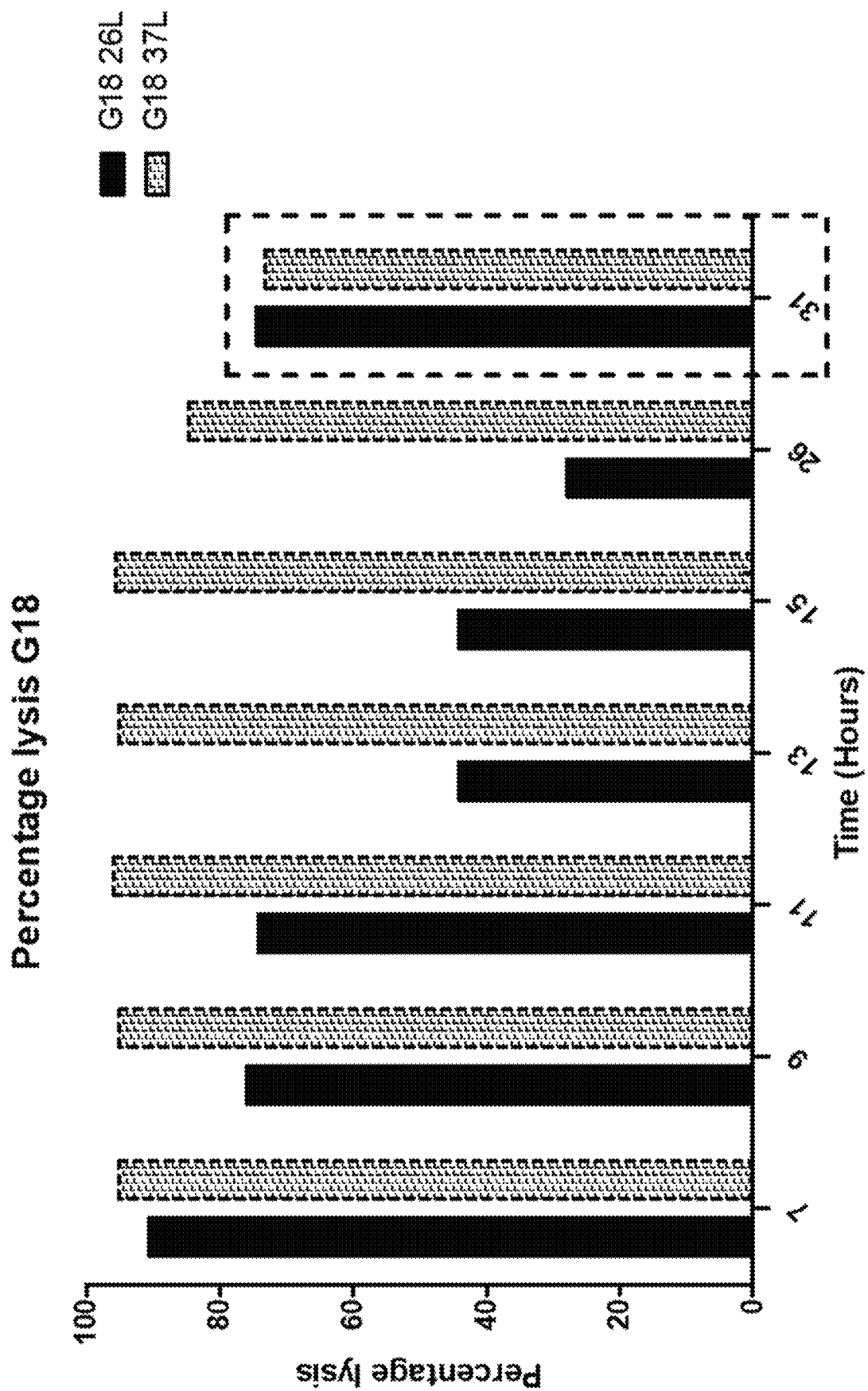
FIG. 32: Percentage lysis of the sample G18 grown at different temperatures after one freeze thaw cycle. Dashed square indicates the move of samples grown at 26° C. to 37° C. for an additional 5 hours of growth.

*E. coli* B21 promoter/RNAT constructs grown at 26° C. reached an OD600 of 0.6-0.8 in 3 hours and subsequent growth of constructs at 37° C. resulted increased optical density values compared to those grown at 26° C. up until 15 hours (FIGS. 24 and 25). At 26 hours optical density values of cells grown at 26° C. and 37° C. had similar OD600 values. Cells grown at 26° C. and moved to 37° C. for an additional 5 hours showed slight increases in OD600 values with sample G5 indicating the largest change. Overall, all the constructs reached a high OD600 with an average of 7.25 (+/−0.22) with early stationary phase achieved after 15 hours (FIGS. 24 and 25).

Samples (1 mL) were collected at 7, 9, 11, 13, 15, 26 and +5 (31) hours spun down and frozen at −20° C. These samples were then resuspended in lysis buffer to determine the percentage lysis as a function of the original OD600 value of each culture (Equation 1). Lysis was consistently weaker for samples grown at 26° C. with more lysis observed at early time points (FIGS. 26-32). This is most likely because of basal GPR expression and increased sensitivity of young cells towards membrane damage after freeze thaw cycle. Samples G5, G8 and G18 indicated a clear difference in lysis with cells grown at 37° C. indicating lysis of >90% up until 15 hours (FIGS. 26-27, 28, 29, 32). After 26 hours of growth lysis decreased for samples grown at 26° C. and 37° C. and is most likely due to thicker cell walls of older cells that are more resistant to damage from freeze thaw. The biggest difference between lysis of samples grown at 26° C. and 37° C. was however observed at this late time point, with samples grown at 37° C. having more lysis (70-85%) compared to those grown at 26° C. (14-74%) (FIGS. 26-32). At this later time point samples G5, G8 and G18 had the biggest difference in lysis between samples grown at 26° C. or 37° C. (FIGS. 26-27, 28, 29, 32). After moving cells grown previously incubated at 26° C. to 37° C. (for an additional 5 hours) an increase in lysis consistent with those grown at 37° C. was observed—this is indicative of increased expression/translation of the GPR lysis gene and is consistent with the function of the RNATs.

From these results the use of RNATs with a stationary phase promoter result in different lysis efficiencies when cells are grown at either a low (26° C.) or high (37° C.) temperature. Furthermore, these preliminary results indicate that a shift of cells from a low to a high temperature at late stationary phase can result in increased lysis efficiency. The results also illustrate that the different RNATs have different efficiencies in terms of their ability to throttle the expression/translation of the lysis at lower temperatures. This allows for the selection of RNATs depending on the specific need/application.

Taken together these results further illustrate the application of RNAT/stationary phase promoter combinations for the lysis of recombinant *E. coli* cells.

TABLE 8

Percentage lysis of cells after one freeze thaw cycle

| | Lysis percentage | | | | | | | | | |
|---|---|---|---|---|---|---|---|---|---|---|
| Time (hours) | G5 26° C. | G8 26° C. | G15 26° C. | G17 26° C. | G18 26° C. | G5 37° C. | G8 37° C. | G15 37° C. | G17 37° C. | G18 37° C. |
| 7 | 82.9 | 49.8 | 94.0 | 94.9 | 90.6 | 95.1 | 91.5 | 94.8 | 94.4 | 95.2 |
| 9 | 73.4 | 28.2 | 85.8 | 90.9 | 76.0 | 94.8 | 91.6 | 94.2 | 94.8 | 95.2 |
| 11 | 71.7 | 27.5 | 87.9 | 90.5 | 74.3 | 94.8 | 94.8 | 94.7 | 94.9 | 96.0 |
| 13 | 61.4 | 20.3 | 86.5 | 88.8 | 44.1 | 94.9 | 94.9 | 94.7 | 93.8 | 95.2 |
| 15 | 64.8 | 28.2 | 86.6 | 89.1 | 44.1 | 93.9 | 95.1 | 94.6 | 94.8 | 95.6 |
| 26 | 40.4 | 14.0 | 73.5 | 74.1 | 27.8 | 79.0 | 71.2 | 85.9 | 86.8 | 84.7 |
| +5 (31) | 70.0 | 60.9 | 74.3 | 78.1 | 74.5 | 65.8 | 63.7 | 74.2 | 75.5 | 73.2 |

The invention claimed is:

1. A method of producing one or more heterologous polypeptides in an *E. coli* host cell, the method comprising:
   (i) providing an expression vector encoding at least one fusion protein comprising the one or more heterologous polypeptides and a fluorescent fusion partner;
   (ii) transforming the *E. coli* host cell with the expression vector of step (i), wherein the *E. coli* host cell and/or the expression vector is modified to include a nucleic acid encoding a stationary phase promoter, a lytic protein, wherein the lytic protein is an endolysin or a bacterial murein hydrolase, and an RNA thermometer, further wherein expression of the nucleic acid encoding the lytic protein is regulated by the promoter and translation of the lytic protein is regulated by the RNA thermometer;
   (iii) expressing the at least one fusion protein in the *E. coli* host cell;
   (iv) modifying the temperature of the *E. coli* host cell to induce translation of the lytic protein, wherein translation of the lytic protein results in lysis of the *E. coli* host cell; and
   (v) recovering the at least one fusion protein from the *E. coli* host cell.

2. The method of claim 1, wherein the at least one fusion protein includes one or more purification tags and wherein the method further comprises a step of purifying the recovered at least one fusion protein.

3. The method of claim 2, wherein the purification tag is a histidine (His) tag and/or a Glutathione S-transferase (GST) tag.

4. The method of claim 1, wherein the at least one fusion protein includes a protease cleavage site and wherein the method further comprises a step of cleaving the fluorescent fusion partner from the one or more heterologous polypeptides after recovery.

5. The method of claim 4, wherein the protease cleavage site is selected from the group consisting of a WELQut site comprising the amino acid sequence WELQ (SEQ ID NO:1) encoded by a nucleic acid comprising the sequence TGG-GAACTGCAG (SEQ ID NO:2), a thrombin or trypsin cleavage site comprising the amino acid sequence LVPR (SEQ ID NO:3) encoded by a nucleic acid comprising the sequence CTAGTACCACGC (SEQ ID NO: 4), a nisP or trypsin cleavage site comprising the amino acid sequence ASPR (SEQ ID NO: 5) encoded by a nucleic acid comprising the sequence GCGAGCCCGCGC (SEQ ID NO:6), a TEV cleavage site-comprising the amino acid sequence ENLYFQG (SEQ ID NO:7) encoded by a nucleic acid-comprising the sequence GAAAACTTGTATTTT-CAAGGC (SEQ ID NO:8), a Factor Xa cleavage site comprising the amino acid sequence IEGR (SEQ ID NO:9) encoded by a nucleic acid comprising the sequence ATT-GAAGGTCGT (SEQ ID NO:10), and any combination thereof.

6. The method of claim 1, wherein the at least one fusion protein includes a secretion signal peptide.

7. The method of claim 1, wherein the fluorescent fusion partner is selected from the group consisting of green fluorescent protein, yellow fluorescent protein, blue fluorescent protein, cyan fluorescent protein, and a red fluorescent protein.

8. The method of claim 7, wherein the green fluorescent protein comprises the amino acid sequence of SEQ ID NO:11 or is encoded by a nucleic acid comprising the nucleotide sequence of SEQ ID NO:12.

9. The method of claim 7, wherein the red fluorescent protein is mCherry comprising the amino acid sequence of SEQ ID NO: 13 or is encoded by a nucleic acid comprising the nucleotide sequence of SEQ ID NO:14.

10. The method of claim 1, wherein the one or more heterologous polypeptides are selected from the group consisting of a lanthipeptide; a bacteriocin; Listeriolysin O; ActA; and autophagic peptideX.

11. The method of claim 1, wherein the RNA thermometer comprises the nucleic acid sequence of any one of SEQ ID NOs: 19-27 or SEQ ID NOs: 105-111 and the stationary phase promoter comprises the nucleic acid sequence of any one of SEQ ID NOs: 74-76.

12. The method of claim 1, wherein expression of the lytic protein results in lysis of the *E. coli* host cell upon subsequent freeze-thawing of the *E. coli* host cells and resuspension in a lysis buffer.

13. The method of claim 10, wherein the lanthipeptide is Nisin, epilancin 15X, or Pep5.

14. The method of claim 10, wherein the bacteriocin is plantaricin 423 or mundticin ST4SA.

15. The method of claim 1, wherein the lytic protein comprises the amino acid sequence of SEQ ID NO:15 or SEQ ID NO: 17 or is encoded by a nucleic acid comprising the nucleotide sequence of SEQ ID NO: 16 or SEQ ID NO: 18.

16. The method of claim 11, wherein a combination of the stationary phase promoter and RNA thermometer comprises a sequence as shown in any one of SEQ ID Nos: 77-100.

17. An *E. coli* cell, wherein the cell comprises:
(i) at least one expression vector encoding at least one fusion protein comprising one or more heterologous polypeptides and a fluorescent fusion partner; and
(ii) a nucleic acid encoding a stationary phase promoter operably linked to a lytic protein, wherein the lytic protein is an endolysin or a bacterial murein hydrolase, and an RNA thermometer,
wherein the RNA thermometer is capable of regulating translation of the lytic protein.

18. The cell of claim 17, wherein the at least one fusion protein includes a purification tag.

19. The cell of claim 18, wherein the purification tag is a histidine (His) tag or a Glutathione S-transferase (GST) tag.

20. The cell of claim 17, wherein the at least one fusion protein includes a protease cleavage site.

21. The cell of claim 20, wherein the protease cleavage site is selected from the group consisting of a WELQut site comprising the amino acid sequence WELQ (SEQ ID NO: 1) encoded by a nucleic acid comprising the sequence TGGGAACTGCAG (SEQ ID NO: 2), a thrombin or trypsin cleavage site comprising the amino acid sequence LVPR (SEQ ID NO: 3) encoded by a nucleic acid comprising the sequence CTAGTACCACGC (SEQ ID NO:4), a nisP or trypsin cleavage site comprising the amino acid sequence ASPR (SEQ ID NO:5) encoded by a nucleic acid comprising the sequence GCGAGCCCGCGC (SEQ ID NO:6), a TEV cleavage site comprising the amino acid sequence ENLYFQG (SEQ ID NO:7) encoded by a nucleic acid comprising the sequence GAAAACTTGTATTTT-CAAGGC (SEQ ID NO:8), a Factor Xa cleavage site comprising the amino acid sequence IEGR (SEQ ID NO:9) encoded by a nucleic acid comprising the sequence ATT-GAAGGTCGT (SEQ ID NO:10), and any combination thereof.

22. The cell of claim 17, wherein the at least one fusion protein includes a secretion signal peptide.

23. The cell of claim 17, wherein the fluorescent fusion partner is selected from the group consisting of green fluorescent protein, yellow fluorescent protein, blue fluorescent protein, cyan fluorescent protein, and a red fluorescent protein.

24. The cell of claim 23, wherein the green fluorescent protein comprises the amino acid sequence of SEQ ID NO:11 or is encoded by a nucleic acid comprising the nucleotide sequence of SEQ ID NO:12.

25. The cell of claim 23, wherein the red fluorescent protein is mCherry comprising the amino acid sequence of SEQ ID NO: 13 or is encoded by a nucleic acid comprising the nucleotide sequence of SEQ ID NO: 14.

26. The cell of claim 17, wherein the one or more heterologous polypeptides are selected from the group consisting of a lanthipeptide; a bacteriocin; Listeriolysin O; ActA; and autophagic peptideX.

27. The cell of claim 17, wherein the RNA thermometer comprises the nucleic acid sequence of any one of SEQ ID NOs: 19-27 or SEQ ID NOs: 105-111 and the stationary phase promoter comprises the nucleic acid sequence of any one of SEQ ID NOs: 74-76.

28. The cell of claim 17, wherein expression of the lytic protein results in lysis of the cell upon subsequent freeze-thawing of cells and resuspension in a lysis buffer.

29. The cell of claim 26, wherein the lanthipeptide is Nisin, epilancin 15X, or Pep5.

30. The cell of claim 26, wherein the bacteriocin is plantaricin 423 or mundticin ST4SA.

31. The cell of claim 17, wherein the lytic protein comprises the amino acid sequence of SEQ ID NO:15 or SEQ ID NO:17 or is encoded by a nucleic acid comprising the nucleotide sequence of SEQ ID NO:16 or SEQ ID NO:18.

32. The cell of claim 27 wherein a combination of the stationary phase promoter and RNA thermometer comprises a sequence as shown in any one of SEQ ID NOs: 77-100.

33. A kit comprising:
at least one expression vector for expressing at least one fusion protein comprising one or more heterologous polypeptides and a fluorescent fusion partner; and
an *E. coli* cell,
wherein the cell and/or the expression vector comprises a nucleic acid encoding a stationary phase promoter operably linked to a lytic protein, wherein the lytic protein is an endolysin or a bacterial murein hydrolase, and an RNA thermometer, wherein the RNA thermometer is capable of regulating translation of the lytic protein.

* * * * *